United States Patent
Szalay et al.

(10) Patent No.: US 8,137,904 B2
(45) Date of Patent: *Mar. 20, 2012

(54) LIGHT EMITTING MICROORGANISMS AND CELLS FOR DIAGNOSIS AND THERAPY OF DISEASES ASSOCIATED WITH WOUNDED OR INFLAMED TISSUE

(75) Inventors: Aladar A. Szalay, Highland, CA (US); Shahrokh Shabahang, Redland, CA (US); Yong A. Yu, San Diego, CA (US)

(73) Assignee: Genelux Corporation, San Diego, CA (US)

(*) Notice: Subject to any disclaimer, the term of this patent is extended or adjusted under 35 U.S.C. 154(b) by 622 days.

This patent is subject to a terminal disclaimer.

(21) Appl. No.: 10/516,785

(22) PCT Filed: Jun. 5, 2003

(86) PCT No.: PCT/EP03/05907
§ 371 (c)(1), (2), (4) Date: Jun. 27, 2005

(87) PCT Pub. No.: WO03/104485
PCT Pub. Date: Dec. 18, 2003

(65) Prior Publication Data
US 2005/0249670 A1    Nov. 10, 2005

(30) Foreign Application Priority Data
Jun. 5, 2002 (EP) ..................... 02012552

(51) Int. Cl.
*C12Q 1/00* (2006.01)
*C12Q 1/66* (2006.01)
*A61K 39/108* (2006.01)

(52) U.S. Cl. .................. 435/4; 435/8; 435/29; 424/9.1; 424/9.6

(58) Field of Classification Search .................. None
See application file for complete search history.

(56) References Cited

U.S. PATENT DOCUMENTS

| | | |
|---|---|---|
| 4,442,203 A | 4/1984 | Varshavsky |
| 4,722,848 A | 2/1988 | Paoletti et al. |
| 4,778,759 A | 10/1988 | Szalay et al. |
| 5,221,623 A | 6/1993 | Legocki et al. |
| 5,283,187 A | 2/1994 | Aebischer et al. |
| 5,300,436 A | 4/1994 | Goldstein et al. |
| 5,550,050 A | 8/1996 | Holland et al. |
| 5,639,275 A | 6/1997 | Baetge et al. |
| 5,646,298 A | 7/1997 | Powell et al. |
| 5,650,135 A | 7/1997 | Contag et al. |
| 5,650,148 A | 7/1997 | Gage et al. |
| 5,653,975 A | 8/1997 | Baetge et al. |
| 5,656,481 A | 8/1997 | Baetge et al. |
| 5,676,943 A | 10/1997 | Baetge et al. |
| 5,693,533 A | 12/1997 | Raney et al. |
| 5,704,910 A | 1/1998 | Humes |
| 5,718,902 A | 2/1998 | Yilma et al. |
| 5,750,103 A | 5/1998 | Cherksey |
| 5,756,455 A | 5/1998 | Kinzler et al. |
| 5,762,959 A | 6/1998 | Soon-Shiong et al. ....... 424/451 |
| 5,795,790 A | 8/1998 | Schinstine et al. |
| 5,798,113 A | 8/1998 | Dionne et al. |
| 5,800,828 A | 9/1998 | Dionne et al. |
| 5,800,829 A | 9/1998 | Dionne et al. |
| 5,830,702 A | 11/1998 | Portnoy et al. |
| 5,833,975 A | 11/1998 | Paoletti et al. ............... 424/93.2 |
| 5,833,979 A | 11/1998 | Schinstine et al. |
| 5,834,001 A | 11/1998 | Dionne et al. |
| 5,837,234 A | 11/1998 | Gentile et al. |
| 5,840,576 A | 11/1998 | Schinstine et al. |
| 5,842,431 A | 12/1998 | Wu |
| 5,853,385 A | 12/1998 | Emerich et al. |
| 5,853,717 A | 12/1998 | Schinstine et al. |
| 5,861,290 A | 1/1999 | Goldsmith et al. |
| 5,976,796 A | 11/1999 | Szalay et al. |
| 6,007,806 A | 12/1999 | Lathe et al. |
| 6,025,155 A | 2/2000 | Hadlaczky et al. |
| 6,045,802 A | 4/2000 | Schlom et al. |
| 6,077,697 A | 6/2000 | Hadlaczky et al. |
| 6,080,849 A | 6/2000 | Bermudes et al. |
| 6,093,700 A | 7/2000 | Mastrangelo et al. |
| 6,099,848 A | 8/2000 | Frankel et al. |
| 6,106,826 A | 8/2000 | Brandt et al. |
| 6,150,170 A | 11/2000 | Powell et al. ................. 435/455 |

(Continued)

FOREIGN PATENT DOCUMENTS

AU    709336    4/1995

(Continued)

OTHER PUBLICATIONS

Weissleder et al. (2001) Radiol. 219:316-333.*
Wade et al. 2006: Am. J. Respir. Cell Mol. Biol. 34:727-737.*
MacMahon et al. (2005) Curr. Drug Targets 5:433-440.*
Jawien et al. (2004) J. Physiol. Pharmacol. 55:503-517.*
Aboody et al., "Neural stem cells display extensive tropism for pathology in adult brain: evidence from intracranial gliomas," Proc Natl Acad Sci U S A. 97(23):12846-51 (2000).
Aksac S., "[Antibody formation against Agrobacterium tumefaciens in patients with various cancers]," Turk Hij Tecr Biyol Derg. 34(1-2):48-51 (1974) [Article in Italian].
Al'tshtein et al., "[Isolation of a recombinant vaccinia virus based on the LIVP strain inducing the surface antigen of the hepatitis B virus]," Dokl Akad Nauk SSSR. 285(3):696-9 (1985) [Article in Russian].
Anaissie et al., "*Pseudomonas putida.* Newly recognized pathogen in patients with cancer;" Am J Med. 82(6):1191-4 (1987).

(Continued)

*Primary Examiner* — Michael Burkhart
(74) *Attorney, Agent, or Firm* — McKenna Long & Aldridge LLP; Stephanie Seidman

(57) ABSTRACT

Described is the use of a microorganism or cell containing a DNA sequence encoding a detectable protein or a protein capable of inducing a detectable signal, e.g., a luminescent or fluorescent protein for the preparation of a diagnostic composition for diagnosis and/or visualization of wounded or inflamed tissue or a disease associated therewith. Moreover, therapeutic uses are described, wherein the microorganism or cell additionally contain an expressible DNA sequence encoding a protein suitable for therapy, e.g. an enzyme causing cell death or digestion of debris.

24 Claims, 7 Drawing Sheets

U.S. PATENT DOCUMENTS

| | | |
|---|---|---|
| 6,190,657 B1 | 2/2001 | Pawelek et al. |
| 6,217,847 B1 | 4/2001 | Contag et al. |
| 6,232,523 B1 | 5/2001 | Tan et al. |
| 6,235,967 B1 | 5/2001 | Tan et al. |
| 6,235,968 B1 | 5/2001 | Tan et al. |
| 6,251,384 B1 | 6/2001 | Tan et al. |
| 6,265,557 B1 | 7/2001 | Diamond et al. |
| 6,359,189 B1 | 3/2002 | Fleischmann |
| 6,416,754 B1 | 7/2002 | Brown et al. |
| 6,428,968 B1 | 8/2002 | Molnar-Kimber et al. |
| 6,455,673 B1 | 9/2002 | Collier |
| 6,491,905 B1 | 12/2002 | Sorscher et al. |
| 6,503,703 B1 | 1/2003 | Palese et al. |
| 6,511,967 B1 | 1/2003 | Weissleder et al. |
| 6,548,068 B1 | 4/2003 | Schlom et al. |
| 6,589,531 B1 | 7/2003 | Andino-Pavlovsky et al. |
| 6,596,279 B1 | 7/2003 | Paoletti et al. |
| 6,627,190 B2 | 9/2003 | Wold et al. |
| 6,649,143 B1 | 11/2003 | Contag et al. |
| 6,649,159 B2 | 11/2003 | Yang et al. |
| 6,652,849 B2 | 11/2003 | Brown et al. |
| 6,685,935 B1 | 2/2004 | Pawelek et al. |
| 6,713,293 B1 | 3/2004 | Grummt et al. |
| 6,743,967 B2 | 6/2004 | Hadlaczky et al. |
| 6,759,038 B2 | 7/2004 | Tan et al. |
| 6,916,462 B2 | 7/2005 | Contag et al. ............ 424/9.6 |
| 6,984,374 B2 | 1/2006 | Szalay et al. |
| 7,588,767 B2 | 9/2009 | Szalay et al. ............ 424/199.1 |
| 7,588,771 B2 | 9/2009 | Szalay et al. ............ 424/232.1 |
| 7,662,398 B2 | 2/2010 | Szalay et al. ............ 424/232.1 |
| 7,763,420 B2 * | 7/2010 | Stritzker et al. ............ 435/4 |
| 2001/0008025 A1 | 7/2001 | Hadlaczky et al. |
| 2001/0029023 A1 | 10/2001 | Szalay et al. |
| 2002/0054865 A1 | 5/2002 | Fujimori et al. |
| 2002/0160410 A1 | 10/2002 | Hadlaczky et al. |
| 2002/0160970 A1 | 10/2002 | Hadlaczky et al. |
| 2003/0009015 A1 | 1/2003 | Ulrich et al. |
| 2003/0031628 A1 | 2/2003 | Zhao et al. |
| 2003/0031681 A1 | 2/2003 | Mc Cart et al. |
| 2003/0033617 A1 | 2/2003 | Hadlaczky et al. |
| 2003/0044384 A1 | 3/2003 | Roberts et al. |
| 2003/0059400 A1 | 3/2003 | Szalay |
| 2003/0083293 A1 | 5/2003 | Hadlaczky et al. |
| 2003/0086906 A1 | 5/2003 | Mastrangelo et al. |
| 2003/0101480 A1 | 5/2003 | Hadlaczky et al. |
| 2003/0103941 A1 | 6/2003 | Crombleholme et al. |
| 2003/0133949 A1 | 7/2003 | Szalay et al. |
| 2003/0161788 A1 | 8/2003 | Zhao et al. |
| 2003/0165465 A1 | 9/2003 | Roberts et al. |
| 2003/0165477 A1 | 9/2003 | Balloul et al. |
| 2003/0198627 A1 | 10/2003 | Arts et al. |
| 2003/0213007 A1 | 11/2003 | Slattery et al. |
| 2003/0228261 A1 | 12/2003 | Szalay et al. |
| 2003/0228330 A1 | 12/2003 | Falkner et al. |
| 2004/0076622 A1 | 4/2004 | Studeny et al. |
| 2004/0143861 A1 | 7/2004 | Hadlaczky et al. |
| 2004/0213741 A1 | 10/2004 | Szalay et al. |
| 2004/0234455 A1 | 11/2004 | Szalay et al. |
| 2005/0025745 A1 | 2/2005 | Fujimori et al. ............ 424/93.2 |
| 2005/0031643 A1 | 2/2005 | Szalay et al. |
| 2005/0063993 A1 | 3/2005 | Schlom et al. |
| 2005/0069491 A1 | 3/2005 | Yu et al. |
| 2006/0051370 A1 | 3/2006 | Szalay et al. |
| 2007/0025981 A1 | 2/2007 | Szalay et al. |
| 2007/0202572 A1 | 8/2007 | Szalay et al. |
| 2007/0212727 A1 | 9/2007 | Szalay et al. |
| 2008/0193373 A1 | 8/2008 | Stritzker et al. ............ 424/1.17 |
| 2009/0081639 A1 | 3/2009 | Hill et al. ............ 435/5 |
| 2009/0117047 A1 | 5/2009 | Szalay et al. ............ 424/9.3 |
| 2009/0117048 A1 | 5/2009 | Szalay et al. ............ 424/9.3 |
| 2009/0117049 A1 | 5/2009 | Szalay et al. ............ 424/9.3 |
| 2009/0123382 A1 | 5/2009 | Szalay et al. ............ 424/9.6 |
| 2009/0136917 A1 | 5/2009 | Szalay et al. ............ 435/5 |
| 2009/0155287 A1 | 6/2009 | Chen et al. ............ 424/158.1 |
| 2009/0162288 A1 | 6/2009 | Chen et al. ............ 424/9.3 |
| 2009/0180955 A1 | 7/2009 | Stritzker et al. ............ 424/1.73 |
| 2009/0180987 A1 | 7/2009 | Stritzker et al. ............ 424/93.2 |
| 2010/0008946 A1 | 1/2010 | Szalay et al. ............ 424/199.1 |
| 2010/0062016 A1 | 3/2010 | Szalay et al. ............ 424/199.1 |
| 2011/0064650 A1 | 3/2011 | Szalay ............ 424/1.11 |

FOREIGN PATENT DOCUMENTS

| | | |
|---|---|---|
| DE | 44 25 382 | 8/1997 |
| EP | 0 037 441 A1 | 10/1981 |
| EP | 0 037 441 B1 | 5/1984 |
| EP | 0 861 093 | 9/1998 |
| EP | 1 020 197 | 7/2000 |
| EP | 1 146 125 | 10/2001 |
| EP | 1 281 772 A1 | 2/2003 |
| EP | 1 281 777 A1 | 2/2003 |
| EP | 1 281 767 | 5/2003 |
| EP | 1 369 491 | 12/2003 |
| EP | 1489164 | 12/2004 |
| EP | 1 254 250 | 3/2005 |
| EP | 1 512 746 | 3/2005 |
| EP | 1 526 185 | 4/2005 |
| JP | 55035004 | 3/1980 |
| JP | 09-502993 | 3/1997 |
| JP | 2000-502884 | 3/2000 |
| JP | 2000-295987 | 10/2000 |
| JP | 2002097144 | 4/2002 |
| WO | WO 84/00381 | 2/1984 |
| WO | WO 88/00617 | 1/1988 |
| WO | WO 89/11294 | 11/1989 |
| WO | WO 90/13658 | 11/1990 |
| WO | 91/07989 | 6/1991 |
| WO | WO 92/22327 | 12/1992 |
| WO | 94/10302 | 5/1994 |
| WO | 95/31105 | 11/1995 |
| WO | 96/11279 | 4/1996 |
| WO | WO 96/40238 | 12/1996 |
| WO | 97/18841 | 5/1997 |
| WO | WO 97/35997 | 10/1997 |
| WO | WO 97/40183 | 10/1997 |
| WO | WO 98/05274 | 2/1998 |
| WO | WO 98/14605 | 4/1998 |
| WO | WO 98/35695 | 8/1998 |
| WO | WO 99/30648 | 6/1999 |
| WO | 99/32646 | 7/1999 |
| WO | WO 00/23471 | 4/2000 |
| WO | 00/47237 | 8/2000 |
| WO | WO 00/69448 | 11/2000 |
| WO | WO 00/71718 | 11/2000 |
| WO | WO 00/73479 | 12/2000 |
| WO | 01/05229 | 1/2001 |
| WO | 01/12234 | 2/2001 |
| WO | 01/14579 | 3/2001 |
| WO | 01/18195 | 3/2001 |
| WO | 01/20989 | 3/2001 |
| WO | 01/24637 | 4/2001 |
| WO | 01/25399 | 4/2001 |
| WO | WO 01/48231 | 7/2001 |
| WO | 01/55444 | 8/2001 |
| WO | WO 02/071062 | 9/2002 |
| WO | 03/006069 | 1/2003 |
| WO | 03/014380 | 2/2003 |
| WO | 03/045153 A1 | 6/2003 |
| WO | 03/057007 | 7/2003 |
| WO | 03/063593 | 8/2003 |
| WO | 03/092600 | 11/2003 |
| WO | 03/102168 A1 | 12/2003 |
| WO | 03/102169 | 12/2003 |
| WO | 03/104485 A2 | 12/2003 |
| WO | WO 2004/030631 | 4/2004 |
| WO | 2004/044175 | 5/2004 |
| WO | WO 2004/069178 | 8/2004 |
| WO | 2005/047458 | 5/2005 |
| WO | 2005/057488 | 6/2005 |
| WO | 2005/072622 | 8/2005 |
| WO | PCT/US2007/15829 | 7/2007 |
| WO | PCT/US2007/22172 | 10/2007 |
| WO | WO 2008/099001 | 8/2008 |
| WO | WO 2008/100292 | 8/2008 |
| WO | WO 2009/126189 | 10/2009 |

OTHER PUBLICATIONS

Anand, A and A.E. Glatt, "Clostridium difficile infection associated with antineoplastic chemotherapy: a review," Clin Infect Dis. 17(1):109-13 (1993).
Arab et al., "Verotoxin induces apoptosis and the complete, rapid, long-term elimination of human astrocytoma xenografts in nude mice," Oncol Res. 11(1):33-9 (1999).
Arakawa et al., "Clinical trial of attenuated vaccinia virus AS strain in the treatment of advanced adenocarcinoma. Report on two cases," J Cancer Res Clin Oncol. 113(1):95-8 (1987).
ATCC Accession No. 11842.
ATCC Accession No. 11863.
ATCC Accession No. 13124.
ATCC Accession No. 15696.
ATCC Accession No. 15697.
ATCC Accession No. 15707.
ATCC Accession No. 15955.
ATCC Accession No. 17583.
ATCC Accession No. 17836.
ATCC Accession No. 19401.
ATCC Accession No. 19402.
ATCC Accession No. 19404.
ATCC Accession No. 25527.
ATCC Accession No. 25752.
ATCC Accession No. 25923.
ATCC Accession No. 27337.
ATCC Accession No. 27555.
ATCC Accession No. 29212.
ATCC Accession No. 35782.
ATCC Accession No. 3624.
ATCC Accession No. 37253.
ATCC Accession No. 393.
ATCC Accession No. 43142.
ATCC Accession No. 47054.
ATCC Accession No. 51299.
ATCC Accession No. 700057.
ATCC Accession No. 824.
ATCC Accession No. 9338.
ATCC Accession No. 9714.
ATCC Accession No. BAA-250D.
ATCC Accession No. CCL-70.
Azmi et al., "In situ localization of endogenous cytokinins during shooty tumor development on *Eucalyptus globulus* Labill," Planta 213(1):29-36 (2001).
Baker, S.J. and E.P. Reddy, "Transducers of life and death: TNF receptor superfamily and associated proteins," Oncogene 12(1):1-9 (1996).
Banerjee et al., "*Bacillus* infections in patients with cancer," Arch Intern Med. 148(8):1769-74 (1988).
Bentires-Alj et al., "Cytosine deaminase suicide gene therapy for peritoneal carcinomatosis," Cancer Gene Ther. 7(1):20-6 (2000).
Bermudes et al., "Tumor-targeted Salmonella: Highly selective delivery vectors," Adv Exp Med Biol. 465:57-63 (2000).
Beyer et al., "Oncoretrovirus and lentivirus vectors pseudotyped with lymphocytic choriomeningitis virus glycoprotein: generation, concentration, and broad host range," J Virol. 76(3):1488-95 (2002).
Biffi et al., "Antiproliferative effect of fermented milk on the growth of a human breast cancer cell line," Nutr Cancer. 28(1):93-9 (1997).
Block et al., "Gene therapy of metastatic colon carcinoma: regression of multiple hepatic metastases by adenoviral expression of bacterial cytosine deaminase," Cancer Gene Ther. 7(3):438-45 (2000).
Bodey et al., "Clostridial bacteremia in cancer patients. A 12-year experience," Cancer 67(7):1928-42 (1991).
Bogdanov et al., "Antitumour glycopeptides from *Lactobacillus bulgaricus* cell wall," FEBS Lett. 57(3):259-61 (1975).
Bogdanov et al., "Antitumor action of glycopeptides from the cell wall of *Lactobacillus bulgaricus*," Bulletin of Experimental Biology and Medicine. 84(12): 1750-1753 (1977); translated from the original Russian article: Byulleten' Éksperimental'noi Biologii I Meditsiny 84(12):709-12 (1977).
Certified English translation of Timiryasova et al., "Analysis of Reporter Gene Expression in Various Regions of the Genome of the Vaccinia Virus," Molecular Biology 27(2): 2-11 (1993).
Chang et al., "Differential apoptotic susceptibility to anti-Fas IgM and anticancer drugs in a human endometrial adenocarcinoma cell line HHUA on laminin and type I collagen," Osaka City Med J. 44(2):173-80 (1998).
Chatterjee, B.D. and C.K. Chakraborti, "Non-sporing anaerobes in certain surgical group of patients," J Indian Med Assoc. 93(9):333-5, 339 (1995).
Chen et al., "Low-dose vaccinia virus-mediated cytokine gene therapy of glioma," J Immunother. 24(I):46-57 (2001).
Clairmont et al., "Biodistribution and genetic stability of the novel antitumor agent VNP20009, a genetically modified strain of *Salmonella typhimurium*," J Infect Dis. 181(6):1996-2002 (2000).
Cole, A.M. and T. Ganz, "Human antimicrobial peptides: analysis and application," Biotechniques. 29(4):822-6, 828, 830-1 (2000).
Collins, J.L. and C.J. Wust, "Suppression of SV40 tumors after immunization with group A *Streptococcus pyogenes* and *Bordetella pertussis*," Cancer Res. 34(5):932-7 (1974).
Dang et al., "Combination bacteriolytic therapy for the treatment of experimental tumors," Proc Natl Acad Sci U S A. 98(26):15155-60 (2001).
de Lorenzo V., "Isolation and characterization of microcin E492 from *Klebsiella pneumoniae*," Arch Microbiol. 139(1):72-5 (1984).
Djeha et al., "Expression of *Escherichia coli* B nitroreductase in established human tumor xenografts in mice results in potent antitumoral and bystander effects upon systemic administration of the prodrug CB1954," Cancer Gene Ther. 7(5):721-31 (2000).
Djeha et al., Combined adenovirus—mediated nitroreductase gene delivery and CB1954 treatment: a well-tolerated therapy for established solid tumors. Mol Ther. Feb. 2001;3(2):233-40.
Duncan, J.R. and M.J. Welch, "Intracellular metabolism of indium-111-DTPA-labeled receptor targeted proteins," J Nucl Med. 34(10):1728-38 (1993).
Dunn et al., "Cancer immunoediting: from immunosurveillance to tumor escape.," Nat Immunol. 3(11):991-8 (2002).
Eliopoulos et al., "CD40 induces apoptosis in carcinoma cells through activation of cytotoxic ligands of the tumor necrosis factor superfamily," Mol Cell Biol. 20(15):5503-15 (2000).
Essbauer, S. and W. Ahne, "Viruses of lower vertebrates," J Vet Med B Infect Dis Vet Public Health. 48(6):403-75 (2001).
Farkas-Himsley et al., "The bacterial colicin active against tumor cells in vitro and in vivo is verotoxin 1," Proc Natl Acad Sci U S A. 92(15):6996-7000 (1995).
Feng et al, "The antitumor activity of a mixed bacterial vaccine against mouse hepatoma," Chinese Pharmaceutical Journal 30(7): 405-407 (1995) [Article in Chinese].
Fodor et al., "Vaccinia virus mediated p53 gene therapy for bladder cancer in an orthotopic murine model," J. Urol. 173(2):604-9 (2005).
Friedlos et al., "Three new prodrugs for suicide gene therapy using carboxypeptidase G2 elicit bystander efficacy in two xenograft models," Cancer Res. 62(6):1724-1729 (2002).
Gnant et al., "Systemic administration of a recombinant vaccinia virus expressing the cytosine deaminase gene and subsequent treatment with 5-fluorocytosine leads to tumor-specific gene espression and prolongaton of survival in mice," Cancer Res. 59(14):3396-3403 (1999).
Golstein, P., "Cell death: TRAIL and its receptors," Curr Biol. 7(12):R750-R753 (1997).
Greco et al., "Development of a novel enzyme/prodrug combination for gene therapy of cancer: horseradish peroxidase/indole-3-acetic acid," Cancer Gene Ther. 7(11):1414-20 (2000).
Gridley et al., "Evaluation of radiation effects against C6 glioma in combination with vaccinia virus-p53 gene therapy," Int J Oncol. 13(5):1093-8 (1998).
Gridley et al., "Proton radiation and TNF-α/Bax gene therapy for orthotopic C6 brain tumor in Wistar rats," Technol Cancer Res Treat. 3(2):217-27 (2004).
Grote et al., "Live attenuated measles virus induces regression of human lymphoma xenografts in immunodeficient mice," Blood 97(12):3746-54 (2001).
Hall et al., "In vitro efficacy of transferrin-toxin conjugates against glioblastoma multiforme," J Neurosurg. 76(5):838-44 (1992).

Hall et al., "In vivo efficacy of intrathecal transferrin-*Pseudomonas* exotoxin A immunotoxin against LOX melanoma," Neurosurgery 34(4):649-55; discussion 655-6 (1994).

Hansen, R.M. and J.A. Libnoch, "Remission of chronic lymphocytic leukemia after smallpox vaccination," Arch Intern Med. 138(7):1137-8 (1978).

Harrison et al., "Gene-modified PA1-STK cells home to tumor sites in patients with malignant pleural mesothelioma," Ann Thorac Surg. 70(2):407-11 (2000).

Hasegawa et al., "Avoidance of bone marrow suppression using A-5021 as a nucleoside analog for retrovirus-mediated herpes simplex virus type I thymidine kinase gene therapy,," Cancer Gene Ther. 7(4):557-62 (2000).

Herrlinger et al., "Neural precursor cells for delivery of replication-conditional HSV-1 vectors to intracerebral gliomas," Mol Ther. 1(4):347-57 (2000).

Hetz et al., "Microcin E492, a channel-forming bacteriocin from *Klebsiella pneumoniae*, induces apoptosis in some human cell lines," Proc Natl Acad Sci U S A. 99(5):2696-701 (2002).

Hostanska et al., "Aqueous ethanolic extract of St. John's wort (*Hypericum perforatum* L.) induces growth inhibition and apoptosis in human malignant cells in vitro," Pharmazie 57(5):323-31 (2002).

Hsueh et al., "Outbreak of *Pseudomonas fluorescens* bacteremia among oncology patients," J Clin Microbiol. 36(10):2914-7 (1998).

Huang et al., "Impact of liver P450 reductase suppression on cyclophosphamide activation, pharmacokinetics and antitumoral activity in a cytochrome P450-based cancer gene therapy model," Cancer Gene Ther. 7(7):1034-42 (2000).

Ianaro et al., "A nitric oxide synthase inhibitor reduces inflammation, down-regulates inflammatory cytokines and enhances interleukin-10 production in carrageenin-induced oedema in mice," Immunology. 82(3):370-5 (1994).

Jiang et al. "Apoptosis in human hepatoma cell lines by chemotherapeutic drugs via Fas-dependent and Fas-independent pathways," Hepatology. 29(1):101-10 (1999).

Johnson et al., "Improved tumor-specific immunotoxins in the treatment of CNS and leptomeningeal neoplasia," J Neurosurg. 70(2):240-8 (1989).

Jordan et al., "Melanocyte-Directed enzyme prodrug therapy (MDEPT): development of second generation prodrugs for targeted treatment of malignant melanoma," Bioorg Med Chem. 9(6):1549-58 (2001).

Kaklij et al., "Antitumor activity of *Streptococcus thermophilus* against fibrosarcoma: role of T-cells,"Cancer Lett. 56(1):37-43 (1991).

Kaklij, G.S. and S.M. Kelkar, "Tumor-specific transplantation resistance in mice after treatment of initial tumors with *Streptococcus thermophilus*," Microbiol Immunol. 40(1):55-8 (1996).

Kammertoens et al., "Combined chemotherapy of murine mammary tumors by local activation of the prodrugs ifosfamide and 5-fluorocytosine," Cancer Gene Ther. 7(4):629-36 (2000).

Kan et al., "Direct retroviral delivery of human cytochrome P450 2B6 for gene-directed enzyme prodrug therapy of cancer," Cancer Gene Ther. 8(7):473-82 (2001).

Kato et al., "Antitumor activity of *Lactobacillus casei* in mice," Gann. 72(4):517-23 (1981).

Kato et al., "Correlation between increase in Ia-bearing macrophages and induction of T cell-dependent antitumor activity by *Lactobacillus casei* in mice," Cancer Immunol Immunother. 26(3):215-21 (1988).

Kawamura et al., "Expression of *Escherichia coli* uracil phosphoribosyltransferase gene in murine colon carcinoma cells augments the antitumoral effect of 5-fluorouracil and induces protective immunity," Cancer Gene Ther. 7(4):637-43 (2000).

Kelkar et al., "Antitumor activity of lactic acid bacteria on a solid fibrosarcoma, sarcoma-180 and Ehrlich ascites carcinoma, " Cancer Lett. 42(l-2):73-7 (1988).

Ketlinsky et al., "[Mechanism of the anti-tumoral effect of the blastolysin fraction isolated from *Lactobacillus bulgaricus*]," Vopr Onkol. 33(3):51-6 (1987) [Article in Russian].

Kimura et al., "Selective localization and growth of Bifidobacterium bifidum in mouse tumors following intravenous administration," Cancer Res. 40(6):2061-8 (1980).

Kohwi et al., "Antitumor effect of Bifidobacterium infantis in mice," Gann. 69(5):613-8 (1978).

Kokkinakis et al., "Effect of long-term depletion of plasma methionine on the growth and survival of human brain tumor xenografts in athymic mice," Nutr Cancer. 29(3):195-204 (1997).

Kopylova-Sviridova et al., "Transient expression assay in a baculovirus system using firefly luciferase gene as a reporter," Virus Genes. 6(4):379-86 (1992).

Koyama et al., "Combined suicide gene therapy for human colon cancer cells using adenovirus-mediated transfer of *Escherichia coli* cytosine deaminase gene and *Escherichia coli* uracil phosphoribosyltransferase gene with 5-fluorocytosine," Cancer Gene Ther. 7(7):1015-22 (2000).

Kunik et al., "Genetic transformation of HeLa cells by Agrobacterium," Proc Natl Acad Sci U S A. 98(4):1871-6 (2001).

Lachmann, R.H. and S. Efstathiou, "Gene transfer with herpes simplex vectors," Curr Opin Mol Ther. 1(5):622-32 (1999).

Lamensans et al., "Enhancement of immunity against murine syngeneic tumors by a fraction extracted from non-pathogenic mycobacteria," Proc Natl Acad Sci U S A. 72(9):3656-60 (1975).

Lammertyn et al., "Evaluation of a novel subtilisin inhibitor gene and mutant derivatives for the expression and secretion of mouse tumor necrosis factor alpha by *Streptomyces lividans*," Appl Environ Microbiol. 63(5):1808-13 (1997).

Li et al., "Enzyme/prodrug gene therapy approach for breast cancer using a recombinant adenovirus expressing *Escherichia coli* cytosine deaminase," Cancer Gene Ther. 4(2):113-7 (1997).

Liu et al., "Anticancer efficacy of systemically delivered anaerobic bacteria as gene therapy vectors targeting tumor hypoxia/necrosis," Gene Ther. 9(4):291-6 (2002).

Martino et al., "Bacteremia due to glucose non-fermenting gram-negative bacilli in patients with hematological neoplasias and solid tumors," Eur J Clin Microbiol Infect Dis. 15(7):610-5 (1996).

McIntosh et al., "A probiotic strain of *L. acidophilus* reduces DMH-induced large intestinal tumors in male Sprague-Dawley rats," Nutr Cancer. 35(2):153-9 (1999).

Meadows et al., "Some biological properties and an in vivo evaluation of tyrosine phenol-lyase on growth of B-16 melanoma," Cancer Res. 36(1):167-7 (1976).

Meck et al., "A virus-directed enzyme prodrug therapy approach to purging neuroblastoma cells from hematopoietic cells using adenovirus encoding rabbit carboxylesterase and CPT-11," Cancer Res. 61(13):5083-9 (2001).

Micheau et al., "Sensitization of cancer cells treated with cytotoxic drugs to fas-mediated cytotoxicity," J Natl Cancer Inst. 89(11):783-9 (1997).

Michl et al., "Claudin-4: a new target for pancreatic cancer treatment using *Clostridium perfringens* enterotoxin," Gastroenterology 121(3):678-84 (2001).

Miki et al., "Methioninase gene therapy of human cancer cells is synergistic with recombinant methioninase treatment," Cancer Res. 60(10):2696-702 (2000).

Milbrandt, E., "A novel source of enterococcal endocarditis," Clin Cardiol. 21(2):123-6 (1998).

Minton et al., "Chemotherapeutic tumour targeting using clostridial spores," FEMS Microbiol Rev. 17(3):357-64 (1995).

Mirzadeh et al., "Radiometal labeling of immunoproteins: covalent linkage of 2-(4-isothiocyanatobenzyl)diethylenetriaminepentaacetic acid ligands to immunoglobulin," Bioconjug Chem. 1(1):59-65 (1990).

Mizutani, T and T. Mitsuoka, "Inhibitory effect of some intestinal bacteria on liver tumorigenesis in gnotobiotic C3H/He male mice," Cancer Lett. 11(2):89-95 (1980).

Mizutani et al., "Doxorubicin sensitizes human bladder carcinoma cells to Fas-mediated cytotoxicity," Cancer. 79(6):1180-9 (1997).

Mizutani et al., "Sensitization of human bladder cancer cells to Fas-mediated cytotoxicity by cis-diamminedichloroplatinum (II)," J Urol. 160(2):561-70 (1998).

Mohr et al., "Rabbit cytochrome P450 4B1: A novel prodrug activating gene for pharmacogene therapy of hepatocellular carcinoma," Cancer Gene Ther. 7(7):1008-14 (2000).

Moolten, F.L., "Tumor chemosensitivity conferred by inserted herpes thymidine kinase genes: paradigm for a prospective cancer control strategy," Cancer Res. 46(10):5276-81 (1986).

Mukherjee et al., "Replication-restricted vaccinia as a cytokine gene therapy vector in cancer: persistent transgene expression despite antibody generation," Cancer Gene Ther. 7(5):663-70 (2000).

Murosaki et al., "Antitumor effect of heat-killed *Lactobacillus plantarum* L-137 through restoration of impaired interleukin-12 production in tumor-bearing mice," Cancer Immunol Immunother. 49(3):157-64 (2000).

Myklebust et al., "Eradication of small cell lung cancer cells from human bone marrow with immunotoxins," Cancer Res. 53(16):3784-8 (1993).

Nakamura et al., "Induction of apoptosis in HL60 leukemic cells by anticancer drugs in combination with anti-Fas monoclonal antibody," Anticancer Res. 17(1A):173-9 (1997).

Nakao, H. and T. Takeda, "*Escherichia coli* Shiga toxin," J Nat Toxins. 9(3):299-313 (2000).

Nauciel, C. and A.F. Goguel, "Inhibition of tumor growth by the peptidoglycan from *Bacillus megaterium*," J Natl Cancer Inst. 59(6):1723-6 (1977).

Nuyts et al., "Clostridium spores for tumor-specific drug delivery," Anticancer Drugs. 13(2):115-25 (2002).

O'Brien et al., "Shiga toxin: biochemistry, genetics, mode of action, and role in pathogenesis," Curr Top Microbiol Immunol. 180:65-94 (1992).

O'Mahony et al., "Probiotic impact on microbial flora, inflammation and tumour development in IL-10 knockout mice," Aliment Pharmacol Ther. 15(8):1219-25 (2001).

Paul et al., "Redirected cellular cytotoxicity by infection of effector cells with a recombinant vaccinia virus encoding a tumor-specific monoclonal antibody," Cancer Gene Ther. 7(4):615-23 (2000).

Pawelek et al., "Tumor-targeted *Salmonella* as a novel anticancer vector," Cancer Res. 57(20):4537-4544 (1997).

Pekhov AA, Zhukova OS, Ivanova TP, Zanin VA, Dobrynin IaV. [Cytotoxic effect of methionine-gamma-lyase on neoplastic cells in culture] Biull Eksp Biol Med. 95(5):87-8 (1983) [Article in Russian].

Picot et al., "*Pseudomonas fluorescens* as a potential pathogen: adherence to nerve cells," Microbes Infect. 3(12):985-95 (2001).

Rezmer et al., "Identification and localization of transformed cells in *Agrobacterium tumefaciens*—induced plant tumors," Planta. 209(4):399-405 (1999).

Saito, H. and T. Watanabe T., "Effects of a bacteriocin from *Mycobacterium smegmatis* on BALB/3T3 and simian virus 40-transformed BALB/c mouse cells," Microbiol Immunol. 25(1):13-22 (1981).

Schempp et al., "Inhibition of tumour cell growth by hyperforin, a novel anticancer drug from St. John's wort that acts by induction of apoptosis," Oncogene 21(8):1242-50 (2002).

Schirrmacher et al., "Antitumor effects of Newcastle Disease Virus in vivo: local versus systemic effects," Int J Oncol. 18(5):945-52 (2001).

Schoen et al., "Bacterial delivery of functional messenger RNA to mammalian cells," Cell Microbiol. 7(5):709-24 (2005).

Schroder, J.M., "Epithelial antimicrobial peptides: innate local host response elements," Cell Mol Life Sci. 56(1-2):32-46 (1999).

Schuller et al., "Investigation and management of *Clostridium difficile* colonisation in a paediatric oncology unit.," Arch Dis Child. 72(3):219-222 (1995).

Sekine et al., "Analysis of antitumor properties of effector cells stimulated with a cell wall preparation (WPG) of *Bifidobacterium infantis*," Biol Pharm Bull. 18(1):148-53 (1995).

Sekine et al., "A new morphologically characterized cell wall preparation (whole peptidoglycan) from *Bifidobacterium infantis* with a higher efficacy on the regression of an established tumor in mice," Cancer Res. 45(3):1300-7 (1985).

Sharma et al., "Death the Fas way: regulation and pathophysiology of CD95 and its ligand," Pharmacol Ther. 88(3):333-47 (2000).

Shimizu et al, "Significance of priming of hosts with virus in the tumor-specific immunotherapy model utilizing virus-reactive helper T cell activity," Nippon Gan Chiryo Gakkai Shi. May 20, 1989;24(5):1007-14. [Article in Japanese].

Shimizu et al., "Immunotherapy of tumor-bearing mice utilizing virus help," Cancer Immunol Immunother. 27(3):223-7 (1988).

Simon et al., "Surveillance for nosocomial and central line-related infections among pediatric hematology-oncology patients," Infect Control Hosp Epidemiol. 21(9):592-6 (2000).

Simonds et al., "Deoxyribonucleic acid hybridization among strains of lactobacilli," J Bacteriol. 107(1):382-4 (1971).

Sivanandham et al., "Colon cancer cell vaccine prepared with replication-deficient vaccinia viruses encoding B7.1 and interleukin-2 induce antitumor response in syngeneic mice," Cancer Immunol Immunother 46(5):261-7 (1998).

Smyth et al., "Bovine enterovirus as an oncolytic virus: foetal calf serum facilitates its infection of human cells," Int J Mol Med. 10(1):49-53 (2002).

Soby et al., "Catabolite-repressor-like protein regulates the expression of a gene under the control of the *Escherichia coli* lac promoter in the plant pathogen *Xanthomonas campestris* pv. *Campestris*," Appl Microbiol Biotechnol. 46(5-6):559-61 (1996).

Spooner et al., "In suicide gene therapy, the site of subcellular localization of the activating enzyme is more important than the rate at which it activates prodrug," Cancer Gene Ther. 7(10):1348-56 (2000).

Steffens et al., "Enhanced green fluorescent protein fusion proteins of herpes simplex virus type 1 thymidine kinase and cytochrome P450 4B1: applications for prodrug-activating gene therapy," Cancer Gene Ther. 7(5):806-12 (2000).

Tanaka et al, "Preliminary evaluation of intratumoral injection of a *Streptococcus pyrogenes* preparation in patients with malignant brain tumors," Cancer 46(7):1688-94 (1980).

Tartaglia et al., "NYVAC: a highly attenuated strain of vaccinia virus," Virology 188(1):217-32 (1992).

Thatcher et al., "The potential of acetaminophen as a prodrug in gene-directed enzyme prodrug therapy," Cancer Gene Ther. 7(4):521-5 (2000).

Theys et al., "Specific targeting of cytosine deaminase to solid tumors by engineered *Clostridium acetobutylicum*," Cancer Gene Ther. 8(4):294-7 (2001).

Theys et al., "Stable *Escherichia coli-Clostridium acetobutylicum* shuttle vector for secretion of murine tumor necrosis factor alpha," Appl Environ Microbiol. 65(10):4295-4300 (1999).

Tietze et al., "Highly selective glycosylated prodrugs of cytostatic CC-1065 analogues for antibody-directed enzyme tumor therapy," Chembiochem. 2(10):758-65 (2001).

Timiryasova et al., "Radiation enhances the anti-tumor effects of vaccinia-p53 gene therapy in glioma," Technol Cancer Res Treat. 2(3):223-35 (2003).

Toso et al, "Phase I study of the intravenous administration of attenuated *Salmonella typhimurium* to patients with metastatic melanoma," J Clin Oncol. 20(1):142-52 (2002).

Ullrich C.I. and R. Aloni, "Vascularization is a general requirement for growth of plant and animal tumours," Journal of Experimental Botany 51(353):1951-60 (2000).

Webley et al., "Measurement of the critical DNA lesions produced by antibody-directed enzyme prodrug therapy (ADEPT) in vitro, in vivo and in clinical material," Br J Cancer. 84(12):1671-6 (2001).

Weedon et al., "Sensitisation of human carcinoma cells to the prodrug CB1954 by adenovirus vector-mediated expression of *E. coli* nitroreductase," Int J Cancer. 86(6):848-54 (2000).

Wehl et al., "Trends in infection morbidity in a pediatric oncology ward, 1986-1995," Med Pediatr Oncol. 32(5):336-43 (1999).

Westphal et al., "The nitroreductase/CB1954 combination in Epstein-Barr virus-positive B-cell lines: induction of bystander killing in vitro and in vivo," Cancer Gene Ther. 7(1):97-106 (2000).

Wollowski et al., "Protective role of probiotics and prebiotics in colon cancer," Am J Clin Nutr. 73 (2 Suppl):451S-455S (2001).

Wu et al., "Biological purging of breast cancer cells using an attenuated replication-competent herpes simplex virus in human hematopoietic stem cell transplantation," Cancer Res. 61(7):3009-15 (2001).

Yamamoto et al., "Production of L-forms of *Streptococcus pyogenes* and their antitumor effects," Jpn J Exp Med. 50(5):383-8 (1980).

Yazawa et al., "*Bifidobacterium longum* as a delivery system for cancer gene therapy: Selective localization and growth in hypoxic tumors," Cancer Gene Ther. 7(2):269-74 (2000).

Yazawa et al., *Bifidobacterium longum* as a delivery system for gene therapy of chemically induced rat mammary tumors. Breast Cancer Res Treat. 66(2):165-70 (2001).

Yu et al.,. Visualization of tumors and metastases in live animals with bacteria and vaccinia virus encoding light-emitting proteins, Nature Biotechnology 22(3):313-320 (2004).

Zambryski et al., "Tumor induction by *Agrobacterium tumefaciens*: analysis of the boundaries of T-DNA," J Mol Appl Genet. 1(4):361-70 (1982).

Zheng et al., "Tumor amplified protein expression therapy: *Salmonella* as a tumor-selective protein delivery vector," Oncology Research 12(3):127-135 (2000).

zur Hausen, H., Papillomaviruses and cancer: from basic studies to clinical application. Nature Reviews Cancer 2(5):342-50 (2002).

Abe et al., "Peripheral blood fibrocytes:differentiation pathway and migration to wound sites," Journal of Immunology 166:7556-7562 (2001).

Ballas et al., "Adult bone marrow stem cells for cell and gene therapies: implications for greater use," Journal of Cellular Biochemistry. Supplement 38:20-28 (2002).

Bonadio, J., "Genetic approaches to tissue repair," Annals of the New York Academy of Sciences 961:58-60 (2002).

Bulte et al., "Magnetodendrimers allow endosomal magnetic labeling and in vivo tracking of stem cells," Nature Biotechnology, 19(12):1141-1147 (2001).

Burt et al., "Treatment of autoimmune disease by intense immunosuppressive conditioning and autologous hemotopoietic stem cell transplantation," Blood 92(10):3505-3514 (1998).

Byun et al., "Myocardial injury-induced fibroblast proliferation facilitates retroviral-mediated gene transfer to the rat heart in vivo," Journal of Gene Medicine 2(1):2-10 (2000).

Chen, Y., "Orthopedic applications of gene therapy," Journal of Orthopaedic Science 6:199-207, (2000).

Chen et al., "Therapeutic benefit of intravenous administration of bone marrow stromal cells after cerebral ischemia in rats," Stroke 32:1005-1011 (2001).

Chernajovsky et al., "Fighting cancer with oncolytic viruses," BMJ : British Medical Journal 332(7534):170-172 (2006).

Costa, G., et al., "Adoptive immunotherapy of experimental autoimmune encephalomyelitis via T cell delivery of the IL-12 p40 subunit," Journal of Immunology, 167(4):2379-2387 (2001).

Crombleholme, T., "Adenoviral-mediated gene transfer in wound healing," Wound Repair and Regeneration 8(6):460-472, (2000).

Cupp, C. and D. Bloom, "Gene therapy, electroporation, and the future of wound-healing therapies," Facial Plastic Surgery 18(1):53-57 (2002).

Deodato et al. "Recombinant AAV vector encoding human VEGF165 enhances wound healing" Gene Therapy 9:777-785 (2002).

Eming, S., et al., "Gene therapy for tissue repair: approaches and prospects," British Journal of Plastic Surgery 50(7):491-500 (1997).

Falk et al., "Improved adherence of genetically modified endothelial cells to small-diameter expanded polytetrafluoroethylene grafts in a canine model," Journal of Vascular Surgery 902-908.

Fox et al., "Anaerobic bacteria as a delivery system for cancer gene therapy: in vitro activation of 5," Gene Therapy 3:173-178 (1996).

Fox et al., Erratum to "Anaerobic bacteria as a delivery system for cancer gene therapy: in vitro activation of 5," Gene Therapy 3:741 (1996).

Gautam et al., "Delivery systems for pulmonary gene therapy," American Journal of Respiratory Medicine 1(1):35-46 (2002).

Ghivizzani, S., et al., "Direct adenovirus-mediated gene transfer of interleukin 1 and tumor necrosis factor alpha soluble receptors to rabbit knees with experimental arthritis has local and distal antiarthritic effects," Proceedings of the National Academy of Sciences of the United States of America 95(8):4613-4618 (1998).

Ghivizzani, S., et al., "Direct retrovirus-mediated gene transfer to the synovium of the rabbit knee: implications for arthritis gene therapy," Gene Therapy 4(9):977-982 (1997).

Gordon, E., et al., "Lesion-targeted injectable vectors for vascular restenosis," Human Gene Therapy, 12:1277-1287, (2001).

Gura, "Systems for identifying new drugs are often faulty," Science 278:1041-1042 (1997).

Hall, F., et al., "Targeting retroviral vectors to vascular lesions by genetic engineering of the MoMLV gp70 envelope protein," Human Gene Therapy, 8:2183-2192, (1997).

Iwaguro et al., "Endothelial progenitor cell vascular endothelial growth factor gene transfer for vascular regeneration," Circulation 105:732-738 (2002).

Kelland et al. "Of mice and men: values and liabilities of the athymic nude mouse model in anticancer drug development," European Journal of Cancer 40:827-836 (2004).

Kerbel et al., "Human tumor xenografts as predictive preclinical models for anticancer drug activity in humans," Cancer Biology & Therapy 2:4 suppl. 1 S134-S139 (2003).

Kim et al. "A tale of two trials: selectively replicating herpesviruses for brain tumors," Gene Therapy 7(10):815-816 (2000).

Kohler et al., "Continuous cultures of fused cells secreting antibody of predefined specificity," Nature 256:495-497 (1975).

Kotton et al., "Bone marrow-derived cells as progenitors of lung alveolar epithelium," Development 128:5181-5188 (2001).

Larocca et al., "Gene transfer to mammalian cells using genetically targeted filamentous bacteriophage," FASEB Journal 13:727-734 (1999).

Lee et al., "Regeneration of hyaline cartilage by cell-mediated gene therapy using transforming growth factor beta 1-producing fibroblasts" Human Gene. Ther. 12(14):1805-1813 (2001).

Liechty, K., et al., "Adenoviral-mediated overexpression of platelet-derived growth factor-B corrects ischemic impaired wound healing," Journal of Investigative Dermatology 113(3):375-383 (1999).

Lindsey et al., "Modified cold virus kills colon cancer," Lancet Oncology 3(5):264 (2002).

Lock, C., et al., "The role of TNFalpha and lymphotoxin in demyelinating disease," Annals of the Rheumatic Diseases 58 Suppl 1:I121-I128 (1999).

Lutz et al., "Independent and tight regulation of transcriptional units in *Escherichia coli* via the LacR/O, the TetR/O and AraC/I1-I2 regulatory elements," Nucleic Acids Research 25:1203-1210 (1997).

Marti et al., "PBSC autotransplant for inflammatory bowel disease (IBD):a case of *Uulcerative colitis*," Bone Marrow Transplantation 28:109-113 (2001).

McCluskie et al., "Route and Method of Delivery of DNA Vaccine Influence Immune Responses in Mice and Non-Human Primates" Mol. Med. 5:287-300 (1999).

Meuli, M., et al., "Efficient gene expression in skin wound sites following local plasmid injection," Journal of Investigative Dermatology 116(1):131-135 (2001).

Moats et al., "A 'smart' magnetic resonance imaging agent that reports on specific enzymatic activity," Angewandte Chemie 36(7):726-728 (1997).

Musso et al., "Crohn's disease complicated by relapsed extranodal Hodgkin's lymphoma: prolonged complete remission after unmanipulated PBPC autotransplant" Bone Marrow Transplantation 26:921-923 (2000).

Okuma et al., "Reinsertion of stimulated nucleus pulposus cells retards intervertebral disk degeneration: an in vitro and in vivo experimental study," Journal of Orthopaedic Research 18(6):988-997 (2000).

Orlic et al., "Bone marrow cells regenerate infarcted myocardium," Nature 410:701-705 (2001).

Parikh et al., "Endothelial cell delivery for cardiovascular therapy," Advanced drug delivery reviews 42(1-2):139-161 (2000).

Parks, E., et al., "Transient gene transfer of IL-12 regulates chemokine expression and disease severity in experimental arthritis," Journal of Immunology 160(9):4615-4619 (1998).

Pfeifer et al., "Gene Therapy: Promises and Problems," Annual Review of Genomics and Human Genetics 2:177-211 (2001).

Rosengart, T., et al., "Six-month assessment of a phase I trial of angiogenic gene therapy for the treatment of coronary artery disease using direct intramyocardial administration of an adenovirus vector expressing the VEGF121 cDNA," Annals of Surgery 230(4):466-470; discussion 470-472 (1999).

Rubanyi et al., "The future of human gene therapy," Molecular Aspects of Medicine 22:113-142 (2001).

Schaffer, D., "Genetic approaches to tissue repair," Annals of the New York Academy of Sciences 961:68-70 (2002).

Spencer, B., et al., "Herpes simplex virus-mediated gene delivery to the rodent visual system," Investigative Opthalmology & Visual Science 41(6):1392-1401 (2000).

Sugaya et al., "Stem cell strategies for neuroreplacement therapy in Alzheimer's disease," Medical Hypotheses 57(6):697-700 (2001).

Wahl et al., "Improved Radioimaging and Tumor localization with Monoclonal F(ab')2," Journal of Nuclear Medicine 24:316-325 (1983).

Wedderburn et al., "Autologous stem cell transplantation for paediatric-onset polyarteritis nodosa: changes in autoimmune phenotype in the context of reduced diversity of the T- and B-cell repertoires, and evidence for reversion from the CD45RO+ to RA+ phenotype," Rheumatology 40:1299-1307 (2001).

Willenborg, D., "Cytokines and murine autoimmune encephalomyelitis: inhibition or enhancement of disease with antibodies to select cytokines, or by delivery of exogenous cytokines using a recombinant vaccinia virus system," Scandinavian Journal of Immunology 41(1):31-41 (1995).

Yang, W., et al., "sFlt-1 gene-transfected fibroblasts: a wound-specific gene therapy inhibits local cancer recurrence," Cancer Research 61(21):7840-7845 (2001).

"WHO Collaborating Centre for Orthopoxvirus Diagnosis and Repository for Variola Virus Strains and DNA," VECTOR: Ministry of Public Health and Social Development of Russian Federation, State Research Center of Virology and Biotechnology http://www.vector.nsc.ru/DesktopDefault.aspx?lcid=9&tabid=294&tabindex=1 (accessed Sep. 12, 2005).
"A New Way to Kill Cancer: SLU Research Shows Viruses can destroy lung, colon tumors," Science Daily: Your link to the latest research news http://www.sciencedaily.com/releases/2004/05/040517071951.htm (accessed on May 17, 2004).
Advani et al., "Replication-competent, Nonneuroinvasive Genetically Engineered Herpes Virus is Highly Effective in the Treatment of Therapy-resistant Experimental Human Tumors," Cancer Research 59: 2055-2058 (1999).
Altenbrunn et al., "Scintographic Tumor Localization in Mice with Radioiodinated Anti-*Clostridium* Antibodies," Int. J. Nucl. Med. Biol. 8(1): 90-93 (1981).
Bennett et al., "Positron emission tomography imaging for herpes virus infection: Implications for oncolytic viral treatments of cancer," Nature Med 7(7): 859-863 (2001).
Berger, F. and S.S. Gambhir, "Recent advances in imaging endogenous or transferred gene expression utilizing radionuclide technologies in living subjects," Breast Cancer Research 3: 28-35 (2001).
Blasberg, R.G. and J.G. Tjuvajev, "Herpes simplex virus thymidine kinase as a marker/reporter gene for PET imaging of gene therapy," Q J Nucl Med 43(2): 163-169 (1999).
Boland et al., "Adenovirus-mediated Transfer of the Thyroid Sodium/Iodide Symporter Gene into Tumors for a Targeted Radiotherapy," Cancer Research 60: 3484-3492 (2000).
Bonnekoh et al., "Adenoviral-Mediated Herpes Simplex Virus-Thymidine Kinase Gene Transfer in Vivo for Treatment of Experimental Human Melanoma," J .Invest. Dermatol. 106(6): 1163-1168 (1996).
Brockstedt et al., "Development of Anti-tumor Immunity against a Non-immunogenic Mammary Carcinoma through in Vivo Somatic GM-CSF, IL-2, and HSVtk Combination Gene Therapy," Mol. Ther. 6(5): 627-636 (2002).
Certified English translation of abstract for Aksac S., "[Antibody formation against *Agrobacterium tumefaciens* in patients with various cancers]," Turk Hij Tecr Biyol Derg. 34(1-2):48-51 (1974) [Article in Italian].
Certified English translation of journal article for Al'tshtein [Altshteyn] et al., "[Isolation of a recombinant vaccinia virus based on the LIVP strain inducing the surface antigen of the hepatitis B virus]," Dokl Akad Nauk SSSR. 285(3):696-9 (1985) [Article in Russian].
Chaudhuri et al., "Light-based imaging of green fluorescent protein-positive ovarian cancer xenografts during therapy," Gynecol. Oncol. 82(3): 581-589 (2001).
Chen B et al., "Evaluation of Cytokine Toxicity Induced by Vaccinia Virus-mediated IL-2 and IL-2 Antitumor Immunotherapy," Cytokine (2001) 15(61):305-314.
Derwent English abstract for Japanese Patent Publication JP 55035004, published Feb. 3, 1987, entitled, "Cellular immuno-potentiator—contg. Vaccinia attenuated virus showing no infectivity to man or rabbit and has lost humoral immunity," Derwent Accession No. 2512008.
Fabricius et al., "Quantitative investigations into the elimination of in vitro-obtained spores of the non-pathogenic *Clostridium butyricum* strain CNRZ 528, and their persistence in organs of different species following intravenous spore administration," Res. Microbiol. 144: 741-753 (1993).
Francis et al., "Monitoring bioluminescent *Staphyloccus aureus* infections in living mice using a novel *lux*ABCDE construct," Infection and Immunity 68(6): 3594-3600 (2000).
Gambhir et al., "Imaging transgene expression with radionuclide imaging technologies," Neoplasia 2(1-2): 118-138 (2000).
Gnant et al., "Regional *Versus* Systemic Delivery of Recombinant Vaccinia Virus as Suicide Gene Therapy for Murine Liver Metastases," Annals of Surgery 230(3): 352-361 (1999).
Gnant et al., "Sensitization of tumor necrosis factor α-resistant human melanoma by tumor-specific in vivo transfer of the gene encoding endothelial monocyte-activating polypeptide II using recombinant vaccinia virus," Cancer Research 59: 4668-4674 (1999).
Hamblin et al., "Rapid control of wound infections by targeted photodynamic therapy monitored by in vivo bioluminescence imaging," Photochemistry and Photobiology 75(1): 51-57 (2002).
Hansen et al., "Assessment of GFP fluorescence in cells of *Streptococcus gordonii* under conditions of low pH and low oxygen concentration," Microbiology 147: 1383-1391 (2001).
Hasegawa et al., "In vivo tumor delivery of the green fluorescent protein gene to report future occurrence of metastasis," Cancer Gene Therapy 7: 1336-1340 (2000).
Hatta, M., "Antitumor mechanisms of *Eubacterium lentum* and it components," Asian Pacific Journal of Allergy and Immunology 13: 129-137 (1995).
Hiller et al., "Characterization of Intracellular and Extracellular Vaccinia Virus Variants: $N_1$Isonicotinoyl-$N_2$-3-Methyl-4-Chlorobenzoylhydrazine Interferes with Cytoplasmic Virus Dissemination and Release," Journal of Virology 39(3): 903-913 (1981).
Ianaro et al., "Expression of TGF-β in attenuated *Salmonella typhimurium*: oral administration leads to the reduction of inflammation, II-2 and IFN-γ, but enhancement of IL-10, in carrageein-induced oedema in mice," Immunology 84:8-15 (1995).
Jacobs et al., "Positron Emission Tomography—based Imaging of Transgene Expression Mediated by Replication-conditional, Oncolytic Herpes Simplex Virus Type I Mutant Vectors in Vivo," Cancer Research 61: 2983-2995 (2001).
Jain, R.K. and N. S. Forbes, "Can engineered bacteria help control cancer," Proc. Natl. Acad. Sci. USA 98(26): 14748-14750 (2001).
Joklik, W.K., "The Purification of Four Strains of Poxviruses," Virology 18:9-18 (1962).
Kaplitt et al.,, "Mutant herpes simplex virus induced regression of tumors growing in immunocompetent rats," J. Neurooncol 19(2): 137-147 (1994).
Kirn, D.H. and F. McCormick, "Replicating viruses as selective cancer therapeutics," Mol Med Today 2(12): 519-527 (1996).
Kutinova et al., "Search for optimal parent for recombinant vaccinia virus vaccines. Study of three vaccinia virus vaccinal strains and several virus lines derived from them," Vaccine 13(5): 487-493 (1995).
Lattime et al., "In Situ Cytokine Gene Transfection Using Vaccinia Virus Vectors," Semin Oncol 23(1): 88-100 (1996).
Mackenzie et al., "Human mesenchymal stem cells persist, demonstrate site-specific multipotential differentiation, and are present in sites of wound healing and tissue regeneration after transplantation into fetal sheep," Blood Cells, Molecules, and Diseases 27(3): 601-604 (2001).
McCart et al., "Oncolytic Vaccinia Virus Expressing the Human Somatostatin Receptor SSTR2: Molecualr Imaging after Systemic Delivery Using $^{111}$In-Pentetreotide," Molecular Therapy 10(3): 553-61 (2004).

Meyer et al., "Mapping of deletions in the genome of the highly attenuated vaccinia virus MVA and their influence on virulence," Journal of General Virology 72(Pt 5): 1031-1038 (1991).

Morinaga et al., "Antitumor activity and its properties of *Eubacterium lentum*," Jpn. J. Cancer Res. (Gann) 79: 117-124 (1988).

Muravlev et al., "Protective activity of vaccinia virus envelope proteins isolated with the use of nonionic detergents," Voprosy Virusologii 40(4): 154-8 (1995) ) [article in Russian, English summary on last page of article].

Netesova et al., "Structural and functional studies of the *Hind*III-I-Genome Fragment of Vaccinia virus Strain L-IVP," Mol Biol (Mosk.) Nov.-Dec.; 25(6): 1526-32 (1991) ) [article in Russian, English summary on last page of article].

Norton et al., "Expression of Secreted Platelet-Derived Growth Factor-B by Recombinant Nonreplicating and Noncytopathic Vaccinia Virus," Annals of Surgery 224(4):555-562 (1996).

Overwijk et al., "Vaccination with a recombinant vaccinia virus enclding a 'self' antigen induces autoimmune vitiligo and tumor cell destruction in mice: Requirement for $CD4^+$ T lymphocytes," Proc. Natl. Acad. Sci. USA 96: 2982-2987 (1999).

Pak et al., "Cloning of the growth factor gene from vaccinia virus LIVP strain in *Escherichia coli* cells," Mol Gen Mikrobiol Virusol Sep.-Oct.; (9-10):19-21 (1992) ) [article in Russian, English summary on last page of article].

Pan et al., "Regression of Established B16F10 Melanoma with a Recombinant *Listeria monocytogenes* Vaccine," Cancer Research 59:5264-5269 (1999).

Peplinski et al., "In vivo gene therapy of a murine pancreas tumor with recombinant vaccinia virus encoding human interleukin-1beta," Surgery 118:185-191 (1995).

Phillips-Jones, M.K., "Bioluminescence (*lux*) expression in the anaerobe *Clostridium perfringens*," FEMS Microbiology Letters 106: 265-270 (1993).

Phillips-Jones, M.K., "Use of *lux* reporter system for monitoring rapid changes in α-toxin gene expression in *Clostridium perfringens* during growth," FEMS Microbiology Letters 188: 29-33 (2000).

Poptani et al., "Monitoring thymidine kinase and ganciclovir-induced changes in rat malignant glioma in vivo by nuclear magnetic resonance imaging," Cancer Gene Ther 5(2): 101-109 (1998).

Prikhod'ko, G. G. et al., "Cloning, Sequencing and Translation Analysis of the Vaccinia Virus LIVP HindIII N Fragment," Genetika 27(6): 955-963 (1991) ) [article in Russian, English summary on last page of article].

Prikhod'ko, G. G. and IV Babkin, "5'-variable genome sequence of vaccinia virus LIVP. Possible role of short direct repeats in formation of DNA deletions," Genetika 27(1): 13-26 (1991) [article in Russian, English summary on last page of article].

Qazi et al, "Real-time monitoring of intracellular *Staphylococcus aureus* replication," J Bacteriol. 186(4): 1065-1077 (2004).

Rocchetta et al., "Validation of a Noninvasive, Real-Time Imaging Technology Using Bioluminescent *Escherichia coli* in the Neutropenic Mouse Thigh Model of Infection," Antimicrobial Agents and Chemotherapy 45(1): 129-137 (2001).

Sakamoto et al., "Antitumor effect of normal intestinal microflora on Ehrlich Ascites tumor," Jpn. J. Cancer Res. (Gann) 79: 109-116 (1988).

Scholl et al., "Recombinant Vaccinia Virus Encoding Human *MUC1* and *IL2* as Immunotherapy in Patients with Breast Cancer," J. Immunother 23(5): 570-580 (2000).

Shchelkunov et al., "The gene encoding the late nonstructural 36K protein of vaccinia virus is essential for virus reproduction," Virus Research 28: 273-283 (1993).

Shimizu et al., "Antitumor activity of marine bacteria, *vibrio anguillarum*, in mice," Gann 70: 429-433 (1979).

Shimizu et al., "Antitumor activity of 2-keto-3-deoxyoctonate-free lipopolysaccharide of *vibrio anguillarum* in mice," Gann 74(2): 279-284 (1983).

Studeny et al., "Bone Marrow-derived Mesenchymal Stem Cells as Vehicles for Interferonβ Delivery into Tumors," Cancer Research 62: 3603-3608 (2002).

Thorne, S. H. and D. H. Kirn, "Future directions for the field of oncolytic virotherapy: a perspective on the use of vaccinia virus," Expert Opin Biol Ther 4(8): 1307-1321 (2004).

Tjuvajev et al., "Noninvasive Imaging of Herpes Virus Thymidine Kinase Gene Therapy and Expression: A Potential Method for Monitoring Clinical Gene Therapy," Cancer Res 56(18): 4087-4095 (1996).

Tjuvajev et al., "Imaging the Expression of Transfected Genes in Vivo," Cancer Res. 55(24): 6126-6132 (1995).

Tjuvajev et al., "Imaging Adenoviral-mediated Herpes Virus Thymidine Kinase Gene Transfer and Expression In Vivo," Cancer Research 59: 5186-5193 (1999).

Tjuvajev et al., "Imaging Herpes Virus Thymidine Kinase Gene Transfer and Expression by Positron Emission Tomography,"Cancer Res. 58(19): 4333-4341 (1998).

Vogt et al., "Untersuchungen über die Möglichkeit der Tumorlokalisation in vivo auf ser Basis eines szintigrafischer Klostridienstäbchen-Nachweises mit $^{131}$J-markierten Antikörpern and F(ab')$_2$-Antikörperfragmenten," Zeitschrift für Experimentelle Chirurgie 12(4): 209-215 (1979) [article in German, English summary on the last page of the article].

Volm et al., "Enhancement of Incorporation of $^{131}$Iododeoxyuridine into Tumors after Application of *Clostridium oncolyticum S. butyricum* (M 55)," Eur. J. Nucl. Med. 2(2): 117-120 (1977).

Xie et al., "Adenovirus-mediated Tissue-targeted Expression of a Caspase-9-based Artificial Death Switch for the Treatment of Prostate Cancer," Cancer Research 61: 6795-6804 (2001).

Yang et al., "Visualizing gene expression by whole-body fluorescence imaging," PNAS 97(22):12278-12282 (2000).

Zhao et al., "Spatial-temporal imaging of bacterial infection and antibiotic response in intact animals," Proceeding of the National Academy of Sciences 98(17): 9814-9818 (2001).

Zinoviev et al., "Identification of the gene encoding vaccinia virus immunodominant protein p35," Gene 147: 209-214 (1994).

Rehemtulla et al., "Rapid and quantitative assessment of cancer treatment response using in vivo bioluminescence imaging," Neoplasia, 2(6):491-495 (2000).

Pace, "Strep Throat," JAMA, 284(22):2964 (2000).

Cioffi et al. "A novel endothelial cell-based gene therapy platform for the in vivo delivery of apolipoprotein E" *Gene Therapy* 6:1153-1159 (1999).

Deng et al. "Engineering Ex Vivo-Expanded Marrow Stromal Cells to Secrete Calcitonin Gene-Related Peptide Using Adenoviral Vector" *Stem Cells* 22:1279-1291 (2004).

Kaufman et al., "Insertion of interleukin-2 (IL-2) and interleukin-12 (IL-12) genes into vaccinia virus results in effective anti-tumor responses without toxicity" *Vaccine* 20:1862-1869 (2002).

Kutinova et al., "Hepatitis B virus proteins expressed by recombinant vaccinia viruses: influence of preS2 sequence on expression surface and nucleocapsid proteins in human diploid cells" *Archives of Virology* 134:1-15 (1994).

Parrish et al., "Targeting widespread sites of damage in dystrophic muscle: engrafted macrophages as potential shuttles" *Gene Therapy*, 3:13-20 (1996).

Perkus et al. "Recombinant Vaccinia Virus: Immunization Against Multiple Pathogens" *Science* 229(4717):981-984 (1985).

Pfleiderer et al., "A novel vaccinia virus expression system allowing construction of recombinants without the need for selection markers, plasmids and bacterial hosts" *J. General Virology* 76:2957-2962 (1995).

Torrente et al. "Intraarterial injection of muscle-derived CD34+Sca-1+ stem cells restores dystrophin in mdx mice" *J. Cell Biol.* 152(2):335-348 (2001).

Van Damme et al. "Bone Marrow Stromal Cells as Targets for Gene Therapy" *Curr. Gene Ther*. 2:195-209 (2002).

Chaloupka, I., et al., "Comparative Analysis of Six European Influenza Vaccinesm," European Journal of Microbiology and Infectious Disease, 15(2):121-127, (1996).

Crystal, R.G., "Transfer of Genes to Humans: Early Lessons and Obstacles to Success," Science, 270:404-410, (1995).

Davis, C.G., "The Many Faces of Epidermal Growth Factor Repeats," The New Biologist, 2(5):410-419, (1990).

Eck et al., "Gene-Based Therapy," *The Pharmacological Basis of Therapeutics*, Ch. 1, Eds., Goodman and Gilman, Macmillan Publishing Co., New York, N. Y., pp. 77-101, (1996).

Gorecki, D., "Prospects and problems of gene therapy: an update," Expert Opinions in Emerging Drugs, 6(2):187-198, (2001).

Kaufman, H., et al., "A recombinant vaccinia virus expressing human carcinoembryonic antigen CEA", International Journal of Cancer, 48(6):900-907, (1991).

Kaye F.J., et al., "A single amino acid substitution results in a retinoblastoma protein defective in phosphorylation and oncoprotein binding" Proceedings of the National Academy of Science of the United States of America, 87:6922-6926, (1990).

Mutschler, E., et al., "10. Chemotherapy of Malignant Tumors," *Drug Actions: Basic Principles and Therapeutic Aspects*, Medpharm CRC Press, Suttgart, Germany, pp. 595-612, (1995).

Rudinger, J., "Characteristics of the amino acids as components of a peptide hormone sequence", *Peptide Hormones*, Ed., J.A. Parsons, University Park Press, Baltimore, p. 1-7, (1976).

Sivanandham, M. et al., "Therapeutic effect of a vaccinia colon oncolysate prepared with interleukin-2-gene encoded vaccinia virus studied in a syngeneic CC-36 murine colon hepatic metastasis model," Cancer Immunological Immunotherapy, 38:259-264, (1994).

Skolnick, J., et al., "From genes to protein structure and function: novel applications of computational approaches in the genomic era," Trends in Biotechnology, 18:34-39, (2000).

Verma, I, et al., "Gene therapy- promises, problems and prospects," Nature, 389:239-242, (1997).

Williams, R. Sanders, "Southwestern Internal Medicine Conference: Prospects for Gene Therapy of Ischemic Heart Disease," The American Journal of the Medical Sciences, 306(2):129-136, (1993).

Furlan, R., et al., "Central nervous system gene therapy with interleukin-4 inhibits progression of ongoing relapsing-remitting autoimmune encephalomyelitis in Biozzi AB/H mice," Gene Therapy, 8:13-19, (2001).

Hogaboam, C.M., et al., "Therapeutic effects of interleukin-4 gene transfer in experimental inflammatory bowel disease," Journal of Clinical Investigation, 100(11):2766-2776, (1997).

Hogervorst, E.J., et al., "Modulation of experimental autoimmunity: treatment of adjuvant arthritis by immunization with a recombinant vaccinia virus," Infection and Immunity, 59(6):2029-2035, (1991).

Lopez-Guerrero, J.A., et al., "Modulation of adjuvant arthritis in lewis rats by recombinant vaccinia virus expressing the human 60-kilodalton heat shock protein," Infection and Immunity, 61(10):4225-4231, (1993).

Macdonald, T., "Viral vectors expressing immunoregulatory cytokines to treat inflammatory bowel disease," Gut, 42:460-461, (1998).

Ruffini, F., et al., "Fibroblast growth factor-II gene therapy reverts the clinical course and the pathological signs of chronic experimental autoimmune encephalomyelitis in C57BL/6 mice," Gene Therapy, 8:1207-1213, (2001).

Wirtz, S., et al., "Efficient gene delivery to the inflamed colon by local administration of recombinant adenoviruses with normal or modified fibre structure," Gut, 44:800-807, (1999).

"Generation of Recombinant Vaccinia Viruses," Unit 16.17 in *Short Protocols in Molecular Biology $2^{nd}$ edition: a compendium of Methods from Current Protocols in Molecular Biology*, Green Publishing and Wiley-Interscience Supplement 15:16.71-16.82 (1992).

Adona et al., "Ex vivo cell labeling with $^{64}$Cu-pyruvaldehyde-bis(N$^4$-methylthiosemicarbazone) for imaging cell trafficking in mice with positron-emission tomography," Proc. Natl. Acad. Sci. USA 99: 3030-3035 (2002).

Altschul et al., "Basic local alignment search tool," J Molec Biol 215:403-410 (1990).

Ando, N. and M. Matumoto, "Unmasking of growth of dermovaccinia strain dairen I in L cells by acid treatment of cells after virus adsorption," Japan. J. Microbiol. 14(3): 181-186 (1979).

Antoine et al., "The complete genomic sequence of the modified vaccinia Ankara strain: comparison with other orthopoxviruses," Virology 244: 365-396 (1998).

ATCC Accession No. 59324.

ATCC Accession No. 59325.

ATCC Accession Nos. CCL-121.

ATCC Accession Nos. CRL-12011.

ATCC Accession Nos. CRL-12012.

ATCC catalog No. 700294.

ATCC No. CCL-107.

ATCC No. CRL-6475.

ATCC under Accession No. VR-1549.

Barrett et al., "Yellow Fever Vaccines," Biologicals 25:17-25 (1997).

Bauerschnitz et al., "Treatment of Ovarian Cancer with a Tropism Modified Oncolytic Adenovirus," Cancer Research 62: 1266-1270 (2002).

Benes et al., "M13 and pUC vectors with new unique restriction sites for cloning," Gene 130: 151-152 (1993).

Bernards et al., "Effective tumor immunotherapy directed against an oncogene-encoded produt using a vaccinia virus vector," Proc. Natl. Acad. Sci. USA 84: 6854-6858 (1987).

Beshara et al., "Kinetic analysis of $^{52}$Fe-labelled iron(III) hydroxide-sucrose complex following blous administration using positron emission tomography," Br. J. Haematol. 104: 288-295 (1999).

Beshara et al., "Pharmacokinetics and red cell utilization of iron(III) hydroxide-sucrose complex in anaemic patients: a study using positron emission tomography," Br. J. Haematol. 104: 296-302 (1999).

Bisno et al., "Streptococcal infections of skin and soft tissues," N. Engl. J. Med. 334(4): 240-245 (1996).

Blakemore, "Magnetotactic Bacteria," Annu. Rev. Microbiol. 36: 217-238 (1982).

Broder, C.C. and P.L. Earl, "Recombinant Vaccinia Viruses," Mol. Biotechnol. 13: 223-245 (1999).

Brouqui, P. and D. Raoult, "Endocarditis due to rare and fastidious bacteria," Clinical Microbiology Reviews 14(1): 177-207 (2001).

Calonder et al., "Kinetic modeling of $^{52}$Fe/$^{52m}$Mn-Citrate at the Blood-Brain Barrier by Positron Emission Tomography," J. Neurochem. 73: 2047-2055 (1999).

Carrillo and Lipman et al., "The Multiple Sequence Alignment Problem in Biology," SIAM J Applied Math 48:1073-1082 (1988).

Chakrabarti et al., "Vaccinia virus expression vector: coexpression of β-galactosidase provides visual screening of recombinant virus plaques," Mol. Cell Biol. 5:3403-3409 (1985).

Chakrabarti et al., "Compact, Synthetic, Vaccinia Virus Early/Late Promoter for Protein Expression," BioTechniques 23(6): 1094-1097 (1997).

Chamberlain et al., "Costimulation enhances the active immunotherapy effect of recombinant anticancer vaccines," Cancer Res. 56: 2832-2836 (1996).

Child et al., "Insertional inactivation of the large subunit of ribonucleotide reductase encoded by vaccinia virus is associated with reduced virulence in vivo," Virology 174:625-629 (1990).

Colinas et al., "A DNA ligase gene in the copenhagen strain of vaccinia virus is nonessential for viral replication and recombination," Virology 179: 267-275 (1990).

Cusumano et al., "Synergic activities of streptococcal pyrogenic exotoxin A and lipoteichoic acid in cytokine induction," Microbiologica 23(1): 37-45 (2000).

Davison, A. J. and B. Moss, "Structure of Vaccinia Virus Early Promoters," J. Mol. Biol. 210: 749-769 (1989).

Davison et al., "New vaccinia virus recombination plasmids incorporating a synthetic late promoter for high level expression of foreign proteins," Nucleic Acids Research 18: 4285-4286 (1990).

Devereux, J., et al., "A comprehensive set of sequence analysis programs for the VAX," Nucleic Acids Research 12(1): 387-95 (1984).

Earl et al., "T-Lymphocyte Priming and Protection Against Friend Leukemoa by Vaccinia-Retrovirus *env* Gene Recombinant," Science 234: 728-731 (1986).

Ebert et al., "Oncolytic vesicular stomatitis virus for treatment of orthotopic hepatocellular carcinoma in immune-competent rats," Cancer Research 63: 3605-3611 (2003).

Ebert et al., "Syncytia induction enhances the oncolytic potential of vesicular stomatitis virus in virotherapy for cancer," Cancer Research 64: 3265-3270 (2004).

Estin et al; "Recombinant vaccinia virus vaccine against the human melanoma antigen p97 for use in immunotherapy," Proc. Natl. Acad. Sci. USA 85: 1052-1056 (1988).

Ferretti et al., "Complete genome sequence of an M1 strain of *Streptococcus pyogenes*," Proc. Natl. Acad. Sci. USA 98(8): 4658-4663 (2001).
Flexner et al., "Successful vaccination with a polyvalent live vector despite existing immunity to an expressed antigen," Nature 355:259-262 (1988).
Flexner et al., "Characterization of Human Immunodeficiency Virus gag/pol Gene Products Expressed by Recombinant Vaccinia Viruses," Virology 166: 339-349 (1988).
Giedlin et al., "Vesicular stomatitis virus: an exciting new therapeutic oncolytic virus candidate for cancer or just another chapter from *Field's Virology*?" Cancer Cell 4: 241-243 (2003).
Goebel et al., "The complete DNA sequence of vaccinia virus," Virology 179:247-266 (1990).
Goebel et al., "Appendix to 'The complete DNA Sequence of Vaccinia Virus,'" Virology 179: 517-563 (1990).
Green et al., "Necrotizing Fasciitis," Chest 110(1):219-229 (1996).
Greinwald et al., "Treatment of lymphangiomas in children: an update of Picibanil (Ok-432) sclerotherapy," Otolaryngol Head Neck Surg 121(4): 381-387 (1999).
Gribskov et aL, "Sigma factors from *E. coli, B. subtilis*, phage SP01, and phage T4 are homologous proteins," Nucl. Acids Res. 14:6745-6763 (1986).
Huang et al., "Oncolysis of hepatic metastasis of colorectal cancer by recombinant vesticular stomatitis virus in immune-competent mice," Mol. Ther. 8(3): 434-440 (2003).
Hurst et al., "A novel model of a metastatic human breast tumour xenograft line," Br. J. Cancer 68: 274-276 (1993).
Isaacs et al., "Vaccinia virus complement-control protein prevents antibody-dependent complement-enhanced neutralization of infectivity and contributes to virulence," Proc Natl Acad Sci U S A. 89:628-632 (1992).
Johnson et al., "An update on the vaccinia virus genome," Virology 196: 381-401 (1993).
Kantor et al., "Antitumor Activity and Immune Responses Induced by a Recombinant Carcinoembryonic Antigen—Vaccinia Virus Vaccine," J. Natl. Cancer Inst. 84: 1084-1091 (1992).
Katz et al., "Mutations in the vaccinia virus A33R and B5R envelope proteins that enhance release of extracellular virions and eliminate formation of actin-containing microvilli without preventing tyrosine phosphorylation of the A36R protein," J. Virology 77:12266-12275 (2003).
Kotwal et al., "Mapping and Insertional Mutagenesis of a Vaccinia Virus Gene Encoding a 13, 800-Da Secreted Protein," Virology 171:579-587 (1989).
Kozak, M., "Structural features in Eukaryotic mRNAs that modulate the Initiation of Translation," J. Biol. Chem. 266:19867-19870 (1991).
Lamberton et al., "Construction and characterization of a bioluminescent *Streptococcus pyogene*," Proceedings of the 12th International Symposium on Bioluminescence and Chemiluminescence Progress & Current Appications, Stanley, P.E. and L.J. Kricka et al (Eds). World Scientific Publishing Co. Pte. Ltd., pp. 85-88 (2002).
Lamberton et al., "Generation and characterization of a bioluminescent *Streptococcus pyogenes*," Proceedings of the 12th International Symposium on Bioluminescence & Chemiluminescence: Apr. 5-9, 2002, Robinson College, University of Cambridge, UK, p. 3.22 (2002).
Lathe et al., "Tumour prevention and rejection with recombinant vaccinia," Nature (London) 326: 878-880 (1987).
Lee et al. "Prodrug and antedrug: two diametrical approaches in designing safer drugs," Arch. Pharm. Res. 25(2): 111-136 (2002).
Lee et al., "Molecular attenuation of vaccinia virus: mutant generation and animal characterization," Journal of Virology 66:2617-2630 (1992).
Leenders et al., "Blood to brain iron uptake in one Rhesus monkey using [Fe-52]-citrate and positron emission tomography (PET): influence of haloperidol," J. Neural.Transm.Suppl. 43: 123-132 (1994).
Lemmon et al., "Anaerobic bacteria as a gene delivery system that is controlled by the tumor microenvironment," Gene Therapy 4: 791-796 (1997).
Lemmon et al., "Anaerobic bacteria as a gene delivery system to tumors," Proceedings of the 85th Annual Meeting of the American Association for Cancer Research, San Francisco, CA Apr. 10-13, 1994, published in: Proc. Am. Cancer Research Assn 35: 374 (1994).
Lewis et al., "Comparison of Four $^{64}$Cu-Labeled Somatostatin Analogues in Vitro and in a Tumor-Bearing Rat Model: Evaluation of New Derivatives for Positron Emission Tomography Imaging and Targeted Radiotherapy," J. Med. Chem. 42: 1341-1347 (1999).
Li et al., "*Bifidobacterium adolescentis*as a delivery system of endostatin for cancer gene therapy: Selective Inhibitor of angiogenesis and hypoxic tumor growth," Cancer Gene Therapy 10: 105-111 (2003).
Liau et al., "Treatment of intracranial gliomas with bone marrow—derived dendritic cells pulsed with tumor antigens," J. Neurosurg. 90(6): 1115-1124 (1999).
Liu et al., "An E1B-19 kDa gene deletion mutant adenovirus demonstrates tumor necrosis factor-enhanced cancer selectivity and enhanced oncolytic potency," Molecular Therapy 9(6): 786-803 (2004).
Lopez et al., "Infections in children with malignant disease in Argentina," Cancer 47(5): 1023-1030 (1981).
Mayford et al., "CaMKII Regulates the Frequency—Response Function of Hippocampal Synapses for the Production of Both LTD and LTP," Cell 81: 891-904 (1995).
Mayr et al., "The Smallpox Vaccination Strain MVA: Marker, Genetic Structure, Experience Gained with the Parenteral Vaccination and Behavior in Organisms with a Debilitated Defense Mechanism," Zentbl. Bakteriol. Hyg. Abt 1 Orig. B 167: 375-390 (1978) [In German, English abstract on first page of article].
McAllister et al., "Recombinant yellow fever viruses are effective therapeutic vaccines for treatment of murine experimental solid tumors and pulmonary metastases," J. Virol. 74:9197-9205 (2000).
McAneny et al., "Results of a Phase I trial of a recombinant vaccinia virus that expresses carcinoembryonic antigen in patients with advanced colorectal cancer,"Ann. Surg. Oncol. 3(5): 495-500 (1996).
Mikryukov et al., "Structural-functional organization of segment of vaccinia virus genome," Soviet Biotechnology (Biotekhnologiya) 4: 19-25 (1988) [corresponds to pp. 442-449 in the Russian language edition].
Moore et al., "Steroid hormone synthesis by a vaccinia enzyme: a new type of virus virulence factor," EMBO J. 1992 11:1973-1980, corrigendum in The EMBO Journal 11(9): 3490 (1992).
Moss, B., "Genetically engineered poxviruses for recombinant gene expression, vaccination, and safety," Proc. Natl. Acad. Sci. USA 93: 11341-11348 (1996).
Moss, B., "Poxvirus vectors: cytoplasmic expression of transferred genes," Curr. Opin. Genet. Dev. 3: 86-90 (1993).
Mullen et al., "Viral Oncolysis," The Oncologist 7: 106-119 (2002).
Mulryan et al., "Attenuated recombinant vaccinia virus expressing oncofetal antigen (tumor-associated antigen) 5T4 induces active therapy of established tumors," Mol Cancer Ther 1(12): 1129-1137 (2002).
Munagala et al., "The purine nucleoside phosphorylase from *Trichomonas vaginalis* is a homologue of the bacterial enzyme," Biochemistry 41(33): 10382-10389 (2002).
NCBI Protein AAA48282.
NCBI Nucleotide AF012825.
NCBI Nucleotide. AF095689.
NCBI Nucleotide AF380138.
NCBI Nucleotide AX003206.
NCBI Nucleotide. AY009089.
NCBI Nucleotide AY243312.
NCBI Nucleotide AY484669.
NCBI Nucleotide AY603355.
NCBI Nucleotide M35027.
NCBI Nucleotide M57977.
NCBI Nucleotide U94848.
NCBI Nucleotide X69198.
NCBI Nucleotide X94355.
Needleman et al., "A general method applicable to the search for similarities in the amino acid sequences of two proteins," J. Mol. Biol. 48:443-453 (1970).

Nogrady, T., *Medicinal Chemistry A Biochemical Approach*, New York: Oxford University Press, pp. 388-392 (1985).

Oertli et al., "Non-replicating recombinant vaccinia virus encoding murine B-7 molecules effective costimulation of naive CD4+ splenocytes in vitro," J. Gen. Virol. 77: 3121-3125 (1996).

Okamoto et al., "Severe impairment of anti-cancer effect of lipoteichoic acid-relatedmolecule isolated from a penicillin-killed *Streptococcus pyogenes* in toll-like receptor 4-deficient mice," International Immunopharmacology 1(9-10): 1789-1795 (2001).

Patel et al., "A poxvirus-derived vector that directs high levels of expression of cloned genes in mammalian cells," Proc. Natl. Acad. Sci. USA 85: 9431-9435 (1988).

Pawelek et al., "Tumor-targeted *Salmonella* as a Novel Anticancer Vector," Cancer Therapy 57: 4537-4544 (1997).

Pearson et al., "Improved tools for biological sequence comparison," Proc. Natl. Acad. Sci. USA 85:2444-2448 (1988).

Pilcher, H., "GM Bug activates cancer drug: Bacteria targets medicine to shrivel mouse tumours," news @ nature.com, Published online: Apr. 22, 2004; http://www.nature.com/news/2004/040419/full/040419-9.html, (accessed on Nov. 18, 2004).

Pinkert et al., "An albumin enhancer located 10 kb upstream functions along with its promoter to direct efficient, liver-specific expression in transgenic mice," Genes & Dev. 1: 268-76 (1987).

Plucienniczak et al., "Nucelotide sequence of a cluster and late genes in a conserved segment of the vaccinia virus genome," Nucleic Acids Research 13(3): 993-998 (1985).

Puhlmann et al., "Vaccinia virus as a vector for tumor-directed gene therapy: biodistribution of a thymidine kinase-deleted mutant," Cancer Gene Therapy 7(1): 66-73 (2000).

Qin, H. and S.K. Chatterjee, "Cancer gene therapy using tumor cells infected with recombinant vaccinia virus expressing GM-CSF," Human Gene Ther. 7: 1853-1860 (1996).

Rao et al., "Il-12 is an effective adjuvant to recombinant vaccinia virus-based tumor vaccines," J. Immunol. 156: 3357-3365 (1996).

Rodriguez et al., "Highly attenuated vaccinia virus mutants for the generation of safe recombinant viruses," Proc. Natl. Acad. Sci. USA 86: 1287-1291 (1989).

Rolston et al., "In vitro activity of LY264826, a new glycopeptide antibiotic, against gram-positive bacteria isolated from patients in cancer," Antimicrob. Agents Chemother. 34(11):2137-2141 (1990).

Roseman et al., "The vaccinia virus *Hin*dIII fragment: nucleotide sequence of the left 6.2kb," Virology 178: 410-418 (1990).

Roth et al,, "p53 as a target for cancer vaccines: recombinant canarypox virus vectors expressing p53 protect mice against lethal tumor cell challenge," Proc. Natl. Acad. Sci. USA 93: 4781-4786 (1996).

Schwartz and Dayhoff, eds., Atlas of Protein Sequence and Structure, National Biomedical Research Foundation, pp. 353-358 (1979).

Shilo, B. and R.A. Weinberg, "DNA sequences homologous to vertebrate oncogenes are conserved in Drosophila *melanogaster*," Proc. Natl. Acad. Sci. USA 78:6789-6792 (1981).

Shinozaki et al.; "Oncolysis of multifocal hepatocellular carcinoma in the rat liver by hepatic artery infusion of vesicular stomatitis virus," Mol. Ther. 9(3): 368-376 (2004).

Silva et al., "Cloning, overexpression, and purification of functional human purine nucleoside phosphorylase," Protein Expr. Purif. 27(1): 158-164 (2003).

Smith, T.F. and M.S.Waterman, "Comparison of biosequences," Adv. Appl. Math. 2:482-489 (1981).

Sorscher et al., "Tumor cell bystander killing in colonic carcinoma utilizing the *Escherichia coli DeoD* gene to generate toxic purines," Gene Therapy 1(4): 233-238 (1994).

Stevens, D.L., "Stretococcal toxic-shock syndrome: spectrum of disease, pathogenesis, and new concepts in treatment," Emerg. Infect. Dis. 1(3): 69-78 (1995).

Sugimoto, M. and K. Yamanouchi., "Characteristics of an attenuated vaccinia virus strain, LC16m0, and its recombinant virus vaccines," Vaccine 12(8): 675-681 (1994).

Sugimoto et al., "Gene structures of low-neurovirulent vaccinia virus LC16m0, LC16m8, and their Lister Original (LO) strains," Microbial. Immunol. 29: 421-428 (1985).

Suvorov et al., "Physical and genetic chromosomal map of an M type 1 strain of *Streptococcus pyogenes*," J. Bacteriol. 178(18): 5546-5549 (1996).

Suzuki et al., "Management of orbital lymphangioma using intralesional injection of OK-432," Br. J. Opthalmol. 84(6): 614-617 (2000).

Sze et al., "Dr. Gary J. Becker Young Investigator Award: intraarterial adenovirus for metastatic gastrointestinal cancer: activity, radiographic response, and survival," J. Vasc. Interv. Radiol. 14(3): 279-290(2003).

Takahashi-Nishimaki et al., "Genetic analysis of vaccinia virus Lister strain and its attenuated mutant LC16m8: production of intermediate variants by homologous recombination," J. Gen. Virol. 68: 2705-2710 (1987).

Theys et al., "Tumor-specific gene delivery using genetically engineered bacteria," Curr Gene Ther 3(3): 207-221 (2003).

Timiriasova et al., "[Analysis of reporter gene expression at different segments of the vaccinia virus genome]," Mol. Biol. (Mosk.) 27(2): 392-401 (1993) [article in Russian, English abstract on last page of article].

Timiryasova et al., "Construction of recombinant vaccinia viruses using PUV-inactivated virus as a helper," BioTechniques 31: 534-540 (2001).

Toth et al., "An oncolytic adenovirus vector combining enhanced cell-to-cell spreading, mediated by the ADP cytolytic protein, with selective replication in cancer cells with deregulated *Wnt* signaling," Cancer Research 64: 3638-3644 (2004).

Tsung et al. "Gene expression and cytopathic effect of vaccinia virus inactivated by psoralen and long-wave UV light," J. Virol. 70: 165-171 (1996).

Umphress et al., "Vaccinia virus mediated expression of human APC induces apoptosis in colon cancer cells," Transgenics 4:19-33 (2003).

Veijola et al., "Cloning, Baculovirus Expression, and Characterization of the α Subunit of Prolyl 4-Hydroxylase from the nematode *Caenorhabditis elegans*," J. Biol. Chem. 269: 26746-26753 (1994).

Vidal et al., "Tissue-specific control elements of the Thy-1 gene," EMBO J. 9(3): 833-840 (1990).

Watson et al. Molecular Biology of the Gene, 4th Edition, 1987, The Benjamin/Cummings Pub. co., p. 224.

Wolffe et al., "Deletion of the vaccinia virus B5R gene encoding a 42-kilodalton membrane glycoprotein inhibits extracellular virus envelope formation and dissemination," Journal of Virology 67(8): 4732-4741 (1993) and erratum in Journal of Virology, vol. 67, pp. 5709-5711 (1993).

Wu et al., "High resolution microPET imaging of carcino-embryonic antigen-positive xenografts by using a copper-64-labeled engineered antibody fragment," PNAS USA 97(15): 8495-8500 (2000).

Yang et al., "Whole-body optical imaging of green fluorescent protein-expressing tumors and metastases," Proc. Natl. Acad. Sci. USA 97(3):1206-1211 (2000).

Yang et al., "Effects of growth medium composition, iron sources and atmospheric oxygen concentrations on production of luciferase-bacterial magnetic particle complex by a recombinant *Magnetospirillum magneticum* AMB-1," Enzyme Microb. Technol. 29: 13-19 (2001).

Yazawa et al., "Current progress in suicide gene therapy for cancer," World J. Surg 26(7): 783-789 (2002).

Yoshida et al., "Cell growth-inhibitory action of SAGP, an antitumor glycoprotein from *Streptococcus pyogenes* (Su strain)," Jpn. J. Pharmacol. 45(2): 143-147 (1987).

Yoshida et al., "Characterization of a streptococcal antitumor glycoprotein (SAGP)," Life Sciences 62(12): 1043-1053 (1998).

Yoshida et al., "Growth-inhibitory effect of streptococcal antitumor glycoprotein on human epidermoid carcinoma A431 cells: involvement of dephosphorylation of epidermal growth factor receptor," Cancer Research 61(16): 6151-6157 (2001).

Zimmermann et al., "Independent regulatory elements in the nestin gene direct transgene expression to neural stem cells," Neuron 12: 11-24 (1994).

Zolotukhin et al., "A 'Humanized' Green Fluorescent Protein cDNA adapted for high-level expression in mammalian cells," *J Virol.* 70:4646-4654 (1996).

Advisory Committee on Immunization Practices (ACIP), "Smallpox vaccination and adverse reactions: guidance for clinicians", Morbidity and Mortality Weekly Report 52(RR-4): 1-29 (Feb. 21, 2003).

Advisory Committee on Immunization Practices (ACIP), Vaccinia (smallpox) vaccine: recommendations of the Advisory Committee on Immunization Practices (ACIP), MMWR, 50(RR-10): 1-26 & cel-cel (Jun. 22, 2001).

Aebischer et al., "Long-Term Cross-Species Brain Transplantation of a Polymer-Encapsulated Dopamine-Secreting Cell Line," Experimental Neurology 111:269-275 (1991).

Aebischer et al., "Functional Recovery in Hemiparkinsonian Primates Transplanted with Polymer-Encapsulated PC12 Cells," Experimental Neurology 126:151-158 (1994).

Aguilar, O.M. et al., The *nifEN* genes participating in FeMo cofactor biosynthesis and genes encoding dinitrogenase are part of the same operon in *Bradyrhizobium species*. Mol Gen Genet. 224(3):413-20 (1990).

Alcami, A. et al., "Vaccinia virus strains Lister, USSR and Evans express soluble and cell-surface tumour necrosis factor receptors," J. Gen. Virol., 80: 949-959 (1999).

Antoine, G. et al., "Characterization of the vaccinia MVA hemagglutinin gene locus and its evaluation as an insertion site for foreign genes," Gene, 177: 43-46 (1996).

Arakawa, S. et al., "Clinical trial of attenuated vaccinia virus AS strain in the treatment of advanced adenocarcinoma," J. Cancer Res. Clin. Oncol., 113: 95-98 (1987).

Baeksgaard, L. and J.B. Sorensen, "Acute tumor lyssi syndrome in solid tumors—a case report and review of the literature," Cancer Chemother. Pharmacol., 51: 187-192 (2003).

Baker, R.O. et al., "Potential antiviral therapeutics for smallpox, monkeypox, and other orthopoxvirus infections," Antiviral Research, 57: 13-23 (2003).

Balkwill, F., "Chemokine biology in cancer," Seminars in Immunol., 15: 49-55 (2003).

Baxby, D., "Poxviruses," Chapter 15 in *Principles and Practice of Clinical Virology*, Zuckerman, A.J. et al.(eds.), John Wiley & Sons Ltd., pp. 451-465 (2000).

Beebe, J.L. and E.W. Koneman, "Recovery of Uncommon Bacteria from Blood: Association with Neoplastic Disease," Clin. Microbiol. Rev., 8(3): 336-356 (1995).

Beerntsen, B.T. et al., "Genetics of Mosquito Vector Competenc," Microbiol. Mol. Biol. Rev., 64(1): 115-137 (2000).

Belas et al., "Bacterial Bioluminescence: Isolation and Expression of the Luciferase Genes from Vibrio harveyi," Science, 218: 791-793 (1982).

Bell, J.C. et al., "Getting oncolytic virus therapies off the ground," Cancer Cell, 4: 7-11 (2003).

Bendig, M.M., "The production of foreign proteins in mammalian cells," Genetic Engineering 7:91-127 (1988).

Bergsland, E.K. and A.P. Venook, "Shedding Old Paradigms: Developing Viruses to Treat Cancer," J. Clin. Oncol., 20(9): 2220-2222 (2002).

Bermudes et al., "Live bacteria as anticancer agents and tumor-selective protein delivery vectors," Current Opinion in Drug Discovery & Development 5(2):194-199 (2002).

Best et al., "Baboon/human homologies examined by spectral karyotyping (SKY): a visual comparison," Cytogenet Cell Genet. 82(1-2):83-7 (1998).

Bickels, J. et al., "Coley's toxin: historical perspective," Isr. Med. Assoc. J., 4(6): 471-472 (2002).

Blanchard, T.J. et al., "Modified vaccinia virus Ankara undergoes limited replication in human cells and lacks several immunomodulatory proteins: implications for use as a human vaccine," Journal of General Virology, 79: 1159-1167 (1998).

Blasco, R. and B. Moss, "Selection of recombinant vaccinia viruses on the basis of plaque formation," Gene, 158: 157-162 (1995).

Bogdahn et al., "Autocrine Tumor Cell Growth-inhibiting Activities from Human Malignant Melanoma," Cancer Research 49:5358-5363 (1989).

Borellini, F. and J.M. Ostrove, "The Transfer of Technology from the Laboratory to the Clinic: In Process Controls and Final Product Testing," Chapter 18 in *Gene Therapy Technologies, Applications and Regulations*, A. Meager (Ed.), John Wiley & Sons Ltd., pp. 359-373 (1999).

Boulanger, D. et al., "Morphogenesis and release of fowlpox virusm," Journal of General Virology, 81: 675-687 (2000).

Bouvier et al., "Functional characterization of the human dopamine D-4.2 receptor using vaccinia virus as an expression system," European Journal of Pharmacology 290(1):11-17 (1995).

Boyd, J.E., "Facilities for Large-Scale Production of Vectors under GMP Conditions," Chapter 20 in *Gene Therapy Technologies, Applications and Regulations*, A. Meager (Ed.), pp. 383-400 (1999).

Brain, J.D. et al., "Pulmonary intravascular macrophages: their contribution to the mononuclear phagocyte system in 13 species", Am. J. Physiol., 276(1 pt 1): L146-L154 (1999).

Breman, J.G. and D.A. Henderson, "Diagnosis and Management of Smallpox," N. Engl. J. Med., 346(17): 1300-1308 (2002).

Broder, C.C. et al., "Expression of foreign genes in cultured human primary macrophages using recombinant vaccinia virus vectors," Gene, 142: 167-174 (1994).

Broyles, S.S., "Vaccinia virus transcription," Journal of General Virology, 84: 2293-2303 (2003).

Brunke M et al., "Luciferase assembly after transport into mammalian microsomes involves molecular chaperones and peptidyl-prolyl cis/trans-isomerases," J Biol Chem. 271(38):23487-94 (1996).

Carroll, S.F. and R.J. Collier, "Active Site of *Pseudomonas aeruginosa* Exotoxin A," J. Biol. Chem. 262:8707-8711 (1987).

Carter, G.C. et al., "Vaccinia virus cores are transported on microtubules," Journal of General Virology, 84: 2443-2458 (2003).

Cavanagh, L.L. and U.H. von Andrian, "Travellers in many guises:The origins and destinations of dendritic cells," Immunology and Cell Biology, 80: 448-462 (2002).

Chalfie et al., "Green Fluorescent Protein as a Marker for Gene Expression," Science 263: 802-805 (1994).

Chambers, A.F. et al., "Dissemination and Growth of Cancer Cells in Metastatic Sites," Nat. Rev. Cancer, 2: 563-572 (2002).

Chambers, A.F. et al., "Molecular biology of breast cancer metastasis Clinical implications of experimental studies on metastatic inefficiency," Breast Cancer Res., 2: 400-407 (2000).

Chaudhary et al., "Role of domain II of *Pseudomonas* exotoxin in the secretion of proteins into the periplasm and medium by *Escherichia coli*," Proc. Natl. Acad. Sci. USA 85: 2939-2943 (1988).

Cheadle, E.J. and A.M. Jackson, "Bugs as Drugs for Cancer," Immunology 107: 10-19 (2002).

Chen et al. "Evaluation of combined vaccinia virus-mediated antitumor gene therapy with p53, IL-2, and IL-12 in a glioma model." Cancer Gene Ther. 7(1)):1437-47 (2000).

Chen et al. "Cancer gene therapy by direct tumor injections of a nonviral T7 vector encoding a thymidine kinase gene," Hum Gene Ther. 9(5):729-36 (1998).

Chiocca, E.A., "Oncolytic Viruses," Nat. Rev. Cancer, 2(12): 938-950 (2002).

Choi et al., "Efficient secretory production of alkaline phosphatase by high cell density culture of recombinant *Escherichia coli* using the *Bacillus* sp. endoxylanase signal sequence," Appl. Microbiol. Biotechnol. 53:640-645 (2000).

Cichutek, K., "Development and Regulation of Gene Therapy Drugs in Germany," Chapter 17 in Gene Therapy Technologies, Applications and Regulations, A. Meager (Ed.), John Wiley & Sons Ltd. pp. 347-358 (c1999).

Clairmont, C. et al., "Enhanced antitumor activity from tumor-targeting *Salmonella* expressing endostatin," American Association for Cancer Research: 91st Annual Meeting of the AACR, Apr. 1-5, 2000, 41:732 Abstract #4653 (2000).

Compton, J.L. and A.A. Szalay, "Insertion of nonhomologous DNA into the yeast genome mediated by homologous recombination with a cotransforming plasmid," Mol Gen Genet. 188(1):44-50 (1982).

Condeelis, J. and J.E. Segall, "Intravital imaging of cell movement in tumours," Nat. Rev. Cancer, 3: 921-930 (2003).

Contag et al., "Photonic detection of bacterial pathogens in living hosts," Mol. Microbiol. 18: 593-603 (1995).

Coupar, B.E.H. et al., "A general method for the construction of recombinant vaccinia viruses expressing multiple foreign genes," Gene, 68: 1-10 (1988).

Coussens, L.M. and Z. Werb, "Inflammation and cancer," Nature, 420: 860-867 (2002).
Craperi et al. "Increased bax expression is associated with cell death induced by ganciclovir in a herpes thymidine kinase gene-expressing glioma cell line." Hum Gene Ther. 10(4):679-688 (1999).
Cseh, S. et al., "Rapid freezing of mouse embryos in ethylene glycol at different preimplantation stages," Acta Veterinaria Hungarica 44(4):457-65 (1996).
Culver et al., "In vivo gene transfer with retroviral vector-producer cells for treatment of experimental brain tumors." Science. 256(5063):1550-2 (1992).
Davis, C. et al., "The role of inflammation in vascular injury and repair," Journal of Thrombosis and Haemostasis, 1: 1699-1709 (2003).
De Clercq, E., "Cidofovir in the therapy and short-term prophylaxis of poxvirus infections," Trends in Pharmacological Sciencs, 23(10): 456-458 (2002).
Demers, G.W. et al., "Pharmacologic Indicators of Antitumor Efficacy for Oncolytic Virotherapy", Cancer Res., 63: 4003-4008 (2003).
Derwent English abstract for WO 94/10302, published May 11, 1994 entitled: "Vectors inhibiting HIV replication in potential host cells—contg. DNA encoding Pol, Gag, Env, Rev, and/or Tat in antisense direction and further DNA causing spontaneous amplification," Accession Nbr. 1994-152544 [19].
de Wet et al., "Firefly Luciferase Gene: Structure and Expression in Mammalian Cells," Mol. Cell. Biol. 7: 725-737 (1987).
Diamond, D.C. et al. "Sequence comparison of baboon ABO histo-blood group alleles: lesions found in O alleles differ between human and baboon," Blood Cells Mol Dis. 23(2):242-51 (1997).
Diamond, D.C., et al., "Genotying the baboon ABO histo—blood group locus by two-color fluorescence SSCP," Biotechniques 27(5):1054, 1056, 1058-59, 1061 (1999).
Dietrich, G. et al., "Delivery of antigen—encoding plasmid DNA into the cytosol of macrophages by attenuated suicide Listeria monocytogenes," Nat Biotechnol. 16(2):181-5 (1998).
Ding et al., "Zinc-dependent dimers observed in crystals of human endostatin," Proc. Natl. Acad. Sci. USA 95:10443-10448 (1998).
Dobbelstein, M., "Viruses in therapy—royal road or dead end?", Virus Research, 92: 219-221 (2003).
Domi, A. and B. Moss, "Cloning the vaccinia virus genome as a bacterial artificial chromosome in *Escherichia coli* and recovery of infectious virus in mammalian cells," Proc. Natl. Acad. Sci. U.S.A., 99(19): 12415-12420 (2002).
Dull et al., "Insulin-like growth factor II precursor gene organization in relation to insulin gene therapy," Nature 310: 777-781 (1984).
Eastham et al. "Prostate cancer gene therapy: herpes simplex virus thymidine kinase gene transduction followed by ganciclovir in mouse and human prostate cancer models." Hum Gene Ther. 7(4):515-23 (1996).
Ehrengruber, M.U., "Alphaviral gene transfer in neurobiology," Brain Research Bulletin, 59(1): 13-22 (2002).
Engebrecht et al., "Measuring Gene Expression with Light," Science 227: 1345-1347 (1985).
Escher, A. et al., "Bacterial luciferase αβ fusion protein is fully active as a monomer and highly sensitive in vivo to elevated temperature," Proc Natl Acad Sci U S A. 86(17):6528-32 (1989).
Escher, A et al., "The β subunit polypeptide of Vibrio harveyi luciferase determines light emission at 42° C," Mol Gen Genet. 230(3):385-93 (1991).
Escher, A. and A.A. Szalay, "GroE-mediated folding of bacterial luciferases in vivo," Mol Gen Genet. 238(1-2):65-73 (1993).
Esposito, J.J. and F. Fenner, "Poxviruses", Chapter 85 in Field's Virology, 4th Edn., vol. 2, pp. 2885-2921. Edited by D. M. Knipe and P. M. Howley, Philadelphia: Lippincott Williams & Wilkins, (2001).
Fatyol, K et al., "Mer22—related sequence elements form pericentric repetitive DNA families in primates," Mol Gen Genet. 262(6):931-9 (2000).
Fatyol, K et al. "Molecular characterization of a stably transformed *Bombyx mori* cell line: identification of alternative transcriptional initiation sites of the A3 cytoplasmic actin gene." Mol Gen Genet. 260(1):1-8 (1998).

Fatyol, K et al., "An alternative intronic promoter of the Bombyx A3 cytoplasmic actin gene exhibits a high level of transcriptional activity in mammalian cells," Mol Gen Genet. 261(2):337-45 (1999).
Fatyol, K and A.A. Szalay, "The p14$^{ARF}$ tumor suppressor protein facilitates nucleolar sequestration of hypoxia-inducible factor-lα (HIF-1α) and inhibits HIF-1-mediated transcription," J Biol Chem. 276(30):28421-28429 (2001).
Fernández-Piñas, F. A and C.P. Wolk, "Expresssion of *luxCD-E* in *Anabaena* sp. can replace the use of exogenous aldehyde for in vivo localization of transcription by *luxAB*," Gene 150:169-174 (1994).
Fidler, I.J., "The pathogenesis of cancer metastasis: the 'seed and soil' hypothesis revisited," Nature Cancer Research, 3: 1-6 (2003).
Foran, D.R. and W.M. Brown, "Nucleotide sequence of the LuxA and LuxB genes of the bioluminescent marine bacterium *Vibrio fischeri*," Nucleic Acids Res. 16: 777 (1988).
Forbes, N.S. et al., "Sparse Initial Entrapment of Systematically Injected *Salmonella typhimurium* Leads to Heterogenous Accumulation within Tumors," Cancer Res., 63: 5188-5193 (2003).
Fox, A.W., "Emergency and Compassionate-use INDs and Accelerated NDS or ANDA Approvals—Procedures, Benefits and Pitfalls," Chapter 26 in Principles and Practice of Pharmaceutical Medicine, A.J. Fletcher, et al.(Eds.), John Wiley & Sons, pp. 299-305, (2002).
Freed et al., "Survival of Implanted Fetal Dopamine Cells and Neurologic Improvement 12 to 46 Months After Transplantation for Parkinson's Disease," New England Journal of Medicine 327:1549-1555 (1992).
Freitag, N. E. and K.E. Jacobs, "Examination of *Listeria monocytogenes* Intracellular Gene Expression by Using Green Fluorescent Protein of *Aequorea victoria*," Infect.Immun. 67:1844-1852 (1999).
Friberg, S. and S. Mattson, "On the Growth Rates of Human Malignant Tumors: Implications for Medical Decision Making," Journal of Surgical Oncology, 65: 284-297 (1997).
Gallagher, R., "Vaccination Undermined,", The Scientist, 17(22): 1-3 (2003).
Geng, J.G., "Directional migration of leukocytes: their pathological roles in inflammation and strategies for development of anti-inflammatory therapies," Cell Res., 11(2): 85-88 (2001).
Geng, J.G., "Interaction of vascular endothelial cells with leukocytes, platelets and cancer cells in inflammation, thrombosis and cancer growth and metastasis," Acta Pharmacol. Sin, 24(12): 1297-1300 (2003).
Giacomin, L.T. and A.A. Szalay, "Expression of a PALI promoter luciferase gene function in *Arabidopsis thaliana* in response to infection by phytopathogenic bacteria," Plant Sci. 116: 59-72 (1996).
Gnant, M.F.X. et al, "Tumor-Specific Gene Delivery.Using Recombinant Vaccinia Virus in a Rabbit Model of Liver Metastases", Journal of the National Cancer Institute, 91(20): 1744-1750 (1999).
Goetz et al., "Multicenter Study of Autologous Adrenal Medullary Transplantation to the Corpus Striatum in Patients with Advanced Parkinson's Disease", N. Eng. J. Med. 320:337-341 (1989).
Goetz, M et al., "Microinjection and growth of bacteria in the cytosol of mammalian host cells," Proc Natl Acad Sci U S A. 98(21):12221-12226. (2001).
Gomella, L.G. et al., "Phase I Study of Intravesical Vaccinia Virus as a Vector for Gene Therapy of Bladder Cancer", J. Urology, 166: 1291-1295 (2001).
Gómez, C.E. and M. Esteban, "Recombinant proteins produced by vaccinia virus vectors can be incorporated within the virion (IMV form) into different compartments," Arch. Virol., 146: 875-892 (2001).
Graff, C.P. and K.D. Wittrup, "Theoretical Analysis of Antibody Targeting of Tumor Spheroids: Importance of Dosage for Penetration, and Affinity for Retention," Cancer Res., 63: 1288-1296 (2003).
Gray, J.W., "Evidence emerges for early metastasis and parallel evolution of primary and metastatic tumors", Cancer Cell, 4(1): 4-6 (2003).
Green, D.R. and G.I. Evan, "A matter of life and death", Cancer Cell, 1: 19-30 (2002).
Greer III, L.F. and A.A. Szalay, "Imaging of light emission from the expression of luciferases in living cells and organisms: a review," Luminescence. 17(1):43-74 (2002).

Griffin, D.E., "A Review of Alphavirus Replication in Neurons," Neuroscience and Biobehavioral Reviews, 22(6): 721-723 (1998).

Grove et al. "Virus-directed enzyme prodrug therapy using CB1954" Anti-Cancer Drug Design 14(6) 461-472 (1999).

Guy et al., "Expression of the neu protooncogene in the mammary epithelium of transgenic mice induces metastatic disease," Proc. Natl. Acad. Sci.USA 89: 10578-10582 (1992).

Hacein-Bey-Abina, S. et al., "A Serious Adverse Event after Successful Gene Therapy for X-Linked Severe Combined Immunodeficiency", N. Engl. J. Med., 348(3): 255-266 (2003).

Hadley, R.G. et al., "Conservation of DNA regions adjacent to nifKDH homologous sequences in diverse slow-growing *Rhizobium* strains," J Mol Appl Genet. 2(3):225-36 (1983).

Haghighat et al. "Antitumor effect of IL-2, p53, and bax gene transfer in C6 glioma cells," Anticancer Res. 20(3A):1337-42 (2000).

Hall et al., "Adenovirus-mediated herpes simplex virus thymidine kinase gene and ganciclovir therapy leads to systemic activity against spontaneous and induced metastasis in an orthotopic mouse model of prostate cancer," Int I Cancer. 70(2):183-7 (1997).

Halsell, J.S. et al., "Myopericarditis Following Smallpox Vaccination Among Vaccinia-Naïve US Military Personnel", J. Am. Med. Assoc., 289(24): 3283-3289 (2003).

Hanahan, D. and R.A. Weinberg, "The Hallmarks of Cancer", Cell, 100: 57-70 (2000).

Hansen, R.M. and J.A. Libnoch, "Remission of Chronic Lymphocytic Leukemia After Smallpox Vaccination," Arch. Intern. Med., 138: 1137-1138 (1978).

Hawkins, L.K. et al., "Oncolytic biotherapy: a novel therapeutic platform," The Lancet Oncology, 3: 17-26 (2002).

Hemann et al., "High-Copy Expression Vector Based on Amplification-Promoting Sequences", DNA and Cell Biology 13:437-445 (1994).

Hermiston, T.W. and I. Kuhn, "Armed therapeutic viruses: Strategies and challenges to arming oncolytic viruses with therapeutic genes," Cancer Gene Therapy, 9: 1022-1035 (2002).

Hershey, P. et al., "Adjuvant Immunotherapy of Patients With High-Risk Melanoma Using Vaccinia Viral Lysates of Melanoma: Results of a Randomized Trial," Journal of Clinical Oncology, 20(20): 4181-4190 (2002).

Hess et al., "*Listeria monocytogenes* p60 supports host cell invasion by and in vivo survival of attenuated *Salmonella typhimurium*," Infect Immun. 63(5):2047-53 (1995).

Hollinshead, M. et al., "Vaccinia virus utilizes microtubules for movement to the cell surface," Journal of Cell Biology, 154: 389-402 (2001).

Holló, G et al., "Evidence for a megareplicon covering megabases of centromeric chromosome Segments," Chromosome Res. 4(3):240-7 (1996).

Hosokawa et al., "Pituitary Carcinoma of Pars Distalis as a Common Neoplasm in Fischer-344 Rats," Toxicol. Pathol. 21: 283-287 (1993).

Hughes, R.G. and N. Turner, "Financial Aspects of Clinical Trials", Chapter 42 in *Principles and Practice of Pharmaceutical Medicine*, A.J. Fletcher, et al.(eds.), pp. 501-512, John Wiley & Sons, Ltd. (2002).

Humlova, Z. et al., "Vaccinia virus induces apoptosis of infected macrophages," J. General Virol., 83: 2821-2832 (2002).

Jain, R.K. and B.T. Fenton, "Intratumoral Lymphatic Vessels: A Case of Mistaken Identity or Malfunction?," Journal of the National Cancer Institute, 94(6): 417-421 (2002).

Jain, R.K., "Molecular regulation of vessel maturation," Nat. Med., 9(6): 685-693 (2003).

Jemal, A. et al., "Cancer Statistics, 2003", CA Cancer J Clin, 53(1): 5-26 (2003).

Jeong, K.J. and S.Y. Lee, "Secretory Production of Human Leptin in *Escherichia coli*," Biotechnol.Bioeng. 67:398-407 (2000).

Kaniga et al., "Homologs of the *Shigella* IpaB and IpaC Invasins are Required for *Salmonella typhimurium* Entry into Cultured Epithelial Cells," J. Bacteriol. 177: 3965-3971 (1995).

Kawa, A. and S. Arakawa, "The Effect of Attenuated Vaccinia Virus AS Strain on Multiple Myeloma; A Case Report," Japan. J. Exp. Med. 58(1): 79-81 (1987).

Keith, K.A. et al., "Evaluation of Nucleoside Phosphonates and Their Analogs and Prodrugs for Inhibition of Orthopoxvirus Replication," Antimicr. Agents Chemothera., 47(7): 2193-2198 (2003).

Keresó, J. et al., "De novo chromosome formations by large-scale amplification of the centromeric region of mouse chromosomes," Chromosome Res. 4(3):226-39 (1996).

Kern, E.R., "In vitro activity of potential anti-poxvirus agents", Antiviral Research 57: 35-40 (2003).

Kihara, A. and I. Pastan, "Analysis of Sequences Required for the Cytotoxic Action of a Chimeric Toxin Composed of *Pseudomonas* Exotoxin and Transforming Growth Factor α," Bioconj.Chem. 5: 532-538 (1994).

Kim, E.M. et al., "Overview analysis of adjuvant therapies for melanomaFa special reference to results from vaccinia melanoma oncolysate adjuvant therapy trials", Surgical Oncology, 10: 53-59 (2001).

Kleer, C.G. et al., "Molecular biology of breast cancer metastasis Inflammatory breast cancer: clinical syndrome and molecular determinants," Breast Cancer Res. 2: 423-429 (2000).

Kneissl, M. et al., "Interaction and assembly of murine pre-replicative complex proteins in yeast and mouse cells," J Mol Biol. 327(1):111-28 (2003).

Kolowsky K.S. et al., "Length of foreign DNA in chimeric plasmids determines the efficiency of its integration into the chromosome of the cyanobacterium Synechococcus R2," Gene 27(3):289-99 (1984).

Kondo et al., "Activity of Immunotoxins Constructed with Modified Pseudomonas Exotoxin A Lacking the Cell Recognition Domain," J.Biol.Chem. 263: 9470-9475 (1988).

Krauss, O. et al., "An investigation of incorporation of cellular antigens into vaccinia virus particles," Journal of General Virology, 83: 2347-2359 (2002).

Kruse, M, et al., "Enzyme assembly after de novo synthesis in rabbit reticulocyte lysate involves molecular chaperones and immunophilins," J Biol Chem. 270(6):2588-94 (1995).

Kubes, P., "Introduction: The complexities of leukocyte recruitment," Seminars in Immunol. 14: 65-72 (2002).

Kunkel, E.J. Aand E.C. Butcher, "Plasma-cell homing," Nature Reviews Immunology, 3: 822-829 (2003).

Kwak, H. et al., "Poxviruses as vectors for cancer immunotherapy," Curr. Opin. Drug Disc. Develop., 6(2): 161-168 (2003).

Langridge W.H. et al, "Detection of baculovirus gene expression in insect cells and larvae by low light video image analysis," J Virol Methods. 61(1-2):151-6 (1996).

Langridge W.H. et al., "Uptake of DNA and RNA into cells mediated by electroporation," Methods Enzymol. 153:336-50. (1987).

Langridge, W.H. and , A.A.Szalay, "Bacterial and coelenterate luciferases as reporter genes in plant cells," Chapter 37 in Methods Mol Biol. 82:385-96.(1998).

Larson et al. "Triumph over mischance: a role for nuclear medicine in gene therapy," J Nucl Med. 38(8):1230-3 (1997).

Lawrence J.C., "The bacteriology of burns", J. of Hospital Infection 6: 3-17 (1985).

Lee et al., "The *lux* genes of the luminous bacterial symbiont *Photobacterium leiognathi*, of the ponyfish," Eur. J. Biochem. 201: 161-167 (1991).

Legocki et al., "Bioluminescence in soybean root nodules: Demonstration of a general approach to assay gene expression in vivo by using bacterial luciferase," Proc. Natl. Acad. Sci 83: 9080-9084 (1986).

Ley, K., "Integration of inflammatory signals by rolling neutrophils," Immunological Reviews, 186: 8-18 (2002).

Ley, K., "The role of selectins in inflammation and disease", Trends in Molec. Med., 9(6): 263-268 (2003).

Li et al "An engineered and assembled fusion protein of antitumor antibiotic lidamycin and scFV antibody directed against type IV collagenase" Yaoxue Xuebao 35(7) 488-91 (Jul. 2000) [English abstract on last page of article].

Lindvall et al., "Grafts of Fetal Dopamine Neurons Surive and Improve Motor Function in Parkinson's Disease," Science 237:574-577 (1990).

Liu, H et al., "Detection of GDNF secretion in glial cell culture and from transformed cell implants in the brains of live animals," Mol Genet Genomics. 266(4):614-23. (2001).

Liu, J. et al., "Visualizing and quantifying protein secretion using a *Renilla* luciferase-GFP fusion protein," Luminescence. 15(1):45-49 (2000).

Lorenz et al., "Isolation and expression of a cDNA encoding *Renilla reniformis* luciferase," PNAS USA 88: 4438-4442 (1991).

Lorenz et al., "Expression of the *Renilla reniformis* luciferase gene in mammalian cells," J Biolumin Chemilumin. 11(1):31-7 (1996).

Louie, A.Y. et al., "In vivo visualization of gene expression using magnetic resonance imaging," Nature Biotechnology, 18: 321-325 (2000).

Luscinskas, F.W. et al., "Leukocyte transendothelial migration: A junctional affair," Seminars in Immunology, 14: 105-113 (2002).

Luscinskas, F.W. et al., "The role of endothelial cell lateral junctions during leukocyte trafficking," Immunological Reviews, 186: 57-67 (2002).

Lusso, P., "Chemokines and Viruses: The Dearest Enemies," Virology, 273: 228-240 (2000).

Lyford, J., "Gene therapy 'cause T-cell leukemia': Insertional mutagenesis pinpointed as cause of T-cell Leukemia in X-SCID gene therapy trial," The Scientist, (Daily News, Oct. 20, 2003) pp. 1-4 (2003).

MacDonald, I.C. et al., "Cancer spread and micrometastasis development: quantitative approaches for in vivo models," BioEssays, 24: 885-893 (2002).

MacLaren et al. "Receptive non-invasive imaging of the dopamine D2 recepter gene in living animals" Gene Therapy 6: 785-791 (1995).

MacLeod R.A .et al., "Expression of genes from the marine bacterium *Alteromonas haloplanktis* 214 in *Escherichia coli* K-12," Arch Microbiol. 142(3):248-52 (1985).

Maeda, H. et al., "Tumor vascular permeability and the EPR effect in macromolecular therapeutics: a review", J. Controlled Release, 65: 271-284 (2000).

Mahy, B.W.J., "An overview on the use of a viral pathogen as a bioterrorism agent: why smallpox?", Antivir. Res., 57: 1-5 (2003).

Maina C.V. et al., "Molecular weight determination program," Nucleic Acids Res. 12(1 Pt 2):695-702 (1984).

Makower, D. et al., "Phase II Clinical Trial of Intralesional Administration of the Oncolytic Adenovirus ONYX-015 in Patients with Hepatobiliary Tumors with Correlative p53 Studies," Clin. Cancer Res., 9: 693-702 (2003).

Mastrangelo, M.J. et al., "Poxvirus vectors: orphaned and underappreciated," J. Clin. Invest, 105(8): 1031-1034 (2000).

Matz et al., "Fluorescent proteins from nonbioluminescent Anthozoa species," Nat.Biotech. 17: 969-973 (1999).

Mayerhofer, R et al., "Monitoring of spatial expression of firefly luciferase in transformed zebrafish," J Biolumin Chemilumin. 10(5):271-5 (1995).

McCart, J.A. et al., "Complex interactions between the replicating oncolytic effect and the enzyme/prodrug effect of vaccinia-mediated tumor regression," Gene Therapy, 7: 1217-1223 (2000).

McCart, J.A. et al., "Systemic Cancer Therapy with a Tumor-selective Vaccinia Virus Mutant Lacking Thymidine Kinase and Vaccinia Growth Factor Genes," Cancer Research, 61: 8751-8757 (2001).

McDonald, D.M. and P.L. Choyke, "Imaging of angiogenesis: from microscope to clinic," Nature Medicine, 9(6): 713-725 (2003).

Meager, A. et al., "The Development of the Regulatory Process in Europe for Biological Medicines: How it Affects Gene Therapy Products", Chapter 16 in *Gene Therapy Technologies, Applications and Regulations*, A. Meager (Ed.), John Wiley & Sons Ltd., pp. 319-346 (1999).

Meighen, E.A. and R.B. Szittner, "Multiple Repetitive Elements and Organization of the *lux* Operons of Luminescent Terrestrial Bacteria," J. Bacteriol. 174(16):5371-5381 (1992).

Mengaud et al., "Expression in *Escherichia coli* and Sequence Analysis of the Listeriolysin O Determinant of *Listeria monocytogenes*," Infect.Immun. 56(4): 766-772 (1988).

Middleton, J. et al., "Leukocyte extravasation: chemokine transport and presentation by the endothelium", Blood, 100(12): 3853-3860 (2002).

Moore et al. , "Measuring transferrin receptor gene expression by NMR imaging," Biochimica et Biophysica Acta 1402(3):239-249 (1998).

Moore, A.E., "Effects of Viruses on Tumors", Annu. Rev. Microbiol., 8: 393-402 (1954).

Morena, A., "Natural Killer Cells and Dendritic Cells: Rendezvous in Abused Tissues", Nat. Rev. Immunol., 2: 957-964 (2002).

Morris, D.W. et al., "Plasmid vectors capable of transferring large DNA fragments to yeast," DNA. 1(1):27-36 (1981).

Moss, B., "Poxviridae: the viruses and their replication," Chapter 84 in Field's Virology, $4^{th}$ Edn., vol. 2, pp. 2849-2883. Edited by D. M. Knipe and P. M. Howley, Philadelphia: Lippincott Williams & Wilkins, (2001).

Moss, B., "Poxviridae: the viruses and their replication," Chapter 83 in Fields Virology, 3rd Edn, pp. 2637-2671. Edited by B. N. Fields, D. M. Knipe & P. M. Howley. Philadelphia: Lippincott—Raven (1996).

Mountz et al. "Technetium-99m NeoTect imaging in vivo of T cells from hCAR transgenic mice," FASEB J. 16(5):A1211 March Meeting abstract (2002).

Nagahari et al. "Secretion into the culture medium of a foreign gene product from *Escherichia coli*: use of the *ompF* gene for secretion of human β-endorphin." EMBO J. 4(13A):3589-92 (1985).

Nettleton, P.F. et al., "Parapoxviruses are strongly inhibited in vitro by cidofovir," Antivir. Res., 48: 205-208 (2000).

Newton et al. "Expression and characterization of recombinant human eosinophil-derived neurotoxin and eosinophil-derived neurotoxin-anti-transferrin receptor sFv," J. Biol. Chem. 269(43):26739-45, (1994).

Neyts et al., "Therapy and short-term prophylaxis of poxvirus infections: historical background and perspectives," Antivir. Res. 57: 25-33 (2003).

Nibbering et al. "Radiolabelled antimicrobial peptides for imaging of infections: a review," Nucl Med Commun. 19(12):1117-21 (1998).

Nichterlein et al., "Clinafloxacin (CI 960) is Superior to Standard Therapeutics in the Treatment of Murine Listeriosis and Salmonellosis," Zentralbl.Bakteriol. 286: 401-412 (1997).

Nisato, R.E. et al., "Lymphangiogenesis and tumor metastasis", Thromb. Haemost., 90: 591-597 (2003).

Nolan G.P., et al., "Plasmid mapping computer program," Nucleic Acids Res. 12(1 Pt 2):717-29 (1984).

Noti J.D. et al., "Organization and characterization of genes essential for symbiotic nitrogen fixation from Bradyrhizobium japonicum 1110," J Bacteriol. 167(3):774-83 (1986).

Noti J.D. et al., "Site-directed Tn5 and transplacement mutagenesis: methods to identify symbiotic nitrogen fixation genes in slow-growing Rhizobium," Methods Enzymol. 154:197-217 (1987).

Ober, B.T. et al., "Immunogenicity and Safety of Defective Vaccinia Virus Lister:Comparison with Modified Vaccinia Virus Ankara", J. Virol., 76(15): 7713-7723 (2002).

O'Kane et al., "Visualization of Bioluminescence as a Marker of Gene Expression in Rhizobium-Infected Soybean Root Nodules," J. Plant Mol. Biol. 10: 387-399 (1988).

Olsson et al., "Engineering of monomeric bacterial luciferases by fusion of luxA and luxB genes in Vibrio harveyi," Gene 81(2):335-47 (1989).

Olsson, O. et al., "The use of the *luxA* gene of the bacterial luciferase operon as a reporter gene," Mol Gen Genet. 215(1):1-9 (1988).

Overholser et al., "Experimental Bacterial Endocarditis after Dental Extractions in Rats with Periodontitis," J. Infect. Dis. 155(1): 107-112 (1987).

Padera, T.P. et al., "Lymphatic Metastasis in the Absence of Functional Intratumor Lymphatics", Science 296: 1883-1886 (2002).

Paniacli, D. et al., "Vaccinia virus vectors utilizing the β-galactosidase assay for rapid selection of recombinant viruses and measurement of gene expression," Gene, 47: 193-199 (1986).

Pardal, R. et al., "Applying the principles of stem-cell biology to cancer," Nature Reviews Cancer, 3: 895-902 (2003).

Parish, C.R., "Cancer immunotherapy: The past, the present and the future," Immunology and Cell Biology, 81: 106-113 (2003).

Pawelek, J.M. et al., "Bacteria as tumour-targeting vectors," The Lancet Oncology, 4: 548-556 (2003).

Pecora, A.L. et al., "Phase I Trial of Intravenous Administration of PV701, an Oncolytic Virus, in Patients With Advanced Solid Cancers," Journal of Clinical Oncology, 20(9): 2251-2266 (2002).

Peplinski, G.R. et al., "Vaccinia Virus for Human Gene Therapy," Surgical Oncology Clinics of North America, 7(3): 575-588 (1998).

Pluen, A. et al., "Role of tumor—host interactions in interstitial diffusion of macromolecules: Cranial vs. subcutaneous tumors," Proc. Natl. Acad. Sci. U.S.A., 98(8): 4628-4633 (2001).
Polverini et al., "Assay and Purification of Naturally Occuring Inhibitor of Angiogenesis," Methods in Enzymology 198:440-450 (1991).
Pongor S. et al., "Microcomputer programs for prediction and comparative evaluation of protein secondary structure from nucleotide sequence data: application to ribulose-1,5-bisphosphate carboxylase sequences," DNA. 4(4):319-26 (1985).
Pongor S. and A.A. Szalay, "Prediction of homology and divergence in the secondary structure of Polypeptides," Proc Nat) Acad Sci U S A. 82(2):366-70 (1985).
Prasher et al., "Sequence Comparison of Complementary DNAs Encoding Aequorin Isotypes," Biochemistry 26: 1326-1332 (1987).
Prasher et al., "Primary structure of the Aequorea victoris green-fluorescent protein," Gene 111: 229-233(1992).
Proudfoot, A.E.I. et al., "Strategies for Chemokine Antagonists as Therapeutics," Seminars in Immunology, 15: 57-65 (2003).
Puhlmann et al. "Thymidine kinase-deleted vaccinia virus expressing purine nucleoside phosphorylase as a vector for tumor-directed gene therapy," Hum Gene Ther. 10(4):649-57 (1999).
Quenelle, D.C. et al., "Efficacy of Multiple- or Single-Dose Cidofovir against Vaccinia and Cowpox Virus Infections in Mice," Antimicrobial Agents and Chemotherapy, 47(10): 3275-3280 (2003).
Ramirez, J.C. et al., "Tissue distribution of the Ankara strain of vaccinia virus (MVA) after mucosal or systemic administration," Arch. Virol., 148: 827-839 (2003).
Rangarajan, A. and R.A. Weinberg, "Comparative biology of mouse versus human cells: modeling human cancer in mice," Nature Reviews Cancer, 3: 952-959 (2003).
Ransohoff, R.M. et al., "Three or more routes for leukocyte migration into the central nervous system,", Nat. Rev. Immunol., 3: 569-581 (2003).
Reddy et al. "Folate-mediated targeting of therapeutic and imaging agents to cancers," Crit Rev Ther Drug Carrier Syst. 15(6):587-627 (1998).
Reno, F., "Non-clinical Toxicology", Principles and Practice of Pharmaceutical Medicine, A.J. Fletcher et al.(eds.), ch.6: 55-64 (c2002) John Wiley & Sons Ltd.
Ribas, A. et al., "Current Developments in Cancer Vaccines and Cellular Immunotherapy," Journal of Clinical Oncology, 21(12): 2415-2432 (2003).
Ring, C.J.A., "Cytolytic viruses as potential anti-cancer agents," J. Gen. Virol., 83: 491-502 (2002).
Rodriguez, J.F. et al., "Expression of the firefly luciferase gene in vaccinia virus: A highly sensitive gene marker to follow virus dissemination in tissues of infected animals," Proc. Natl. Acad. Sci. U.S.A., 85: 1667-1671 (1988).
Rothenberg, M.L. et al., "Improving the evaluation of new cancer treatments: challenges and opportunities", Nat. Rev. Cancer, 3: 303-309 (2003).
Ruef et al. "Sternal wound infection after heart operations in pediatric patients associated with nasal carriage of Staphylococcus aureus" J. of Thoracic and Cardiovascular Surgery 112(3): 681-686 (1996).
Santoro, J. and M.E. Levison, "Rat Model of Experimental Endocarditis," Infect. Immun. 19(3): 915-918 (1978).
Schlör et al., "In vivo and in vitro studies on interactions between the components of the hemolysin (HlyA) secretion machinery of Escherichia coli," Mol.Gen.Genet. 256: 306-319 (1997).
Schmidt et al. "Generation of effective cancer vaccines genetically engineered to secrete cytokines using adenovirus-enhanced transferrinfection (AVET)," Gene. 190(1):211-6 (1997).
Shapiro, D. and A.W. Fox, "Biotechnology Products and Their Development", Principles and Practice of Pharmaceutical Medicine, A.J. Fletcher, et al.(eds.), ch.17: 191-201, c2002 John Wiley & Sons.
Shariatmadari et al., "Improved technique for detection of enhanced green fluorescent protein in transgenic mice," Biotechniques 30:1282-1285 (2001).
Shata, M.T. et al., "Optimization of recombinant vaccinia-based ELISPOT assay", J. Immunological Methods, 283: 281-289 (2003).
Shenk, T., "Delivery systems for gene therapy: the adenovirus", Stem Cell Biology and Gene Therapy, Quesenberry, P.J. et al. (Eds.), ch.6: pp. 161-178, c1998 Wiley-Liss, Inc.

Shepherd, A.J., "Good Laboratory Practice in the Research and Development Laboratory", Gene Therapy Technologies, Applications and Regulations, A. Meager (Ed.), ch.19: 375-381 (c1999) John Wiley & Sons Ltd.
Shimizu, Y. et al., "Immunotherapy of tumor-bearing mice utilizing virus help", Cancer Immunol. Immunother., 27: 223-227 (1988).
Sinkovics, J. and J. Horvath, "New Developments in the Virus Therapy of Cancer. A Historical Review", Intervirology, 36: 193-214 (1993).
Sinkovics, J.G. and J.C. Horvath, "Newcastle disease virus (NDV): brief history of its oncolytic strains", J. Clin. Virol., 16: 1-15 (2000).
Sinkovics, J.G. and J.C. Horvath, "Virus therapy of human cancers", Melanoma Research, 13: 431-432 (2003).
Smee, D.F. and R.W. Sidwell, "A review of compounds exhibiting anti-orthopoxvirus activity in animal models", Antiviral Research, 57: 41-52 (2003).
Smee, D.F. et al., "Effects of cidofovir on the pathogenesis of a lethal vaccinia virus respiratory infection in mice", Antivir. Res., 52: 55-62 (2001).
Smith, G.L. and B. Moss, "Infectious poxvirus vectors have capacity for at least 25000 base pairs of foreign DNA", Gene, 25: 21-28 (1983).
Smith, G.L. et al., "The formation and function of extracellular enveloped vaccinia virus", J. Gen. Virol., 83: 2915-2931 (2002).
Somia, N. and I.M. Verma, "Gene Therapy: Trial and Tribulations", Nat. Rev. Genet., 1(2): 91-99 (2000).
Spencer et al., "Unilateral Transplantation of Human Fetal Mesencephalic Tissue Into the Caudate Nucleus of Patients with Parkinson's Disease", New England Journal of Medicine 327: 1541-1548 (1992).
Stehle, G. et al., "Plasma protein (albumin) catabolism by the tumor itself—implications for tumor metabolism and the genesis of cachexia", Critical Reviews in Oncology/Hematology, 26: 77-100 (1997).
Stojdl, D.F. et al., "VSV strains with defects in their ability to shutdown innate immunity are potent systemic anti-cancer agents", Cancer Cell, 4:263-275 (2003).
Sudimack et al. "Targeted drug delivery via the folate receptor." Adv Drug Deliv Rev. 41(2):147-62 (2000).
Sutton et al. "In vivo adenovirus-mediated suicide gene therapy of orthotopic bladder cancer." Mol Ther. 2(3):211-7 (2000).
Suzuki M., Szalay A.A., "Bacterial transformation using temperature-sensitive mutants deficient in peptidoglycan synthesis," Methods Enzymol. 68:331-342 (1979).
Suzuki, S. et al. "Coexpression of the partial androgen receptor enhances the efficacy of prostate-specific antigen promoter-driven suicide gene therapy for prostate cancer cells at low testosterone concentrations," Cancer Research 61(4):1276-1279 (2001).
Symons, J.A. et al., "A study of the vaccinia virus interferon-y receptor and its contribution to virus virulence", Journal of General Virology, 83: 1953-1964 (2002).
Szalay A.A. et al., "Separation of the complementary strands of DNA fragments on polyacrylamide gels," Nucleic Acids Res. 4(5):1569-78 (1977).
Szalay A.A .et al, "Genetic engineering of halotolerance in microorganisms: a summary," Basic Life Sci. 14:321-32 (1979).
Technology Evaluation Center, "Special Report: Vaccines for the Treatment of Malignant Melanoma", TEC Assessment Program, 16(4): 1-46 (2001).
t'Hart, B.A. et al., "Gene thereapy in nonhuman primate models of human autoimmune disease", Gene Therapy, 10: 890-901 (2003).
Theuer et al., "A recombinant form of pseudomonas exotoxin directed at the epidermal growth factor receptor that is cytotoxic without requiring proteolytic processing," J.Biol.Chem. 267(24): 16872-16877 (1992).
Timiryasova, T.M. et al., "Antitumor Effect of Vaccinia Virus in Glioma Model", Oncology Research, 11(3): 133-144 (1999).
Timiryasova, T.M. et al., "Replication-deficient vaccinia virus gene therapy vector: evalution of exogenous gene expression mediated by PUV-inactivated virus in glioma cells", Journal of Gene Medicine, 3: 468-477 (2001).

Timiryasova, T.M. et al., "Vaccinia virus-mediated expression of wild-type p53 suppresses glioma cell growth and induces apoptosis." Int J Oncol. 14(5):845-54 (1999).

Timiryasova, T.M. et al., "Visualization of Vaccinia Virus Infection Using the Renilla-Luciferase-GFP Fusion Protein", Bioluminescence & chemiluminescence: Proceedings of the 11th International Symposium on Bioluminescence Chemiluminescence: Asilomar Conference Grounds, Pacific Grove, Monterey, California: Sep. 6-10, 2000 / (eds.): Case, J.F. et al., World Scientific Publishing Co. (c2001), pp. 457-460.

Timpl, "Antibodies to Collagens and Procollagens," Methods Enzymol. 82: 472-498 (1982).

Tjuvajev, J. et al., "*Salmonella*-based tumor-targeted cancer therapy: tumor amplified protein expression therapy (TAPET™) for diagnostic imaging," J. Controlled Release, 74: 313-315 (2001).

Toguchi et al., "Suicide Gene Therapy of C6 Glioma Cells Mediated by Replication-Deficient and Replication Competent Vaccinia Viruses," Cancer Gene Therapy 10: S32 (2003) presented at the Eleventh International Conference on Gene Therapy of Cancer, Dec. 12-14, 2002, San Diego California.

Tokugawa et al., "A model system for the continuous production of a heterologous protein using a novel secretion promoting factor which operates in *Escherichia coli*," J.Biotechnol. 37:33-37 (1994).

Tokugawa et al., "A novel protein secretion factor from a Vibrio species which operates in *Escherichia coli*," J.Biotechnol. 35: 69-76 (1994).

Tonetti DA et al "Stable transfection of an estrogen receptor beta cDNA isoform into MDA-MB-231 breast cancer cells," J Steroid Biochem Mol Biol. 87(1):47-55 (2003).

Tresco et al., "Polymer-encapsulated PC12 Cells: Long-Term Survival and Associated Reduction in Lesion-Induced Rotational Behavior", Cell Transplantation 1:255-264 (1992).

Tscharke, D.C. et al., "A model for vaccinia virus pathogenesis and immunity based on intradermal injection of mouse ear pinnae", J. Gen. Virol., 80: 2751-2755 (1999).

Tscharke, D.C. et al., "Dermal infection with vaccinia virus reveals roles for virus proteins not seen using other inoculation routes", Journal of General Virology, 83: 1977-1986 (2002).

Tseng, J.-C. et al., "In Vivo Antitumor Activity of Sindbis Viral Vectors", Journal of the National Cancer Institute, 94(23): 1790-1802 (2002).

Tseng, J.-C. et al., "Systemic tumor targeting and killing by Sindbis viral vectors", Nat. Biotechnol., 22(1): 70-77 (2004).

Tsung, K. et al., "Immune Response Against Large Tumors Eradicated by Treatment with Cyclophosphamide and IL-12", J. Immunol., 160: 1369-1377 (1998).

Vanderplasschen, A. et al., "Antibodies against vaccinia virus do not neutralize extracellular enveloped virus but prevent virus release from infected cells and comet formation", Journal of General Virology, 78: 2041-2048 (1997).

Vanderplasschen, A. et al., "Intracellular and extracellular vaccinia virions enter cells by different mechanisms", Journal of General Virology, 79: 877-887 (1998).

Varghese, S. and S.D. Rabkin, "Oncolytic herpes simplex virus vectors for cancer virotherapy", Cancer Gene Therapy, 9: 967-978 (2002).

Vento, S. and F. Cainelli, "Infections in patients with cancer undergoing chemotherapy: aetiology, prevention, and treatment", Lancet, 4: 595-604 (2003).

Vestweber, D., "Regulation of endothelial cell contacts during leukocyte extravasation", Curr. Opin. Cell Biol., 14: 587-593 (2002).

Vile, R. et al., "The oncolytic virotherapy treatment platform for cancer: Unique biological and biosafety points to consider", Cancer Gene Therapy, 9: 1062-1067 (2002).

Vogel, J.R., "Outsourcing Clinical Drug Development Activities to Contract Reseach Organizations (CROs): Critical Success Factors", Principles and Practice of Pharmaceutical. Medicine, A.J. Fletcher et al.(eds.), ch.40: 461-482 (c2002) John Wiley & Sons Ltd.

Voisey et al. Elimination of internal restriction enzyme sites from a bacterial luminescence (luxCDABE) operon. Biotechniques 24(1):56, 58 (1998).

Wallack, M.K. et al., "A Phase III Randomized, Double-Blind, Multiinstitutional Trial of Vaccinia Melanoma Oncolysate-Active Specific Immunotherapy for Patients with Stage II Melanoma", Cancer, 75(1): 34-42 (1995).

Wallack, M.K. et al., "Increased Survival of Patients Treated With a Vaccinia Melanoma Oncolysate Vaccine", Annals of Surgery, 226(2): 198-206 (1997).

Wallack, M.K. et al., "Surgical Adjuvant Active Specific Immunotherapy for Patients with Stage III Melanoma: The Final Analysis of Data From a Phase III, Randomized, Double-Blind, Multicenter Vaccinia Melanoma Oncolysate Trial", J. Am. Coll. Surg., 187(1): 69-79 (1998).

Wang Y. et al., "A study of protein-protein interactions in living cells using luminescence resonance energy transfer (LRET) from *Renilla* luciferase to *Aequorea* GFP," Mol Gen Genet. 264(5):578-87 (2001).

Wang Y. et al., "*Renilla* luciferase—Aequorea GFP (Ruc-GFP) fusion protein, a novel dual reporter for real-time imaging of gene expression in cell cultures and in live animals," Mol Genet Genomics. 268(2):160-8.(2002).

Wang, Y. et al., "The *Renilla* Luciferase-Modified GFP Fusion Protein is Functional in Transformed Cells", Bioluminescence & chemiluminescence: Proceedings of the 9th International Symposium on Bioluminescence Chemiluminescence: Woods Hole, Massachusetts, Oct. 1996 / (eds.) Hastings, J.W. et al., John Wiley & Sons Ltd., pp. 419-422 (c1997).

Warrington et al. "Developing VDEPT for DT-diaphorase (NQO1) using an AAV vector plasmid," Int J Radiat Oncol Biol Phys. 42(4):909-12 (1998).

Wegner et al., "Cis-acting suquences from mouse rDNA promote plasmid DNA amplification and persistence in mouse cells: implication of HMG-I in their function", Nucleic Acids Research 17:9909-9932 (1989).

Weissleder et al. "Drug targeting in magnetic resonance imaging," Magnetic Resonance Quarterly. 8(1):55-63 (1992).

Weissleder, T. et al., "In vivo magnetic resonance imaging of transgene expression", Nat. Med. , 6(3): 351-354 (2000).

Welling et al "Technetium-99m labelled antimicrobial peptides discriminate between bacterial infections and sterile inflammations." Eur J Nucl Med. 27(3):292-301 (2000).

Welling et al "Radiochemical and biological characteristics of 99mTc-UBI 29-41 for imaging of bacterial infections." Nucl Med Biol. 29(4):413-22 (2002).

West et al. "Identification of a somatodendritic targeting signal in the cytoplasmic domain of the transferrin receptor." J Neurosci. 17(16):6038-47 (1997).

Wharton, M. et al., "Recommendations for Using Smallpox Vaccine in a Pre-Event Vaccination Program", MMWR, 52(RR-7): 1-16 (2003).

Whitley, R.J., "Smallpox: a potential agent of bioterrorism", Antiviral Research 57: 7-12 (2003).

Williams J.G. and Szalay A.A., "Stable integration of foreign DNA into the chromosome of the cyanobacterium *Synechococcus* R2," Gene. 24(1):37-51 (1983).

Winn et al., "Behavioral Recovery following Intrastriatal Implantation of Microencapsulated PC12 Cells", Experimental Neurology 113:322-329 (1991).

Winn, S.R. et al., Polymer-encapsulated cells genetically modified to secrete human nerve growth factor promote the survival of axotomized septal cholinergic neurons, Proceedings of the National Academy of Science, 91:2324-2328 (1994).

Wisher, M., "Biosafety and product release testing issues relevant to replication-competent oncolytic viruses", Cancer Gene Therapy, 9: 1056-1061 (2002).

Wittrup, D., "Tumor Targeting Theory", IBC's 15th Annual International Antibody Engineering Conference entitled Antibody Engineering: Forging the Future of Antibody Therapeutics, Nov. 30,-Dec. 3, 2003—The Paradise Point Resort—San Diego, CA, pp. 1-17.

Wlodaver, C.G. et al., "Laboratory-acquired vaccinia infection", Journal of Clinical Virology, xxx: 1-5 (2003).

Wong, M.M. and E.N. Fish, "Chemokines: attractive mediators of the immune response", Semin. Immunol. 15: 5-14 (2003).

Yadav, R. et al., "Migration of leukocytes through the vessel wall and beyond," Thromb. Haemost., 90: 598-606 (2003).

Yansura, D.G. and Henner D.J.; "Use of the *Escherichia coli* lac repressor and operator to control gene expression in *Bacillus subtilis*," Proc. Natl. Acad. Sci USA 81: 439-443 (1984).

Yu Y.A., "Visualization of molecular and cellular events with green fluorescent proteins in developing embryos: a review," Luminescence. 18(1):1-18 (2003) Erratum in: Luminescence. 2003 Jul.-Aug.; 18(4):243.

Yu Y.A. et al., "A *Renilla* luciferase-*Aequorea* GFP (*ruc-gfp*) fusion gene construct permits real-time detection of promoter activation by exogenously administered *mife*pristone in vivo," Mol Genet Genomics. 268(2):169-78 (2002).

Yu Y.A. et al., "Optical imaging: bacteria, viruses, and mammalian cells encoding light-emitting proteins reveal the locations of primary tumors and metastases in animals,"Anal Bioanal Chem. 377(6):964-72 (2003).

Yu, Y.A. et al. "Visualization of tumors and metastases in live animals with bacteria and vaccinia virus encoding light-emitting proteins," Nat Biotech. 22(3): 313-320 (2004).

Yun A.C. et al. "Nitrogenase promoter-*lacZ* fusion studies of essential nitrogen fixation genes in *Bradyrhizobium japonicum* 1110," J Bacteriol. 167(3):784-91 (1986).

Zamir et al. "Stable chromosomal integration of the entire nitrogen fixation gene clusterfrom *Klebsiella pneumoniae* in yeast," Proc Natl Acad Sci U S A. 78(6):3496-500 (1981).

Zaucha, G.M. et al., "The Pathology of Experimental Aerosolized Monkeypox Virus Infection in Cynomolgus Monkeys (*Macaca fascicularis*)", Lab. Invest., 81: 1581-1600 (2001).

Zeh, H.J. and D.L. Bartlett, "Development of a replication-selective, oncolytic poxvirus for the treatment of human cancers", Cancer Gene Therapy, 9: 1001-1012 (2002).

Zhang et al., "Urothelium-specific Expression of an Oncogene in Transgenic Mice Induced the Formation of Carcinoma in Situ and Invasive Transitional Cell Carcinoma," Cancer Res.59: 3512-3517 (1999).

Zhu et al., "*Smad3* Mutant Mice Develop Metastatic Colorectal Cancer," Cell 94: 703-714 (1998).

Zinkernagel, R.M., "Uncertainties—discrepancies in immunology," Immunological Reviews 185: 103-125 (2002).

Zinn et al., "Simulataneous evaluation of dual gene transfer to adherent cells by gamma-ray imaging," Nuclear Medicine and Biology 28(2):135-144 (2001).

Zinn et al. "Noninvasive monitoring of gene transfer using a reporter receptor imaged with a high-affinity peptide radiolabeled with 99mTc or 188Re," J Nucl Med. 41(5):887-895 (2000).

Contag et al., "Visualizing Gene Expression in Living Mammals Using a Bioluminescent Reporter," Photochemistry and Photobiology 66(4):523-531 (1997).

Fu et al., "Relationship between gut origin bacteria and wound infection after thermal injury," Zhonghua Wai Ke Za Zhi 32(10):615-618 (1994).

English Translation of Fu et al., "Relationship between gut origin bacteria and wound infection after thermal injury," from the Chinese, Zhonghua Wai Ke Za Zhi 32(10):615-618 (1994).

Gelfand et al., "Infections in burn patients: a paradigm for cutaneous infection in the patient as risk," American Journal of Medicine 76(5A):158-165 (1984).

Huang et al., "Bacterial penetration across the blood-brain barrier during the development of neonatal meningitis," Microbes and Infection 2(10):1237-1244 (2000).

Lu et al., "Delivery of adenoviral vectors to the prostate for gene therapy," Cancer Gene Therapy 6(1):64-72 (1999).

Perkus et al., "Deletion of 55 open reading frames from the termini of vaccinia virus," Virology 180:406-410 (1991).

Weissleder et al., "In vivo imaging of tumors with protease-activated near-infrared fluorescent probes," Nature Biotechnology 17:375-378 (1999).

Weng et al., "HO-1 expression in type II pneumocytes after transpulmonary gene delivery," American Journal of Physiology. Lung Cellular and Molecular Physiology 278:L1273-L1279 (2000).

Demkowicz et al., "Human Cytotoxic T-Cell Memory: Long-Lived Responses to Vaccinia Virus," J. Virol. 70(4):2627-2631 (1996).

Lopez-Guerrero et al., "Therapeutic Effect of Recombinant Vaccinia Virus Expressing the 60-kd Heat Shock Protein on Adjuvant Arthritis," Arthr Rheum 37(10):1462-1467 (1994).

Orkin et al., "Report and Recommendations of the Panel to Assess the NIH Investment in Research on Gene Therapy," (1995).

Stienlauf et al., "Kinetics of formation of neutralizing antibodies against vaccinia virus following re-vaccination," Vaccine 17:201-204 (1999).

European Summons to Attend Oral Proceedings, mailed Sep. 27, 2010, in connection with European Patent Application No. 03735553.4.

Amendment and response to European Summons to Attend Oral Proceedings, filed Nov. 26, 2010, in connection with European Patent Application No. 03735553.4.

Communication from European Patent Office cancelling the Summons to Attend Oral Proceedings, issued Dec. 7, 2010, in connection with European Patent Application No. 03735553.4.

Singapore Examination Report, issued Oct. 18, 2010, in connection with Singapore Patent Application No. 200701613-2.

Howard et al., "Molecular mimicry of the inflammation modulatory proteins (IMPs) of poxviruses: evasion of the inflammatory response to preserve viral habitat," J. Leukocyte Biol. 64:68-71 (1998).

Menkin, "Studies on inflammation: VII. Fixation of bacteria and of particulate matter at the site of inflammation," J. Exp. Med. 53:647-660 (1931).

Office Action, issued Nov. 28, 2007, in connection with U.S. Appl. No. 10/849,664.

U.S. Appl. No. 11/982,102, filed Oct. 31, 2007.
U.S. Appl. No. 11/982,040, filed Oct. 31, 2007.
U.S. Appl. No. 11/981,976, filed Oct. 31, 2007.
U.S. Appl. No. 11/982,035, filed Oct. 31, 2007.

Certified English translation of DE 44 25 382 A1, published Jan. 25, 1996, entitled: "Method for detection of live bacterial vectors." [Patent in German].

Examination Report, issued Jan. 30, 2008, in connection with European Patent Application No. 02012552.2.

Examination Report, issued Feb. 1, 2008, in connection with corresponding Chinese Patent Application No. 03812787.3.

Office Action, issued Mar. 18, 2008, in connection with U.S. Appl. No. 10/866,606.

U.S. Appl. No. 12/148,542, filed Apr. 17, 2008.
U.S. Appl. No. 12/081,766, filed Apr. 4, 2008.
U.S. Appl. No. 12/156,135, filed May 30, 2008.
PCT/US2008006917, May 30, 2008.
U.S. 157,960, filed Jun. 13, 2008.
PCT/US2008/07377, filed Jun. 13, 2008.

Certified English language translation of abstract and summary for Japanese Journal of Clinical and Experimental Medicine 66:1877-1880 (1989).

Derwent English Abstract for Japanese Patent Publication JP 2000295987, published Oct. 24, 2000, entitled, "Transdifferentiation of Transfected Epidermal Basal Cell Into Neutral Progenitor Cell, Neuronal Cell and/or Glial Cell," (9 pages) Derwent Accession No. 10188304.

Hermiston, T and D. Kim, "Genetically based therapeutics for cancer: similarities and contrasts with traditional drug discovery and development," Mol. Ther. 11(4):496-507 (2005).

Japanese Journal of Clinical and Experimental Medicine 66:1877-1880 (1989). [in Japanese].

Kruis W., "Review article: antibiotics and probiotics in inflammatory bowel disease," Pharmacol. Ther. 20 (Suppl 4): 75-78 (2004).

Meighen et al., "Molecular Biology of Bacterial Bioluminescence", Microbiological Reviews 55(1):123-142 (1991).

Riedel et al., "Improved luciferase tagging system for listeria monocytogenes allows real-time monitoring in vivo and in vitro," Appl. Environ. Microbiol. 73:3091-3094 (2007).

Sumii et al., "A Case of *salmonella* prostatitis in a renal transplant patient," Journal of the Japanese Association for Infectious Diseases 60:624-626 (1986). [in Japanese language with English language summary].

Taubes et al., "Firefly gene lights up lab animals inside out," Science 276(5321):1993 (1997).

Examination Report, issued Oct. 26, 2005, in connection with European Patent Application No. 02012552.2.

Examination Report, issued Jun. 22, 2007, in connection with European Patent Application No. 03735553.4.

Office Action, issued Jun. 13, 2006, in connection with U.S. Appl. No. 10/849,664.

Office Actions, issued Mar. 12, 2007, in connection with U.S. Appl. No. 10/849,664.

Office Action, issued Oct. 4, 2007, in connection with Canadian Patent Application No. 2,456,055.

"Definition of Tumor", MedicineNet.com, www.medterms.com/script/main/art.asp?articlekey=5863 (Accessed on May 30, 2007).

U.S. Appl. No. 11/529,662, filed Sep. 27, 2006.

U.S. Appl. No. 11/796,028, filed Apr. 25, 2007.

U.S. Appl. No. 11/796,027, filed Apr. 25, 2007.

U.S. Appl. No. 10/849,664, filed May 19, 2004.

U.S. Appl. No. 11/827,518, filed Jul. 11, 2007.

U.S. Appl. No. 11/975,088, filed Oct. 16, 2007.

U.S. Appl. No. 11/975,090, filed Oct. 16, 2007.

Translation of Official Action, issued Dec. 19, 2010, in connection with corresponding Israeli Patent Application 165350 [1 page].

Notice of Grant, issued Feb. 2, 2011, in connection with corresponding European Patent Application Serial No. 03735553.4 [4 pages].

Letter/Written Disclosure of the Information Disclosure Statement for the above-referenced application (U.S. Appl. No. 10/516,785), filed Sep. 29, 2009, 4 pages.

Letter/Written Disclosure of the Information Disclosure Statement for the above-referenced application (U.S. Appl. No. 10/516,785), filed Apr. 13, 2010, 3 pages.

Official Action, issued Dec. 3, 2008, in connection with Israeli Patent Application No. 165350.

Official Action, issued Jan. 27, 2009, in connection with Japanese Patent Application No. 2004-511544.

Official Action, issued Mar. 30, 2009, in connection with Canadian Patent Application No. 2,488,227.

Official Action, issued Jun. 26, 2009, in connection with Chinese Patent Application No. 03812787.3.

Amato et al., "Luminous with promise," Chem. Eng. News. 84(49):69-73 (2006).

Loessner et al., "Remote control of tumour-targeted *Salmonella enterica* serovar Typhimurium by the use of L-arabinose as inducer of bacterial gene expression in vivo," Cell. Microbiol. 9(6):1529-1537 (2007).

Loessner et al., "Drug-inducible remote control of gene expression by probiotic *Escherichia coli* Nissle 1917 in intestine, tumor and gall bladder of mice," Microb. Infect. Published online: Aug. 7, 2009.

Westphal et al., "Containment of tumor-colonizing bacteria by host neutrophils," Cancer Res. 68(8):2952-2960.

Search Report and Written Opinion, issued Sep. 22, 2009, in connection with Singapore Patent Application No. 20070163-2.

Official Notification, issued Jul. 31, 2011, in connection with Israeli Patent Application No. 165350. 16 pages.

Notice of Acceptance, issued Mar. 9, 2011, in connection with Australian Patent Application No. 2008202946, 3 pages.

* cited by examiner

Figure 1
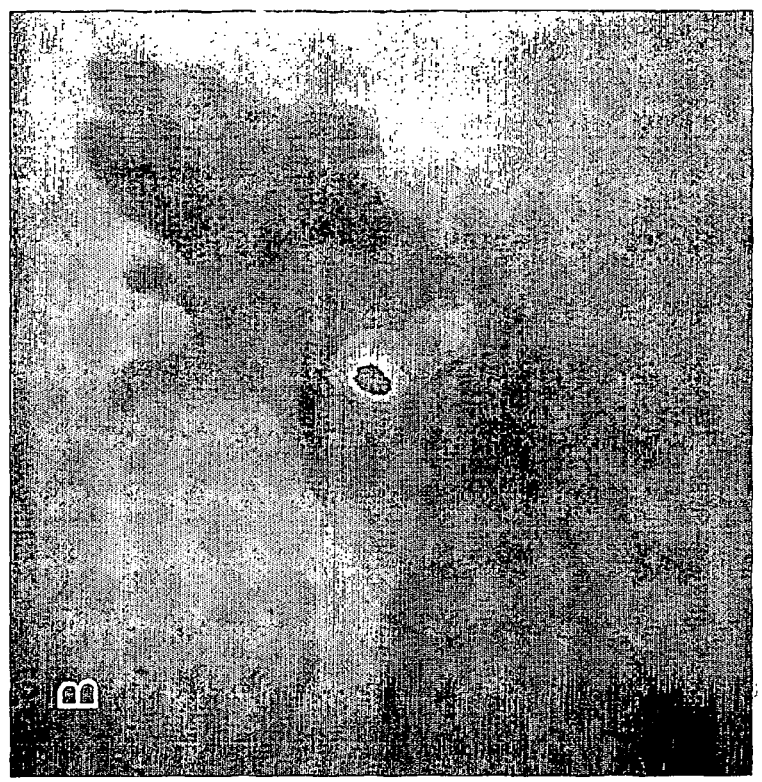
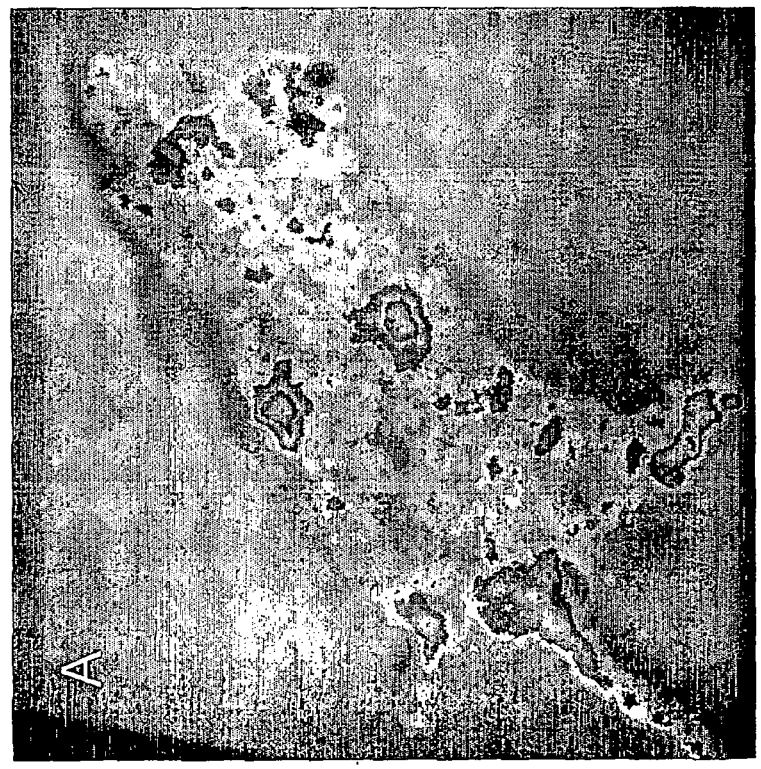
i.v. injection of *Salmonella* into nude mice
i.v. injection of *Vibrio* in nude mouse Figure 2. i.v. injection of *Salmonella* into nude mouse Figure 4. Immunocompetent C57 mouse injected i.v. with *Vibrio*

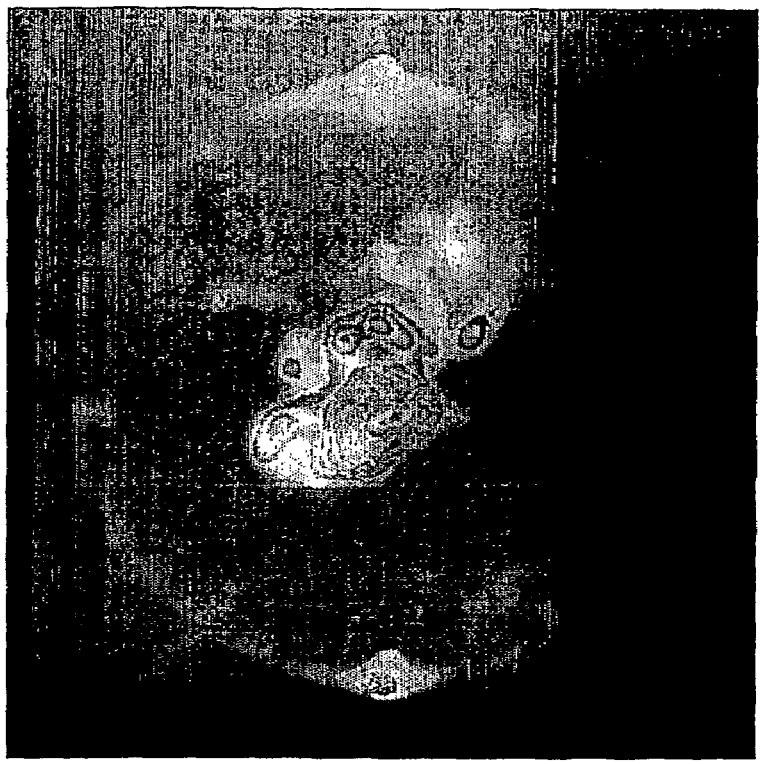
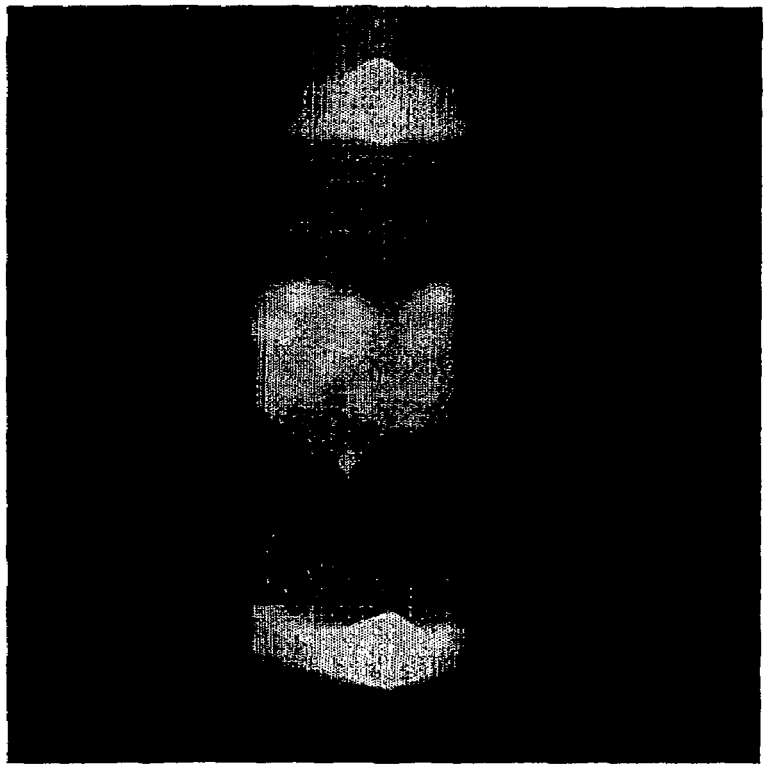
Figure 6

LIGHT EMITTING MICROORGANISMS AND CELLS FOR DIAGNOSIS AND THERAPY OF DISEASES ASSOCIATED WITH WOUNDED OR INFLAMED TISSUE

This application is the National Stage of International Application. No. PCT/EP03/05907, filed 5 Jun. 2003, and claims benefit of priority under 35 U.S.C. §365(b) to European Patent Application No. 02012552.2, filed 5 Jun. 2002. The subject matter of the above-noted applications is incorporated herein by reference in its entirety.

The present invention relates to the use of a microorganism or cell containing a DNA sequence encoding a detectable protein or a protein capable of inducing a detectable signal, e.g. a luminescent or fluorescent protein, for the preparation of a diagnostic composition for diagnosis and/or visualization of wounded or inflamed tissue or a disease associated therewith. The present invention also relates to therapeutic uses wherein said microorganism or cell additionally contain an expressible DNA sequence encoding a protein suitable for therapy, e.g. an enzyme causing cell death or digestion of debris.

Bacteremias may arise from traumatic injuries and surgical procedures as well as from physiological functions, such as chewing or tooth brushing. Blood cultures taken before and after invasive procedures and physiological functions from healthy human subjects show that while the premanipulation blood samples are sterile, bacteria are present in the blood in varying frequencies depending on the procedures. A potential consequence of bacteremia is colonization of susceptible sites. However, despite the occurrence of transient bacteremias, only a certain percentage of high-risk patients develop bacterial colonization of potentially susceptible sites. A number of investigators have suggested that bacteria from the blood circulation can colonize inflamed tissues in animal models and on the surface of implanted materials. The inconsistency in the pathological changes in humans following a bacteremia may also be due to the resistance of host immune system, the variability in the concentration of bacteria in the blood subsequent to different bacteremia events, and the virulence of any given bacterial strain.

A number of investigators have focused on the nature of the implanted materials as the factor that influences the ability of bacteria to adhere. Materials such as sutures and surgical clips which are used for closure of wounds, are potential sites of bacterial colonization. Infection of these materials may impede wound healing and/or place patients at increased risk of secondary infections. A variety of wound closure materials have been manufactured with varying affinities for bacteria. Certain wound closure materials, such as braided sutures, have been associated with a higher incidence of infection. The multifilament nature of this type of suture material lends itself to increased susceptibility to bacterial colonization as well as causing a wicking effect that allows penetration of bacteria across the tissues. Mere permanent implantable materials have demonstrated a similar affinity for bacteria. Prosthetic heart valves and joints may be at increased risk of bacterial colonization. It is commonly believed that this higher susceptibility is caused by the inherent ability of bacteria to adhere more readily to the implant surfaces. An alternative explanation may be that inflammation in the tissues surrounding the implants provides an environment that is more suitable for bacterial colonization. In addition to these given possibilities, another factor that may influence the susceptibility of a site, with regards to colonization with bacteria could be the degree of inflammatory status of the affected tissues. Implanted materials may create transient or chronic sites of inflammation in the body.

Presence of implanted materials is not a requirement for bacterial colonization. Alteration of natural anatomical structures that may arise from disease conditions may produce surfaces that are easier to colonize by bacteria. It had been suggested that for the occurrence of infective endocarditis (IE), the valve surface must be altered in order to produce a suitable site for bacterial attachment and colonization. Additionally, the microorganisms have to reach this site and adhere, since it is not possible to produce IE in experimental animals with injections of bacteria unless the valvular surface is damaged. Lesions with high turbulence create conditions that lead to bacterial colonization, whereas defects with a large surface area or low flow are seldom implicated in IE.

However, so far, it could not be proven that transient bacteremias actually cause colonization of inflamed or wounded tissue, since there was no model available allowing the tracing of bacteria in a living organism, i.e. allowing to explain the temporal and spatial relationship between bacterial infections and diseased tissue sites. Moreover, unfortunately, so far the early diagnosis and therapy of inflamed or wounded tissues or diseases associated therewith, e.g., an atherosclerotic disease, endocarditis, pericarditis etc., are unsatisfactory.

Therefore, it is the object of the present invention to provide a means for the efficient and reliable diagnosis as well as the therapy of wounded or inflamed tissue or a disease associated therewith which overcomes the disadvantages of the diagnostic and therapeutic approaches presently used.

According to the present invention this is achieved by the subject matters defined in the claims. In the experiments leading to the present invention it has been found that inflamed tissues, e.g. near implanted material, permit bacterial colonization. Therefore, it is generally possible to visualize inflamed tissues through use of the system of the present invention described below. It could be shown that expression of genes encoding light-emitting proteins in bacteria provides a genetic tool that allows the tracing of the bacteria in a living host, i.e. the evaluation of the dynamics of an infection process in a living host. The external detection of light-emitting bacteria allowed the inventors to non-invasively study the spatial and temporal relationships between infections and the manifested disease conditions. For generation of the light-emitting bacteria, the bacterial luxab operon was used which encodes the enzyme luciferase which catalyzes the oxidation of reduced flavin mononucleotide (FMNE2), in the presence of the substrate, decanal. This reaction then yields FMN, decanoic acid, water and a photon of light. The light photons can then be captured by radiographs, luminometers, or by low light imagers. Recently, the entire bacterial luxcdabe operon, which encodes the substrate as well as the luciferase enzyme, has been used for detection of bacteria in living animals. The advantage of this system is that it does not require exogenously added substrate, which makes it ideal for in vivo studies.

In the studies leading to the present invention, the colonization of wounded and inflamed tissue by bacteria initially present in the circulating blood could be demonstrated and it could be shown that tissues that are irritated by implanted materials such as sutures, wound closure clips and prosthetic devices are more susceptible to bacterial colonization subsequent to bacteremias. The data obtained from experiments with the attenuated *S. typhimurium* shows that following an intravenous injection, bacteria disseminate throughout the body of the live animals. Therefore, it is reasonable to suggest that the bacteria reach the wounded or inflamed sites via the circulation. These findings described in detail in the examples, below, open the way for (a) designing multifunctional viral vectors useful for the detection of wounded or inflamed tissue based on signals like light emission or signals that can be visualised by MRI and (b) the development of bacterium- and mammalian cell-based wounded or inflamed tissue targeting systems in combination with therapeutic gene constructs for the treatment of diseases associated with wounded or inflamed tissue such as, e.g., an atherosclerotic disease. These systems have the following advantages: (a) They target the wounded or inflamed tissue specifically without affecting normal tissue; (b) the expression and secretion of the therapeutic gene constructs are, preferably, under the control of an inducible promoter, enabling secretion to be switched on or off; and (c) the location of the delivery system inside the tissue can be verified by direct visualisation before activating gene expression and protein delivery. Finally, there are a number of diagnostic methods that could be enhanced or advantageously replaced by the diagnostic approach of the present invention. For example, conventional angiography and MRA techniques and MRA techniques both image blood flowing through the lumen of a vessel to visualize plaque, rather than imaging the plaque directly. MRA is particularly sensitive to turbulence caused by the plaque and, as a result, is often inaccurate. These shortcomings can be overcome by the diagnostic uses of the present invention.

Accordingly, the present invention relates to the use of a microorganism or cell containing a DNA sequence encoding a detectable protein or a protein capable of inducing a detectable signal for the preparation of a diagnostic composition for diagnosis and/or visualization of wounded or inflamed tissue or a disease associated therewith. In addition, said microorganism is also useful for therapy, since following visualization of wounded or inflamed tissue compounds suitable for therapy can be applied, e.g. by topical administration, such as, e.g., acylated iridoid glycosides from *Scrophularia nodosa*, cortisol, corticosteroid analogs, colchicine, methotrexate, non-steroidal anti-inflammatory drugs (NSAIDs), leflunomide, etanercept, minocycline, cyclosporine, thalidomide, a cytotoxic agent, 6-mercaptopurine, azathioprine, antibiotics or one or more of the proteins listed below.

The present invention also relates to the use of a microorganism or cell containing a DNA sequence encoding a detectable protein or a protein capable of inducing a detectable signal for the preparation of a pharmaceutical composition for the treatment of wounded or inflamed tissue or a disease associated therewith, wherein said micoroorganism or cell furthermore contains one or more expressible DNA sequences encoding (a) proteine(s) suitable for the therapy of wounded or inflamed tissue or diseases associated therewith.

Proteins suitable for the therapy of wounded or inflamed tissue or diseases associated therewith include transforming growth factor (TGF-alpha), platelet-derived growth factor (PDG-F), keratinocyte growth factor (KGF) and insulin-like growth factor-1 (IGF-1), insulin-like growth factor-binding proteins (IGFBPs), IL-4, IL-8, endothelin-1 (ET-1), connective tissue growth factor (CTGF), TNF-alpha, vascular endothelial growth factor (VEGF), cyclooxygenase, cyclooxygenase-2 inhibitor, infliximab (a chimeric anti-TNF-alpha monoclonal antibody), IL-10, lipase, protease, lysozyme, pro-apoptotic factor, peroxisome proliferator-activated receptor (PPAR) agonist etc.

Any microorganism or cell is useful for the diagnostic and therapeutic uses of the present invention, provided that it replicates in the organism, is not pathogenic for the organism e.g. attenuated and, is recognized by the immune system of the organism, etc. The terms "microorganism" and "cell" as used herein refer to microorganisms and cells which are per se not targeted to wounded or inflamed tissues (i.e. they cannot differentiate between wounded or inflamed tissues and the non-wounded or non-inflamed counterpart tissues) since the results of the experiments leading to the present invention show that microorganisms and cells accumulate in wounded or inflamed tissues due to the fact that in this environment they are not exposed to attack by the immune system of the host. The microorganisms and cells accumulate for a specific time, e.g. 3 to 5 days, as long as the vascularization/lymphatic system has not been restored.

In a preferred embodiment, the microorganism or cell contains a DNA sequence encoding a luminescent and/or fluorescent protein. As used herein, the term "DNA sequence encoding a luminescent or fluorescent protein" also comprises a DNA sequence encoding a luminescent and fluorescent protein as fusion protein.

In an alternative preferred embodiment of the use of the present invention, the microorganism or cell contains a DNA sequence encoding a protein capable of inducing a signal detectable by magnetic resonance imaging (MRI), e.g. a metal binding protein. Furthermore, the protein can bind a contrasting agent, chromophore, or a compound required for visualization of tissues.

Suitable devices for analysing the localization or distribution of luminescent and/or fluorescent proteins in a tissue are well known to the person skilled in the art and, furthermore described in the literature cited above as well as the examples, below.

Preferably, for transfecting the cells the DNA sequences encoding a detectable protein or a protein capable of inducing a detectable signal, e.g., a luminescent or fluorescent protein, are present in a vector or an expression vector. A person skilled in the art is familiar with examples thereof. The DNA sequences can also be contained in a recombinant virus containing appropriate expression cassettes. Suitable viruses that may be used include baculovirus, vaccinia, sindbis virus, Sendai virus, adenovirus, an AAV virus or a parvovirus, such as MVM or H-1. The vector may also be a retrovirus, such as MoMULV, MoMuLV, HaMuSV, MuMTV, RSV or GaLV. For expression in mammals, a suitable promoter is e.g. human cytomegalovirus "immediate early promoter" (pCMV). Furthermore, tissue and/or organ specific promoters are useful. Preferably, the DNA sequences encoding a detectable protein or a protein capable of inducing a detectable signal are operatively linked with a promoter allowing high expression. Such promoters, e.g. inducible promoters are well-known to the person skilled in the art.

For generating the above described DNA sequences and for constructing expression vectors or viruses which contain said DNA sequences, it is possible to use general methods known in the art. These methods include e.g. in vitro recombination techniques, synthetic methods and in vivo recombination methods as described in Sambrook et al., Molecular Cloning, A Laboratory Manual, $2^{nd}$ edition (1989) Cold Spring Harbor Laboratory Press, Cold Spring Harbor, N.Y., for example. Methods of transfecting cells, of phenotypically selecting transfectants and of expressing the DNA sequences by using the above described vectors are known in the art.

The person skilled in the art knows DNA sequences encoding luminescent or fluorescent proteins that can be used for carrying out the present invention. During the past decade, the identification and isolation of structural genes encoding light-emitting proteins from bacterial luciferase from *Vibrio harveyi* (Belas et al., Science 218 (1982), 791-793) and from *Vibrio fischerii* (Foran and Brown, Nucleic acids Reds. 16 (1988), 177), firefly luciferase (de Wet et al., Mol. Cell. Biol.

7 (1987), 725-737), aequorin from *Aequorea victoria* (Prasher et al., Biochem. 26 (1987), 1326-1332), *Renilla* luciferase from *Renilla reniformis* (Lorenz et al., PNAS USA 88 (1991), 4438-4442) and green fluorescent protein from *Aequorea victoria* (Prasher et al., Gene 111 (1987), 229-233) have been described that allow the tracing of bacteria or viruses based on light emission. Transformation and expression of these genes in bacteria allows detection of bacterial colonies with the aid of the low light imaging camera or individual bacteria under the fluorescent microscope (Engebrecht et al., Science 227 (1985), 1345-1347; Legocki et al., PNAS 83 (1986), 9080-9084; Chalfie et al., Science 263 (1994), 802-805).

Luciferase genes have been expressed in a variety of organisms. Promoter activation based on light emission, using luxAB fused to the nitrogenase promoter, was demonstrated in Rhizobia residing within the cytoplasm of cells of infected root nodules by low light imaging (Legocki et al., PNAS 83 (1986), 9080-9084; O'Kane et al., J. Plant Mol. Biol. 10 (1988), 387-399). Fusion of the lux A and lux B genes resulted in a fully functional luciferase protein (Escher et al., PNAS 86 (1989), 6528-6532). This fusion gene (Fab2) was introduced into *Bacillus subtilis* and *Bacillus megatherium* under the xylose promoter and then fed into insect larvae and was injected into the hemolymph of worms. Imaging of light emission was conducted using a low light video camera. The movement and localization of pathogenic bacteria in transgenic arabidopsis plants, which carry the pathogen-activated PAL promoter-bacterial luciferase fusion gene construct, was demonstrated by localizing *Pseudomonas* or *Ervinia* spp. infection under the low light imager as well as in tomato plant and stacks of potatoes (Giacomin and Szalay, Plant Sci. 116 (1996), 59-72).

Thus, in a more preferred embodiment, the luminescent or fluorescent protein present in the above described microorganism or cell is luciferase, RFP or GFP.

All of the luciferases expressed in bacteria require exogenously added substrates such as decanal or coelenterazine for light emission. In contrast, while visualization of GFP fluorescence does not require a substrate, an excitation light source is needed. More recently, the gene cluster encoding the bacterial luciferase and the proteins for providing decanal within the cell, which includes luxCDABE was isolated from *Xenorhabdus luminescens* (Meighen and Szittner, J. Bacteriol. 174 (1992), 5371-5381) and *Photobacterium leiognathi* (Lee et al., Eur. J. Biochem. 201 (1991), 161-167) and transferred into bacteria resulting in continuous light emission independent of exogenously added substrate (Fernandez-Pinas and Wolk, Gene 150 (1994), 169-174). Bacteria containing the complete lux operon sequence, when injected intraperitoneally, intramuscularly, or intravenously, allowed the visualization and localization of bacteria in live mice indicating that the luciferase light emission can penetrate the tissues and can be detected externally (Contag et al., Mol. Microbiol. 18 (1995), 593-603).

Thus, in an even more preferred embodiment, the microorganism or cell containing a DNA sequence encoding a luciferase additionally contains a gene encoding a substrate for a luciferase.

Preferably, the microorganism is a bacterium. Particularly preferred is attenuated *Salmonella thyphimurium*, attenuated *Vibrio cholerae*, attenuated *Listeria monocytogenes* or *E. coli*.

Alternatively, viruses such as *Vaccinia* virus, AAV, a retrovirus etc. are also useful for the diagnostic and therapeutic uses of the present invention. Preferably, the virus is *Vaccinia* virus.

Preferably, the cell for the uses of the present invention is a mammalian cell such as a stem cell which can be autologous or heterologous concerning the organism.

In a further preferred embodiment, the microorganism or cell useful in the present invention contains a ruc-gfp expression cassette which contains the *Renilla* luciferase (ruc) and *Aequorea* gfp cDNA sequences under the control of a strong synthetic early/late (PE/L) promoter of *Vaccinia* or the luxCDABE cassette.

In a preferred use of the microorganisms and cells described above the protein suitable for the therapy of diseases associated with wounded or inflamed tissue like atherosclerotic diasease is an enzyme causing cell death or an enzyme causing the digestion of debris, e.g. in the interior of an atherosclerotic plaque causing the plaque to collapse under the force of the intraluminal blood pressure. Suitable enzymes include a lipase, protease, lysozyme, proapoptotic factor, PPAR-agonist etc. If the inflammatory component of atherosclerosis should be treated suitable compounds are cortisol, corticosteroid analogs, cyclooxygenase and cyclooxygenase-2 inhibitors, colchicine, methotrexate, NSAIDs, leflunomide, etanercept, minocycline, cyclosporine, thalidomide, infliximab, IL-10, 6-mercaptopurine, azathioprine or a cytotoxic agent. Some of these compounds might be in the form of pro-drugs.

Accordingly, the protein expressed by a microorganism of the invention can be an enzyme converting an inactive substance (pro-drug) administered to the organism into an active substance.

Preferably, the gene encoding an enzyme as discussed above is directed by an inducible promoter additionally ensuring that, e.g., the conversion of the pro-drug into the active substance only occurs in the target tissue, e.g., an IPTG-, antibiotic-, heat-, pH-, light-, metal-, aerobic-, host cell-, drug-, cell cycle- or tissue specific-inducible promoter. Moreover, the delivery system of the present invention even allows the application of compounds which could so far not be used for therapy due to their high toxicity when systemically applied or due to the fact that they cannot be administered, e.g., intravenously in sufficiently high dosages to achieve levels inside, e.g., sinuses, abscesses or across the blood brain barrier. Such compounds include thalidomide, cytotoxic drugs, antibiotics etc.

Furthermore, the microorganism or cell of the present invention can contain a BAC (Bacterial Artificial Chromosome) or MAC (Mammalian Artificial Chromosome) encoding several or all proteins of a specific pathway, e.g. wound-healing-pathway, such as TNF-alpha, COX-2, CTGF etc. Additionally, the cell can be a cyber cell or cyber virus encoding these proteins.

For administration, the microorganisms or cells described above are preferably combined with suitable pharmaceutical carriers. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Administration of the microorganisms or cells may be effected by different ways, e.g. by intravenous, intraperetoneal, subcutaneous, intramuscular, topical or intradermal administration. The preferred route of administration is intravenous injection. The route of administration, of course, depends on the nature of the tissue and the kind of microorganisms or cells contained in the pharmaceutical composition. The dosage regimen will be determined by the attending physician and other clinical factors. As is well known in the medical arts, dosages for any one patient depends on many factors, including the patient's size, body surface area, age, sex, the particular compound to be administered, time and route of administration, the kind and localisation of the tissue, general health and other drugs being administered concurrently.

A preferred therapeutical use is the preparation of a pharamaceutical composition for the treatment of endocarditis, pericarditis, imflammatory bowel disease (e.g. Crohn's disease or Ulcerative colitis), low back pain (herniated nucleus pulposis), temporal arteritis, polyarteritis nodosa or an arthritic disease.

In the past few years, there has been many reports showing evidence for *Chlamydia pneumoniae*, *Heliobacter pylori*, CMV, HSV and other infectious agents inside atherosclerotic plaques. The presence of these infectious agents within atherosclerotic plaque suggests that the interior of the plaque is a protected environment that permits replication, otherwise these infectious agents would be cleared by the immune system. Moreover, there is considerable evidence that an inflammatory process is present within the interior of atherosclerotic plaque. Accordingly, it is reasonable to assume that this disease can be diagnosed and treated by the microorganisms or cells of the present invention that—after intravenous injection—will penetrate into the atherosclerotic plaque where they start to replicate. After a suitable period of time, the plaque can be imaged using, e.g., light sensitive cameras or suitable MRI equipment. Further, said microorganisms or cells can additionally produce an enzyme, e.g. an enzyme as described above, resulting in the elimination of plaques. Thus, a further preferred use is the diagnosis and treatment of an atherosclerotic disease.

A further preferred use is the diagnosis and treatment of coronary artery disease, peripheral vascular disease or cerebral artery disease. Therapeutic treatments according to the present invention might replace treatments like balloon angioplasty, stent placement, coronary artery bypass graft, carotid endarterectomy, aorto-femoral bypass graft and other invasive procedures. Moreover, plaque in inaccessible regions, such as the basilar and middle cerebral arteries can be treated using the therapeutic approach of the present invention.

For the therapy of wounds, fractures, surgical incisions and burns the microorganisms of the present invention are preferably combined with proteins like transforming growth factor (TGF-alpha), platelet-derived growth factor (PDG-F), keratinocyte growth factor (KGF) and insulin-like growth factor-1 (IGF-1), insulin-like growth factor-binding proteins (IGFBPs), IL-4, IL-8, endothelin-1 (ET-1), connective tissue growth factor (CTGF), TNF-alpha, vascular endothelial growth factor (VEGF), cyclooxygenase, cyclooxygenase-2 inhibitor, infliximab (a chimeric anti-TNF-alpha monoclonal antibody), IL-10, lipase, protease, lysozyme, pro-apoptotic factor, peroxisome proliferator-activated receptor (PPAR) agonist (or contain expressible DNA-sequences encoding said proteins). For the treatment of infectious diseases, the microorganisms of the present invention are preferably applied in combination with antibiotics. For the treatment of auto-immune and inflammatory diseases, including reumathoid arthritis, inflammatory bowel disease and multiple sclerosis, the microorganisms of the present invention are preferably applied in combination with cortisol, corticosteroid analogs, cyclooxygenase and cyclooxygenase-2 inhibitors, colchicine, methotrexate, NSAIDs, leflunomide, etanercept, minocycline, cyclosporine, thalidomide, infliximab, IL-10, 6-mercaptopurine, azathioprine or a cytotoxic agent. For the therapy of diseases like atherosclerosis, the microorganisms of the present invention are preferably applied in combination with lipases, lysozymes, pro-apoptopic factors, PPAR-agonists (or the corresponding DNA-sequences) or an agent listed above with respect to the treatment of inflammatory diseases. For the treatment of Alzheimer's disease, the microorganisms of the present invention are preferably applied in combination with one or more agents listed above with respect to auto-immune- or inflammatory diseases.

Finally, the above described microorganisms and cells are useful for (a) monitoring the efficacy of an antibiotic regimen, preferably based on light extinction or (b) comparing the resistance of various sutures and implantable materials to bacterial colonization.

BRIEF DESCRIPTION OF THE DRAWINGS

FIG. 1: Visualization of Bacteria Intravenously Injected into Nude Mice

Nude mice were injected with $1\times10^7$ attenuated *Salmonella typhimurium* (A) or $1\times10^7$ attenuated *Vibrio cholera* (B). Both strains were transformed with pLITE201 carrying the lux operon. Photon collection was for one minute 20 min after bacterial injections.

Figure 2:
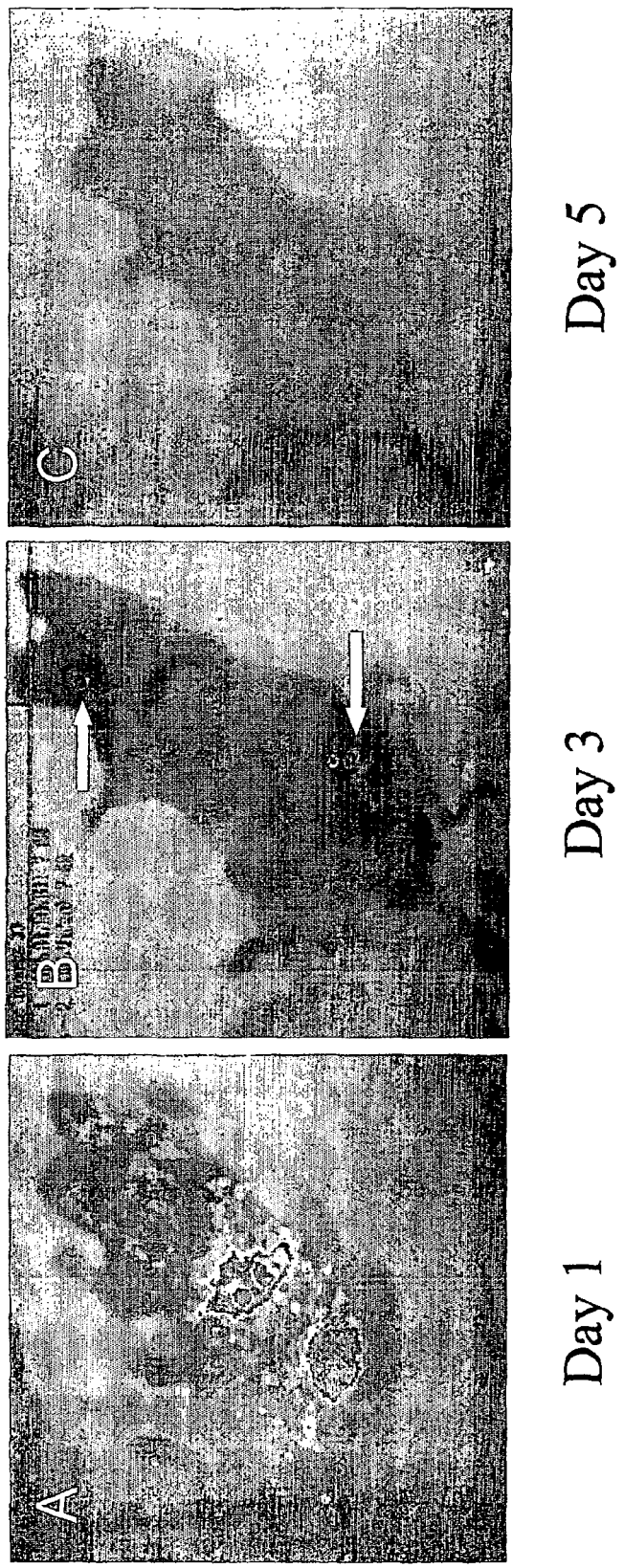

FIG. 2: Visualization of *S. typhimurium* in the Same Animal Over a 5-Day Observation Period Nude mice were injected with $1\times10^7$ attenuated *S. typhimurium*. On the first observation period, bacteria were disseminated throughout the body of the animal (A). Two days later, bacteria were cleared from the animal with the exception of the incision wound and the ear tag region as indicated by the arrows (B). On day 5, the animal had been able to clear the organism from the wounded regions (C).

Figure 3:
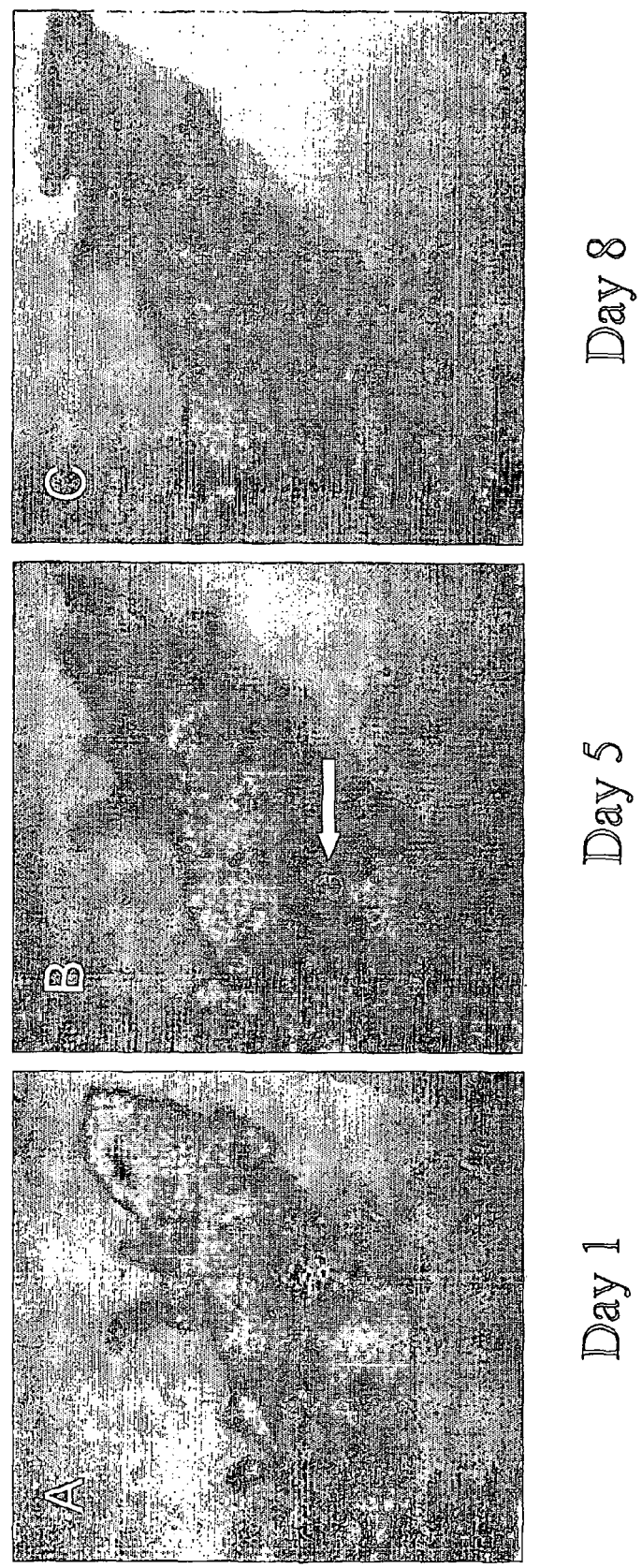

FIG. 3: Visualization of *V. cholera* in the Same Animal Over an 8-Day Observation Period Nude mice were injected with $1\times10^7$ attenuated *V. cholera*. On the first observation period, bacteria were visualized in the liver region of the animal (A). Five days later, bacteria were cleared from the entire animal with the exception of the incision wound as indicated by the arrows (B). On day 8, the animal had been able to clear the organism from the wound (C).

Figure 4:
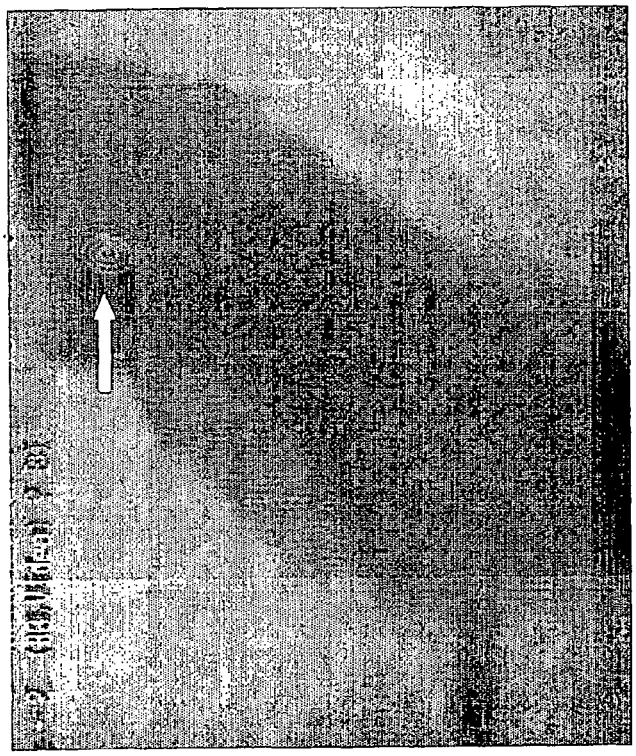

FIG. 4: Visualization of *V. cholera* in an Immunocompetent C57 Mouse $1\times10^7$ attenuated *V. cholera* were intravenously injected into the animal. Light-emitting bacteria colonized the ear tag on the forth day after bacterial injection (indicated by the white arrow).

Figure 5:
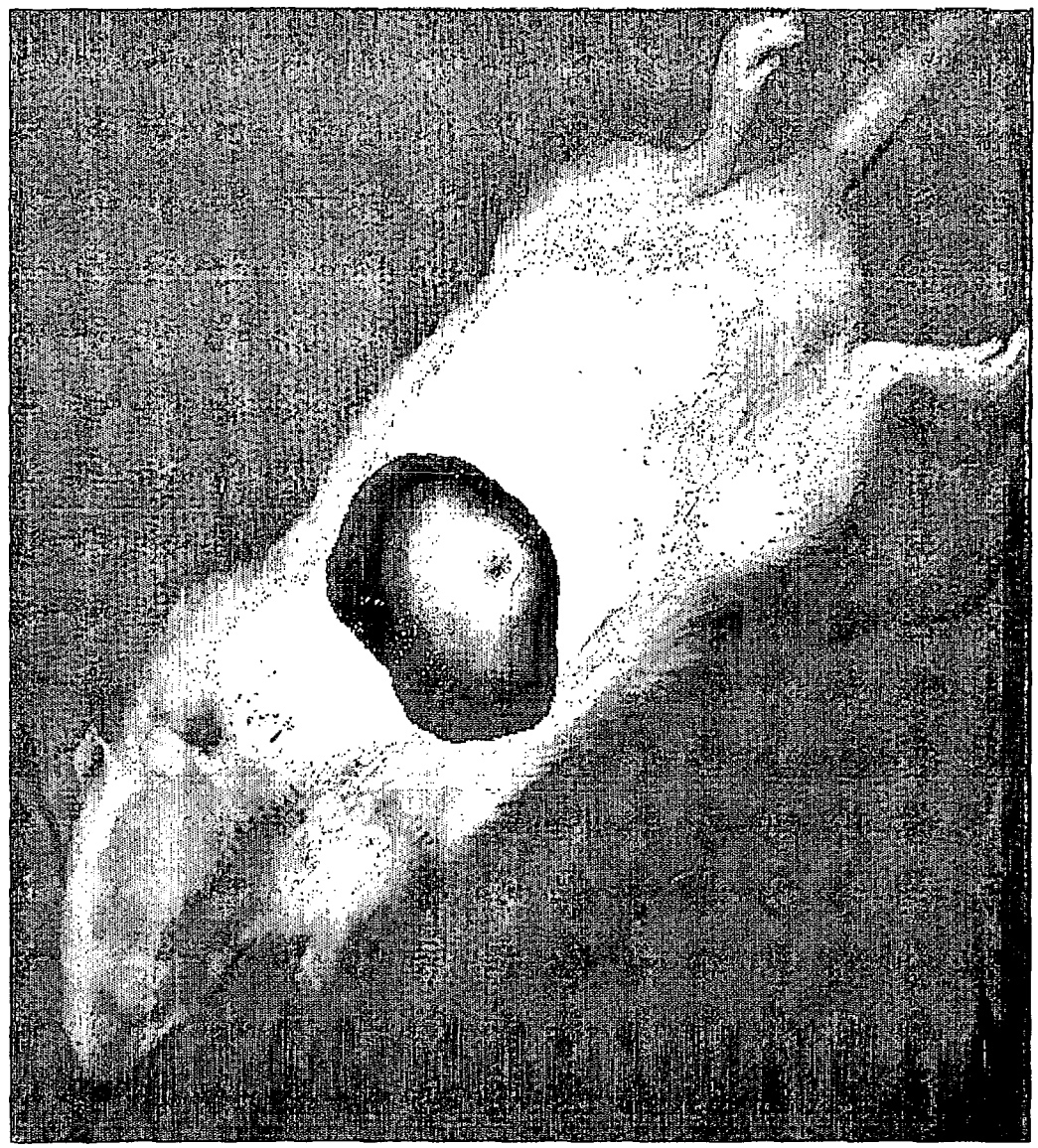

FIG. 5: Visualization of Light Emitting Bacteria in the Liver of Rats

Sprague Dawley rats were intravenously injected with $1\times10^8$ attenuated *E. coli* transformed with the plasmid DNA pLITE201 carrying the luxcdabe operon. Photons were collected immediately after infection for one minute under the low light imager (Night Owl). Light emitting bacteria were visualized in the liver of the whole live animal.

FIG. 6: Colonization of Rat Hearts with Light Emitting Bacteria

Intravenous injection of the rats with $1\times10^8$ attenuated *E. coli* transformed with the plasmid pLITE201 carrying the luxcdabe operon did not lead to colonization of the hearts of control animals, which had not been catheterized (A). Similar induction of bacteremias in rats catheterized through the right carotid artery lead to the colonization of the heart with light emitting bacteria (B).

Figure 7:

FIG. 7: Detection of Residual Bacteria in the Organs of Rats

Three days following intravenous injection of the rats with $1 \times 10^8$ attenuated *E. coli*, the hearts, livers, and spleens were excised and cultured overnight. Light emitting bacteria were visualized under the low light imager (Hamamatsu) in all specimens from the catheterized rats (A-C), while in the control animals, bacteria were detected in the liver (A) and spleen (B) but not the heart (C).

The present invention is explained by the following examples.

EXAMPLE 1

Materials and Methods (A) Bacterial Strains

The strains used were a non-pathogenic laboratory strain *Escherichia coli*, strain DH5α, attenuated *Salmonella typhimurium* (SL7207 hisG46, DEL407 [aroA544::Tn101] and attenuated *Vibrio cholerae* (Bengal 2 Serotyp 0139, M010 DattRSI).

(B) Plasmid Constructs

The plasmid DNA pLITE201 containing the luxcdabe gene cassette was obtained from Dr. F. Marines (Voisey and Marines, Biotech. 24 (1998) 56-58).

(C) Recipient Animals

Five- to six-week-old male BALB/c nu/nu mice (25-30 g body weight) and Sprague Dawley rats (300-325 g body weight) were purchased from Harlan (Frederick, Md., USA). CS7BL/6J mice were obtained from Jackson Laboratories (Bar Harbor, Me., USA). All animal experiments were carried out in accordance with protocols approved by the Lorna Linda University animal research committee. The animals containing recombinant DNA materials and attenuated pathogens were kept in the Loma Linda University animal care facility at biosafety level two.

(D) Detection of Luminescence

Immediately before imaging, the animals were anesthetized with intraperitoneal injections of sodium pentobarbital (Nembutal® Sodium solution, Abbot Laboratories, North Chicago, Ill.; 60 mg/kg body weight). The animals were placed inside the dark box for photon counting and recording superimposed images (ARGUS 100 Low Light Imaging System, Hamamatsu, Hamamatsu, Japan and Night Owl, Berthold Technologies, GmbH and Co. KG, Bad Wildbad, Germany). Photon collection was for one minute from ventral and dorsal views of the animals. A photographic image was then recorded and the low light image was superimposed over the photographic image to demonstrate the location of luminescent activity.

EXAMPLE 2

Colonization of Cutaneous Wounds by Intravenously Injected Light Emitting Bacteria in Live Animals To determine the fate of intravenously injected luminescent bacteria in the animals, $1 \times 10^7$ bacteria carrying the pLITE201 plasmid DNA in 50 µl were injected into the left femoral vein of nude mice under anesthesia. To expose the femoral vein, a 1-cm incision was made with a surgical blade. Following closure of the incision with 6-0 sutures, the mice were monitored under the low light imager and photon emissions were collected for one minute. Imaging of each animal was repeated at various time intervals to study the dissemination of the light-emitting bacteria throughout the body of the animals. It was found that the distribution pattern of light emission following an intravenous injection of bacteria into the mice was bacterial-strain-dependent. Injection of attenuated *S. typhimurium* caused wide dissemination of the bacteria throughout the body of the animals (FIG. 1A). This pattern of distribution was visible within 5 minutes after bacterial injection and continued to be detected at the one-hour observation period. Injection of attenuated *V. cholera* into the bloodstream, however, resulted in light emission that was localized to the liver within 5 minutes after bacterial injection and remained visible in the liver at the one-hour observation period (FIG. 1B).

The difference in the bacterial distribution patterns suggests a difference in the interaction of these strains with the host once inside the animal. Imaging the same animals 48 h after bacterial injection showed that all of the detectable light emission from the earlier time had diminished and was eliminated completely from the injected animal with the exception of the inflamed wounded tissues such as the incision wound and the ear tag region. Inflammation in these tissues was identified by their red and edematous appearance. Light emission was detected in the incision wound and/or in the inflamed ear tag region up to 5 to 8 days postinjection, which was confirmed by longer photon collection times, i.e. 10 minutes (FIG. 2A-C and FIG. 3A-C). The absence of light emission was not due to the loss of the plasmid DNA or the silencing of gene expression in the bacteria. In other experiments light emission in animals could be consistently detected for up to 50 days. Similar data were obtained in immunocompetent C57BU6J mice (FIG. 4), showing that these observations are not limited to animals with altered immune systems. Careful examination of individually excised organs as well as blood samples from infected animals confirmed the absence of luminescence in these normal uninjured tissues. Furthermore, the experimental data demonstrated that colonization of the injured tissues is a common occurrence in mice. Twenty-four of 29 incision wounds (82.8%) and 12 of 29 ear tags (41.4%) in the mice were colonized by intravenously injected bacteria. Wound colonization by intravenously injected bacteria occurred following injection of *V. cholera* in concentrations as low as $1 \times 10^5$ bacterial cells.

EXAMPLE 3

Colonization of Catheterized Rat Hearts Subsequent to Femoral Vein Injection of Light-Emitting Bacteria Surgical heart defects were created according to the procedures previously described (Santoro and Levison, Infect. Immun. 19(3)(1978), 915-918; Overholser et al., J. Infect. Dis. 155(1)(1987), 107-112). Briefly, animals were anesthetized with sodium pentobarbital (60 mg/kg i.p.). A midline neck incision was made to expose the tight carotid artery. A polypropylene catheter was introduced and advanced until resistance was met indicating insertion to the level of the aortic valve. The catheter was then secured using a 10-0 suture (AROSurgical Instrument Corporation, Japan) and the incision was closed using 4-0 silk sutures (American Cyanamide Company, Wayne, N.J.). Placement of the catheter causes irritation and subsequent inflammation of the aortic valve (Santoro and Levison, 1978). Control animals did not undergo the catheterization procedure. Bacteremias were induced by injection of $1 \times 10^8$ light-emitting bacterial cells of *E. coli* via the femoral vein. When observed immediately after infection under the low light imager, bacterial colonization was visible in the liver region (FIG. 5). Three days later, while catheterized animals consistently demonstrated colonization of the heart with light emitting bacteria, control animals showed no sign of light emission from the heart (FIG. 6). To determine if low and undetectable levels of bacteria were present in the tissues, the heart, liver and spleen were excised from each animal and cultured overnight. The livers and spleens of the rats, which are organs that are directly involved in bacterial clearance, in both groups showed presence of light emitting bacteria. Strong light emission was detected in the catheterized heart in contrast to the control heart, which had complete absence of emitted light (FIG. 7). No bacteria were detected on the cultured catheters.

These findings indicate that while light-emitting bacteria injected into the bloodstream via the femoral vein were cleared from normal tissues, injured or inflamed tissues in immunocompromised and immunocompetent animals provided sites that continued to retain bacteria for an extended period of time.

The invention claimed is:

1. A method for diagnosis by imaging wounded or inflamed tissue inside of a live subject, comprising:
   identifying a subject suspected of having an internal wound or inflammation to be tested for the presence or absence of internal wounded tissue or internal inflamed tissue;
   systemically administering to the subject in whom the presence or absence of a wounded tissue or inflamed tissue is to be detected, a bacterium, wherein:
   the bacterium encodes a protein that is detectable by imaging in the subject or encodes a protein that induces a signal detectable by imaging;
   the bacterium replicates in the subject;
   the bacterium is not pathogenic to the subject and is recognized by the immune system of the subject;
   the bacterium is not targeted; and
   after a sufficient time for the bacterium to accumulate in wounded or inflamed tissues inside of the subject, imaging the detectable bacterium inside of the live subject to detect accumulation of the bacterium in the subject, and thereby imaging wounded or inflamed tissues inside of the live subject, wherein imaging the accumulation indicates the location of wounded tissue or inflamed tissue inside of the subject.

2. The method of claim 1, wherein the bacterium encodes a protein(s) for the therapy of the imaged wounded or inflamed tissue.

3. The method of claim 1, wherein the bacterium encodes a luminescent or fluorescent protein.

4. The method of claim 1, wherein the bacterium encodes a luciferase, red fluorescent protein or green fluorescent protein.

5. The method of claim 4, wherein the bacterium encodes a luciferase and a protein(s) for the production of a substrate for a luciferase.

6. A method for detecting wounded or inflamed tissue inside a subject, comprising:
   identifying a subject to be tested for the presence or absence of wounded tissue or inflamed tissue therein;
   systemically administering to the subject in whom the presence or absence of a wounded tissue or inflamed tissue is to be detected, a bacterium, wherein:
   the bacterium is detectable by imaging in the subject;
   the bacterium replicates in the subject;
   the bacterium is not pathogenic to the subject and is recognized by the immune system of the subject;
   the bacterium is not targeted; and
   after a sufficient time for the bacterium to accumulate in wounded or inflamed tissues inside of the subject, imaging the detectable bacterium inside of the subject to detect accumulation of the bacterium in the subject, and thereby detecting wounded or inflamed tissues inside of the subject, wherein:
   detection of the accumulation indicates the location of wounded tissue or inflamed tissue inside of the subject; and the bacterium encodes a protein that induces a signal detectable by magnetic resonance imaging (MRI) or that binds to contrasting agent, chromophore or a ligand.

7. The method of claim 1, wherein the bacterium is selected among an attenuated *Salmonella typhimurium*, an attenuated *Vibrio cholerae*, an attenuated *Listeria monocytogenes* and *E. coli*.

8. The method of claim 2, wherein the protein for the therapy is an enzyme that causes cell death or an enzyme that causes the digestion of debris.

9. The method of claim 2, wherein the subject in whom the presence or absence of wounded tissue or inflamed tissue is detected has a disease selected among endocarditis, pericarditis, inflammatory bowel disease, low back pain (herniated nucleus pulposis), temporal arteritis, polyarteritis nodosa and an arthritic disease.

10. A method for detecting wounded or inflamed tissue inside of a subject, comprising:
    identifying a subject to be tested for the presence or absence of wounded tissue or inflamed tissue therein;
    systemically administering to the subject in whom the presence or absence of a wounded tissue or inflamed tissue is to be detected, a bacterium, wherein:
    the bacterium is detectable by imaging in the subject;
    the bacterium replicates in the subject;
    the bacterium is not pathogenic to the subject and is recognized by the immune system of the subject;
    the bacterium is not targeted; and
    after a sufficient time for the bacterium to accumulate in wounded or inflamed tissues inside of the subject, imaging the detectable bacterium inside of the subject to detect accumulation of the bacterium in the subject, and thereby detecting wounded or inflamed tissues inside of the subject, wherein:
    detection of the accumulation indicates the location of wounded tissue or inflamed tissue inside of the subject;
    the bacterium encodes a protein(s) for the therapy of the detected imaged wounded or inflamed tissue; and
    the subject for whom the presence or absence of wounded tissue or inflamed tissue is detected has an atherosclerotic disease.

11. The method of claim 2, wherein the subject for whom the presence or absence of wounded tissue or inflamed tissue is detected has a disease that is selected among coronary artery disease, peripheral vascular disease and cerebral artery disease.

12. A method for detecting wounded or inflamed tissue inside of a subject, comprising:
    identifying a subject to be tested for the presence or absence of wounded tissue or inflamed tissue therein;
    systemically administering to the subject in whom the presence or absence of a wounded tissue or inflamed tissue is to be detected, a bacterium, wherein:
    the bacterium is detectable by imaging in the subject;
    the bacterium replicates in the subject;
    the bacterium is not pathogenic to the subject and is recognized by the immune system of the subject;
    the bacterium is not targeted; and
    after a sufficient time for the bacterium to accumulate in wounded or inflamed tissues inside of the subject, imaging the detectable bacterium inside of the subject to detect accumulation of the bacterium in the subject, and thereby detecting wounded or inflamed tissues inside of the subject, wherein:

detection of the accumulation indicates the location of wounded tissue or inflamed tissue inside of the subject; and the detecting is performed by magnetic resonance imaging (MRI).

13. The method of claim 2, wherein the bacterium contains an inducible promoter that regulates the expression of the therapeutic protein.

14. A method for detecting wounded or inflamed tissue inside of a subject, comprising:

identifying a subject to be tested for the presence or absence of wounded tissue or inflamed tissue therein;

systemically administering to the subject in whom the presence or absence of a wounded tissue or inflamed tissue is to be detected, a bacterium, wherein:

the bacterium is detectable by imaging in the subject;

the bacterium replicates in the subject;

the bacterium is not pathogenic to the subject and is recognized by the immune system of the subject;

the bacterium is not targeted; and after a sufficient time for the bacterium to accumulate in wounded or inflamed tissues inside of the subject, imaging the detectable bacterium inside of the subject to detect accumulation of the bacterium in the subject, and thereby detecting wounded or inflamed tissues inside of the subject, wherein:

detection of the accumulation indicates the location of wounded tissue or inflamed tissue inside of the subject;

the disease is an atherosclerotic disease; and the therapeutic protein is selected from among a lipase, protease, lysozyme, proapoptotic factor and PPAR-agonist.

15. The method of claim 1, further comprising:

administering a therapeutic agent for the therapy of a wounded tissue, inflamed tissue or a disease associated therewith.

16. A method for detecting wounded or inflamed tissue inside of a subject, comprising:

intravenously or intramuscularly administering to a subject in whom the presence or absence of a wounded tissue or inflamed tissue is to be detected, a bacterium, wherein:

the bacterium is detectable in the subject;

the bacterium replicates in the subject;

the bacterium is not pathogenic to the subject and is recognized by the immune system of the subject;

the bacterium is not targeted; and after a sufficient time for the bacterium to accumulate in wounded or inflamed tissues inside of the subject, monitoring or imaging the detectable bacterium inside of the subject to detect accumulation of the bacterium in the subject, and thereby detecting wounded or inflamed tissues inside of the subject.

17. The method of claim 16, further comprising:

administering a therapeutic agent for the therapy of a wounded tissue, inflamed tissue or a disease associated therewith.

18. The method of claim 16, wherein the bacterium is selected among an attenuated *Salmonella typhimurium*, an attenuated *Vibrio cholerae*, an attenuated *Listeria monocytogenes* and *E. coli*.

19. The method of claim 16, wherein the bacterium encodes a protein(s) for the therapy of the detected wounded or inflamed tissue.

20. The method of claim 16, wherein the bacterium encodes a luminescent or fluorescent protein.

21. The method of claim 16, wherein the bacterium encodes a luciferase, red fluorescent protein or green fluorescent protein.

22. The method of claim 21, wherein the bacterium encodes a luciferase and a protein(s) for the production of a substrate for a luciferase.

23. The method of claim 19, wherein the protein for the therapy is an enzyme that causes cell death or an enzyme that causes the digestion of debris.

24. The method of claim 17, wherein the subject in whom the presence or absence of wounded tissue or inflamed tissue is detected has a disease selected among endocarditis, pericarditis, inflammatory bowel disease, low back pain (herniated nucleus pulposis), temporal arteritis, polyarteritis nodosa and an arthritic disease.

* * * * *

UNITED STATES PATENT AND TRADEMARK OFFICE
CERTIFICATE OF CORRECTION

| | | |
|---|---|---|
| PATENT NO. | : 8,137,904 B2 | Page 1 of 1 |
| APPLICATION NO. | : 10/516785 | |
| DATED | : March 20, 2012 | |
| INVENTOR(S) | : Szalay et al. | |

It is certified that error appears in the above-identified patent and that said Letters Patent is hereby corrected as shown below:

THE TITLE PAGES:

In Item (56) References Cited, in OTHER PUBLICATIONS:

At page 15, col. 2, line 3, replace "Morena, A., et al.," with --Moretta, A., et al.,--

At page 18, col. 2, line 42, replace "12/081,766" with --12/080,766--

Signed and Sealed this
Seventh Day of August, 2012

David J. Kappos
*Director of the United States Patent and Trademark Office*